US008466151B2

(12) United States Patent
Danter et al.

(10) Patent No.: US 8,466,151 B2
(45) Date of Patent: Jun. 18, 2013

(54) COMPOUNDS AND METHOD FOR TREATMENT OF CANCER

(75) Inventors: Wayne R Danter, London (CA); Cheuk Kun Kun Lau, Montreal (CA)

(73) Assignee: Critical Outcome Technologies, Inc., London, Ontario (CA)

( * ) Notice: Subject to any disclaimer, the term of this patent is extended or adjusted under 35 U.S.C. 154(b) by 0 days.

(21) Appl. No.: 12/810,722

(22) PCT Filed: Dec. 24, 2008

(86) PCT No.: PCT/CA2008/002293

§ 371 (c)(1),
(2), (4) Date: Dec. 24, 2008

(87) PCT Pub. No.: WO2009/079797

PCT Pub. Date: Jul. 2, 2009

(65) Prior Publication Data

US 2011/0152281 A1 Jun. 23, 2011

Related U.S. Application Data

(60) Provisional application No. 61/006,150, filed on Dec. 26, 2007.

(51) Int. Cl.

*A01N 43/58* (2006.01)
*A01N 43/60* (2006.01)
*A61K 31/50* (2006.01)
*A61K 31/495* (2006.01)

(52) U.S. Cl.

USPC ....... 514/248; 544/224; 544/238; 514/252.02

(58) Field of Classification Search

USPC ........................................................ 544/224

See application file for complete search history.

(56) References Cited

U.S. PATENT DOCUMENTS

| | | | |
|---|---|---|---|
| 3,239,539 | A | 3/1966 | Bartlett et al. |
| 3,250,791 | A | 5/1966 | Webster et al. |
| 3,671,639 | A | 6/1972 | Sasse et al. |
| 4,463,077 | A | 7/1984 | Matsuura et al. |
| 4,537,844 | A | 8/1985 | Hashimoto |
| 4,593,027 | A | 6/1986 | Winklemann et al. |
| 4,619,878 | A | 10/1986 | Hashimoto |
| 4,748,160 | A | 5/1988 | Bennion et al. |
| 4,927,843 | A | 5/1990 | Teitz |
| 4,977,051 | A | 12/1990 | Ohno et al. |
| 4,978,670 | A | 12/1990 | Rector et al. |
| 4,985,433 | A | 1/1991 | Secrist, III et al. |
| 4,985,434 | A | 1/1991 | Secrist, III et al. |
| 5,008,265 | A | 4/1991 | Secrist, III et al. |
| 5,008,270 | A | 4/1991 | Secrist, III et al. |
| 5,023,334 | A | 6/1991 | Rector et al. |
| 5,135,928 | A | 8/1992 | Reiter et al. |
| 5,155,110 | A | 10/1992 | Connor et al. |
| 5,189,039 | A | 2/1993 | Niwas et al. |
| 5,196,291 | A | 3/1993 | Okada et al. |
| 5,292,756 | A | 3/1994 | Duggan et al. |
| 5,328,914 | A | 7/1994 | Hocquaux et al. |
| 5,334,748 | A | 8/1994 | Buckley et al. |
| 5,344,836 | A | 9/1994 | Hamanaka et al. |
| 5,358,946 | A | 10/1994 | Wilde |
| 5,409,930 | A | 4/1995 | Spada et al. |
| 5,441,847 | A | 8/1995 | Fukawa et al. |
| 5,480,883 | A | 1/1996 | Spada et al. |
| 5,521,184 | A | 5/1996 | Zimmermann |
| 5,543,520 | A | 8/1996 | Zimmermann |
| 5,604,210 | A | 2/1997 | Nagaoka et al. |
| 5,612,340 | A | 3/1997 | Zimmermann |
| 5,618,829 | A | 4/1997 | Takayanagi et al. |
| 5,646,153 | A | 7/1997 | Spada et al. |
| 5,656,643 | A | 8/1997 | Spada et al. |
| 5,710,158 | A | 1/1998 | Myers et al. |
| 5,714,493 | A | 2/1998 | Myers et al. |
| 5,721,238 | A | 2/1998 | Heiker et al. |
| 5,736,534 | A | 4/1998 | Arnold |
| 5,750,088 | A | 5/1998 | Sworin et al. |
| 5,760,041 | A | 6/1998 | Wissner et al. |
| 5,763,470 | A | 6/1998 | Tang et al. |
| 5,795,889 | A | 8/1998 | Spada et al. |
| 5,798,451 | A | 8/1998 | Von Deyn et al. |
| 5,872,272 | A | 2/1999 | Yano et al. |

(Continued)

FOREIGN PATENT DOCUMENTS

| | | |
|---|---|---|
| CA | 2109975 | 5/1994 |
| CA | 2553242 | 8/2005 |

(Continued)

OTHER PUBLICATIONS

WO 2009/079797, International Search Report (Jun. 29, 2010).*
M. Braun et al., Monatsheft für Chemie, 109(1), 63-71 (1978).*
S.R. Byrn et al, Solid-State Chemistry of Drugs, 516 (2nd ed., 1999). Hydrates are a subset of solvates wherein the solvent is water. Id. at 233-247, 233-234.*
G. Heinisch et al., 104 Monatshefte für Chemie, 1372-1382 (1973).*
M. Braun et al., 109 Monatsheft für Chemie, 63-71 (1978).*
J. Easmon et al., 29 Heterocycles, 1399-1408 (1989).*
Caplus Accession No. 2008:468805, Document No. 148:472058 (2008) (CAPLUS Abstract JP 2008088107).*
Anderson et al., "Some Heterocyclic Thiosemicarbazones", Oct. 1951, Journal of the American Chemical Society, vol. 73, p. 4967-4968.

(Continued)

*Primary Examiner* — James O Wilson
*Assistant Examiner* — Alexander R Pagano
(74) *Attorney, Agent, or Firm* — Swanson & Bratschun, L.L.C.

(57) ABSTRACT

The invention relates to a compound of Formula (I) and/or a pharmaceutically-acceptable salt, hydrate, solvate, tautomer, optical isomer, E-isomer, Z-isomer, or combination thereof, wherein X is selected from S or O; $R^5$ is selected from a substituted or unsubstituted aromatic group, a substituted or unsubstituted heteroaromatic group, or (Formula II) and the remaining substituents are described herein; and a composition comprising the thiosemicarbazone and/or the semicarbazone. The invention also relates to a method of administration of a thiocarbazone and/or a semicarbazone; and use thereof to treat a cancer.

16 Claims, 14 Drawing Sheets

U.S. PATENT DOCUMENTS

| | | | |
|---|---|---|---|
| RE36,256 | E | 7/1999 | Spada |
| 5,932,574 | A | 8/1999 | Baker |
| 5,948,819 | A | 9/1999 | Ohtsuka et al. |
| 5,958,935 | A | 9/1999 | Davis et al. |
| 5,977,146 | A | 11/1999 | Muller et al. |
| 6,057,320 | A | 5/2000 | Spada et al. |
| 6,069,134 | A | 5/2000 | Roth et al. |
| 6,103,728 | A | 8/2000 | Tang et al. |
| 6,127,374 | A | 10/2000 | Bridges |
| 6,153,617 | A | 11/2000 | Bridges |
| 6,156,617 | A | 12/2000 | Saitoh |
| 6,169,091 | B1 | 1/2001 | Cockerill et al. |
| 6,174,889 | B1 | 1/2001 | Cockerill et al. |
| 6,180,636 | B1 | 1/2001 | Traxler et al. |
| 6,184,377 | B1 | 2/2001 | Gao |
| 6,207,669 | B1 | 3/2001 | Cockerill et al. |
| 6,235,746 | B1 | 5/2001 | Davis et al. |
| 6,251,911 | B1 | 6/2001 | Bold et al. |
| 6,268,391 | B1 | 7/2001 | Dickerson et al. |
| 6,352,168 | B1 | 3/2002 | Lin |
| RE37,650 | E | 4/2002 | Myers et al. |
| 6,391,874 | B1 | 5/2002 | Cockerill et al. |
| 6,420,560 | B1 | 7/2002 | Numerof et al. |
| 6,432,963 | B1 | 8/2002 | Hisamichi et al. |
| 6,525,072 | B1 | 2/2003 | Tang et al. |
| 6,528,509 | B1 | 3/2003 | Hale et al. |
| 6,538,002 | B1 | 3/2003 | Finke et al. |
| 6,562,818 | B1 | 5/2003 | Bridges |
| 6,600,037 | B1 | 7/2003 | Davis et al. |
| 6,635,641 | B2 | 10/2003 | Bender et al. |
| 6,723,726 | B1 | 4/2004 | Cockerill et al. |
| 6,828,320 | B2 | 12/2004 | Cockerill et al. |
| 6,949,639 | B1 | 9/2005 | Hovinen et al. |
| 7,052,870 | B2 | 5/2006 | Sabatini et al. |
| 7,138,416 | B2 | 11/2006 | Sankaranarayanan |
| 7,175,844 | B2 | 2/2007 | King |
| 7,202,367 | B2 | 4/2007 | Cellier et al. |
| 8,034,815 | B2 | 10/2011 | Danter et al. |
| 8,138,191 | B2 | 3/2012 | Danter |
| 8,367,675 | B2 | 2/2013 | Danter et al. |
| 2001/0021717 | A1 | 9/2001 | Potter et al. |
| 2001/0027205 | A1 | 10/2001 | Camden |
| 2001/0041964 | A1 | 11/2001 | Grass et al. |
| 2001/0044451 | A1 | 11/2001 | Fraley et al. |
| 2001/0047007 | A1 | 11/2001 | Fraley et al. |
| 2001/0047364 | A1 | 11/2001 | Proctor |
| 2001/0049092 | A1 | 12/2001 | Ekins et al. |
| 2001/0051628 | A1 | 12/2001 | Huang et al. |
| 2002/0010550 | A1 | 1/2002 | Grass et al. |
| 2002/0012641 | A1 | 1/2002 | Voorhees et al. |
| 2002/0013334 | A1 | 1/2002 | Robl et al. |
| 2002/0013662 | A1 | 1/2002 | Grass et al. |
| 2002/0014408 | A1 | 2/2002 | Schroeder |
| 2002/0018988 | A1 | 2/2002 | Klinck et al. |
| 2002/0028779 | A1 | 3/2002 | High et al. |
| 2002/0028826 | A1 | 3/2002 | Robl et al. |
| 2002/0042423 | A1 | 4/2002 | Richert et al. |
| 2002/0061901 | A1 | 5/2002 | Robl et al. |
| 2002/0072526 | A1 | 6/2002 | Fraley et al. |
| 2002/0086791 | A1 | 7/2002 | Iglesia et al. |
| 2002/0115858 | A1 | 8/2002 | Zimmermann et al. |
| 2002/0147214 | A1 | 10/2002 | Cockerill et al. |
| 2002/0151540 | A1 | 10/2002 | Lai et al. |
| 2003/0087881 | A1 | 5/2003 | Bridges |
| 2003/0125343 | A1 | 7/2003 | Gambacorti-Passerini et al. |
| 2003/0130286 | A1 | 7/2003 | Denny et al. |
| 2003/0153755 | A1 | 8/2003 | Moffat et al. |
| 2003/0176396 | A1 | 9/2003 | Shea et al. |
| 2003/0181495 | A1 | 9/2003 | Lai et al. |
| 2003/0212269 | A1 | 11/2003 | Davis et al. |
| 2003/0236413 | A1 | 12/2003 | Cellier et al. |
| 2004/0092747 | A1 | 5/2004 | Bender et al. |
| 2004/0102453 | A1 | 5/2004 | Buerger et al. |
| 2004/0171032 | A1 | 9/2004 | Baker et al. |
| 2004/0204477 | A1 | 10/2004 | Moll et al. |
| 2004/0224968 | A1 | 11/2004 | Seidelmann et al. |
| 2004/0235786 | A1 | 11/2004 | Orr |
| 2004/0235798 | A1 | 11/2004 | Murthi et al. |
| 2005/0010017 | A1 | 1/2005 | Blakely et al. |
| 2005/0014169 | A1 | 1/2005 | Latham et al. |
| 2005/0131022 | A1 | 6/2005 | Player et al. |
| 2005/0192884 | A1 | 9/2005 | Raines |
| 2006/0019831 | A1 | 1/2006 | Reinhard et al. |
| 2006/0217426 | A1 | 9/2006 | Eto et al. |
| 2007/0197495 | A1 | 8/2007 | Chibale |
| 2007/0280928 | A1 | 12/2007 | Buck et al. |
| 2008/0004274 | A1 | 1/2008 | Diaz et al. |
| 2008/0171744 | A1 | 7/2008 | Danter et al. |
| 2011/0281887 | A1 | 11/2011 | Danter et al. |
| 2012/0077820 | A1 | 3/2012 | Danter et al. |
| 2012/0195887 | A1 | 8/2012 | Danter |

FOREIGN PATENT DOCUMENTS

| | | | | |
|---|---|---|---|---|
| CA | 2584179 | | | 4/2006 |
| CN | 1224005 | | | 7/1999 |
| CN | 1891701 | | | 1/2007 |
| CN | 1907970 | | | 2/2007 |
| DE | 3237649 | | | 4/1984 |
| DE | 4207400 | | | 9/1993 |
| DE | 4207400 | A1 | | 9/1993 |
| DE | 04400451 | | | 7/1994 |
| EP | 0 106 284 | | | 10/1983 |
| EP | 0 142 740 | | | 10/1984 |
| EP | 0 225 726 | | | 11/1986 |
| EP | 00172031 | | | 5/1988 |
| EP | 0 361 645 | | | 6/1989 |
| EP | 0329108 | | | 8/1989 |
| EP | 0 420 005 | | | 9/1990 |
| EP | 0 452 848 | | | 4/1991 |
| EP | 0425282 | | | 5/1991 |
| EP | 0 512 420 | | | 4/1992 |
| EP | 0 554 856 | | | 2/1993 |
| EP | 0 580 374 | | | 7/1993 |
| EP | 00571857 | | | 12/1993 |
| EP | 0600 832 | | | 6/1994 |
| EP | 0631179 | | | 12/1994 |
| EP | 0 722 937 | | | 1/1996 |
| EP | 0 727 701 | | | 2/1996 |
| EP | 00727701 | | | 8/1996 |
| EP | 0 807 580 | | | 5/1997 |
| EP | 0 902 028 | | | 8/1998 |
| EP | 00902028 | | | 3/1999 |
| EP | 00807850 | | | 10/2000 |
| EP | 01103549 | | | 5/2001 |
| EP | 01325921 | | | 7/2003 |
| FR | 2013371 | | | 4/1970 |
| FR | 2879194 | | | 6/2006 |
| GB | 1026401 | | | 4/1966 |
| GB | 1231783 | | | 5/1971 |
| GB | 2304471 | | | 3/1997 |
| GB | 2357971 | | | 7/2001 |
| JP | 56-095161 | | | 8/1981 |
| JP | 59088468 | | | 5/1984 |
| JP | 60184254 | | | 9/1985 |
| JP | 3093767 | | | 4/1991 |
| JP | 05058894 | | | 3/1993 |
| JP | 1993241264 | | | 9/1993 |
| JP | 06-247990 | | | 9/1994 |
| JP | 07-072571 | | | 3/1995 |
| JP | 1995114195 | | | 5/1995 |
| JP | 7219256 | | | 8/1995 |
| JP | 9328463 | | | 12/1997 |
| JP | 11080131 | | | 3/1999 |
| JP | 11-133545 | | | 5/1999 |
| JP | 11133545 | | | 5/1999 |
| JP | 2000143636 | | | 5/2000 |
| JP | 2001-172217 | | | 6/2001 |
| JP | 2001172217 | | | 6/2001 |
| JP | 2006-181940 | | | 7/2006 |
| JP | 2006181940 | | | 7/2006 |
| JP | 2008088107 | A | * | 4/2008 |
| WO | WO 86/04582 | | | 8/1986 |
| WO | WO 91/06548 | | | 5/1991 |
| WO | WO 92/03421 | | | 3/1992 |
| WO | WO 92/06076 | | | 4/1992 |
| WO | WO 92/08464 | | | 5/1992 |
| WO | WO 93/02091 | | | 2/1993 |

| | | |
|---|---|---|
| WO | WO 93/21187 | 10/1993 |
| WO | WO 94/18959 | 9/1994 |
| WO | WO 95/23796 | 2/1995 |
| WO | WO 95/17423 | 6/1995 |
| WO | WO 95/27693 | 10/1995 |
| WO | WO 96/05818 | 2/1996 |
| WO | WO 96/09294 | 3/1996 |
| WO | WO 96/14295 | 5/1996 |
| WO | WO 96/37472 | 11/1996 |
| WO | WO 97/00894 | 1/1997 |
| WO | WO 97/02238 | 1/1997 |
| WO | WO 97/03069 | 1/1997 |
| WO | WO 97/13760 | 4/1997 |
| WO | WO 98/08492 | 3/1998 |
| WO | WO 98/55448 | 12/1998 |
| WO | WO 99/09016 | 2/1999 |
| WO | WO 99/18102 | 4/1999 |
| WO | WO 99/62486 | 12/1999 |
| WO | WO 00/09126 | 2/2000 |
| WO | WO 00/18737 | 4/2000 |
| WO | WO 00/18740 | 4/2000 |
| WO | WO 00/50032 | 8/2000 |
| WO | WO 00/61186 | 10/2000 |
| WO | WO 00/74702 | 12/2000 |
| WO | WO 00/74742 | 12/2000 |
| WO | WO 01/12227 | 2/2001 |
| WO | WO 01/16271 | 3/2001 |
| WO | WO 01/34585 | 5/2001 |
| WO | WO 01/47899 | 7/2001 |
| WO | WO 01/53274 | 7/2001 |
| WO | WO 01/25220 | 9/2001 |
| WO | WO 01/64650 | 9/2001 |
| WO | WO 01/64825 | 9/2001 |
| WO | WO 01/64828 | 9/2001 |
| WO | WO 01/64994 | 9/2001 |
| WO | WO 01/66709 | 9/2001 |
| WO | WO 01/70741 | 9/2001 |
| WO | WO 02/22597 | 3/2002 |
| WO | WO 02/49413 | 6/2002 |
| WO | WO 02/068574 | 9/2002 |
| WO | WO 02/068577 | 9/2002 |
| WO | WO 02/070541 | 9/2002 |
| WO | WO 02/083126 | 10/2002 |
| WO | WO 03/004489 | 1/2003 |
| WO | WO 03/051276 | 6/2003 |
| WO | WO 03/070241 | 8/2003 |
| WO | WO 03/093297 | 11/2003 |
| WO | WO 2004/004725 | 1/2004 |
| WO | WO 2004/011456 | 2/2004 |
| WO | WO 2004/063147 | 7/2004 |
| WO | WO 2004/066725 | 8/2004 |
| WO | WO 2004/069801 | 8/2004 |
| WO | WO 2004/076640 | 9/2004 |
| WO | WO 2004/080492 | 9/2004 |
| WO | WO 2004/085382 | 10/2004 |
| WO | WO 2004/099371 | 11/2004 |
| WO | WO 2005/010017 | 2/2005 |
| WO | WO 2005/012252 | 2/2005 |
| WO | WO 2005/023183 | 3/2005 |
| WO | WO 2005/039489 | 5/2005 |
| WO | WO 2005/046604 | 5/2005 |
| WO | WO 2005/073189 | 8/2005 |
| WO | WO 2005/073216 | 8/2005 |
| WO | WO 2005/073217 | 8/2005 |
| WO | WO 2005/087211 | 9/2005 |
| WO | WO 2005/107463 | 11/2005 |
| WO | WO 2005/116039 | 12/2005 |
| WO | WO 2006/009765 | 1/2006 |
| WO | WO 2006/063863 | 6/2006 |
| WO | WO 2006/069080 | 6/2006 |
| WO | WO 2006/069807 | 7/2006 |
| WO | WO 2006/081425 | 8/2006 |
| WO | WO 2006/088919 | 8/2006 |
| WO | WO 2006/095542 | 9/2006 |
| WO | WO 2006/127379 | 11/2006 |
| WO | WO 2006/128129 | 11/2006 |
| WO | WO 2006/128172 | 11/2006 |
| WO | WO 2006/130462 | 12/2006 |
| WO | WO 2007/000432 | 1/2007 |
| WO | WO 2007/037898 | 4/2007 |
| WO | WO 2007/050980 | 5/2007 |
| WO | WO 2007/060404 | 5/2007 |
| WO | WO 2007/106503 | 9/2007 |
| WO | WO 2008/083491 | 7/2008 |
| WO | WO 2008/148074 | 12/2008 |
| WO | WO 2009/079797 | 7/2009 |

OTHER PUBLICATIONS

Bastos et al., "Structural analyses of 4-benzoylpyridine thiosemicarbazone using NMR techniques and theoretical calculations", 2005, Tetrahedron, vol. 61, p. 7045-7053.

Beraldo et al., "Structural studies and spectral characteristics of 4-benzoylpyridine thiosemicarbazone and N(4')-phenyl-4-benzoylpyridine thiosemicarbazone", 2003, Journal of Molecular Structure, vol. 645, p. 213-220.

Duca et al., "Studies in Experimental Tuberculosis In Vitro and In Vivo Activities of Thiosemicarbazones", 1952, Antibiotics and Chemotherapy, vol. II, No. 1, pp. 16-20.

Joshi et al., "Organic Pesticides. Part XIII. Synthesis of Some New Fluoro-ketones and their Thiosemicarbazones", 1963, Journal of Indian Chemical Society, vol. 40, No. 1, p. 42-44.

Al-Shahrour et al. (2007) Nucleic Acids Research 35:w91-w96, "FatiGO1: a functional profiling tool for genomic data. Integration of functional annotation, regulatory motifs and interaction data with microarray experiments".

Andes et al. (2002) International Journal of Antimicrobial Agents, 19:261-268, "Animal model pharmacokinetics and pharmacodynamics: a critical review".

Andrews et al. (1990) Cancer Communications 2(2):93-100, "Rapid emergence of acquired cis-Diamminedichloroplatinum(Il) Resistance in an in vivo model of human ovarian carcinoma".

Attoub et al. (2002) Cancer Research 62:4879-4883, "The c-kit tyrosine kinase inhibitor STI571 for colorectal cancer therapy".

Bain et al. (1997) Polyhedron 16(5):855-862, "Synthetic and spectroscopic investigations of N(4)-substituted isatin thiosemicarbazones and their copper(II) complexes".

Banker et al. (2002) Journal of Pharmaceutical Sciences 92(5):967-974, "Development and validation of a 96-well equilibrium dialysis apparatus for measuring plasma protein binding".

Bauer (1963) British Journal of Experimental Pathology, 44, 233-42, "The Chemotherapy of Ectromelia Infection with Isatin β-Dialkylthiosemicarbazones".

Bernhardt et al. (2003) Journal of Biological Inorganic Chemistry pp. 866-880, "Cytotoxic iron chelators: characterization of the structure, solution chemistry and redox activity of ligands and iron complexes of the di-2-pyridyl ketone isonicotinoyl hydrazone (HPKIH) analogues" http://dx.doi.org/IO.IOO7/s00775-003-0486-z.

Bernhardt et al (2008) Journal of Biological Inorganic Chemistry 13:107-119, "Tuning the antiproliferative activity of biologically active iron chelators: characterization of the coordination chemistry and biological efficacy of 2-acetylpyridine and 2-benzoylpyridine hydrazone ligands".

Berns et al. (2007) Cancer Cell 12:395-402, "A Functional Genetic Approach Identifies the PI3K Pathway as a Major Determinant of Trastuzumab Resistance in Breast Cancer".

Bjornsson et al. (2003) Drug Metabolism and Disposition 31:815-832, "The conduct of in vitro and in vivo drug-drug interaction studies: a pharmaceutical research and manufacturers of america (phrma) perspective".

Bolen (1993) Oncogene 8:2025-2031, "Nonreceptor tyrosine protein kinases".

Bowery et al. (2005) Current Opinion in Pharmacology 5(4):341-448, "Cancer/Immunomodulation".

Braun (1978) Monatshefte fur Chemie 109:63-71, "4,5•Diacylpyidazine: Synthese and Umsetzung zu 1,4-Diaryl- bzw. 1,4-Dialkyl-pyridazino[4,5—d]pyridazinen" English Abstract.

Britten et al. (1999) Cancer Research 59:1049-1053, "Enhanced antitumor activity of 6- hydroxymethylacylfulvene in combination with irinotecan and 5-fluorouracil in the HT29 human colon tumor xenograft model".

Brunn et al. (1996) The EMBO Journal 15(19):5256-5267, "Direct inhibition of the signaling functions of the mammalian target of rapamycin by the phosphoinositide 3-kinase inhibitors, wortmannin and LV294002".

CAS Registry No. 76780-41-1, 2 pages.

Canadian Intellectual Property Office acting as International Searching Authority, International Searching Authority, International Search Report prepared Apr. 28, 2008 for International Application No. PCT/CA2008/000045.

Canadian Intellectual Property Office acting as International Searching Authority, Written Opinion of the International Searching Authority prepared Apr. 28, 2008 for International Application No. PCT/CA2008/000045.

Chiang et al. (2007) Trends in Molecular Medicine 13:433-442, "Targeting the mTOR signaling network in cancer".

Chou et al. (1983) Trends in Pharm Sci 4:450-454, "Analysis of combined drug effects: a new look at a very old problem".

Chou (2006) Pharmacol Rev 58:621-681, "Theoretical Basis, Experimental Design, and Computerized Simulation of Synergism and Antagonism in Drug Combination Studies".

Choudhary et al. (1998) Journal of the Indian Chemical Society, 75, 392-394, "Structural Aspects of Morpholine-N-thiohydrazone Complexes with some Bivalent Metals".

Cully et al. (2006) Nature 6:184-192, "Beyond PTEN mutations: the PI3K pathway as an integrator of multiple inputs during tumorigenesis".

Daunis et al. (1970) Bull. Soc. Chim. Fr., No. 6:2289-2291, "Semicarbazones et thiosemicarbazones N-4 substituees de l'isatine".

Decaudin (2005) Int. J. Cancer 113:849-856, "In vivo efficacy of STI571 in xenografted human small cell lung cancer alone or combined with chemotherapy".

Dierks et al. (2001) Drug Metabolism and Disposition 29:23-29, "A method for the simultaneous evaluation of the activities of seven major human drug-metabolizing cytochrome P450S using an in vitro cocktail of probe substrates and fast gradient liquid chromatography tandem mass spectrometry".

Dwivedi et al. (1995) J. Indian Chem. Soc. 72:403-405, "Donor Behaviour of some Motpholine-N-thiohydrazoneswith some Bivalent Metal 'Ions".

Dziadulewicz et al. (2001) Bioorganic and Medicinal Organic Letters, 11, 705-709, "Design of Non-Peptide $CCK_2$ and $NK_1$ Peptidomimetics Using 1-(2-Nitrophenyl)thiosemicarbazide as a Novel Common Scaffold".

Eliel et al. (1994) A Wiley-Interscience Publication: Stereochemistry of Organic Compounds, ch.14:1119-1190, "Chirality in molecilles devoid of chiral centers".

Franke et al. (2006) The American Journal of Human Genetics 78:1011-1025, "Reconstruction of a functional human gene network, with an application for prioritizing positional candidate genes".

French et al. (1966) J Med Chem 9:585-589, "The carcinostatic activity of thiosemicarhazones of formyl heteroaromatic compounds. III. Primary correlation".

Granville et al. (2006) Clin Cancer Res 12(3):679-689, "Handicapping the race to develop inhibitors of the phosphoinositide 3-Kinase/Akt/Mammalian target of rapamycin pathway".

Gres et al. (1998) Pharmaceutical Research 15(5):726-733, "Correlation between oral drug absorption in humans, and apparent drug permeability in TC-7 cells, a human epithelial intestinal cell line: comparison with the parental caco-2 cell line".

Gururaja et al. (2006) Clin Cancer Res 12(12)3831-3842, "R-253 disrupts microtubule networks in multiple tumor cell lines".

Hennessy et al. (2005) Nature 4:988-1004, "Exploiting the PI3K/AKT pathway for cancer drug discovery".

Heinisch et al. (1972) Journal fur Prakt. Chemie. Band 314, 682-698, "Synthesis and Struktur substituierter Isatinthiosemicarbazone und — isothiosemicarbazone".

Ho Sui et al. (2005) Nucleic Acids Research 33(10)3154-3164, "oPOSSUM: identification of over-represented transcription factor binding sites in co-expressed genes".

The intersection of common genes was determined using GeneVenn (http://mcbc.usm.edu/genevenn/genevenn.htm).

Izzard et al. (1999) Cancer Research 59:2581-2586, "Competitive and noncompetitive inhibition of the DNA-dependent protein kinase".

Krause et al (2005) New England Journal of Medicine 353(2):172-187 "Tyrosine kinases as targets for cancer therapy".

Labisbal et al. (2000) Polyhedron, 19, 1255-1262, "Spectral and structural studies of metal complexes of isatin 3-hexamethyleneiminylthiosemicarbazone prepared electrochemically".

le Coutre et al. (1999) Jrnl National Cancer Institute 91(2):163-168, In vivo eradication of human BCR/ABL-Positive leukemia cells with an ABL kinase inhibitor.

Lev et al. (2005) Clinical Cancer Research 11:306-314, "Inhibition of platelet-derived growth factor receptor signaling restricts the growth of human breast cancer in the bone of nude mice".

Lievre et al. (2006) Cancer Res 66(8):3992-3995, "KRAS mutation status is predictive of response to cetuximab therapy in colorectal cancer".

Liscovitch et al. (2002) IDrugs 5(4):349-355, "Cancer multidrug resistance: A review of recent drug discovery research".

Lister et al. (1970) Journal of the Chemical Society, 1313-1315, "Potentially Chemotherapeutic Purine Analogues, Part V. Some Hydrazone Derivatives of Pyrazole-4,5-diones and their Cyclisation to Pyrazolo [3,4-e][1,2,4]triazines".

LoPiccolo et al. (2008) Drug Resistance Updates 11:32-50, "Targeting the PI3K/Akt/mTOR pathway: effective combinations and clinical considerations".

MAPK Antibody is used to control for loading and specificity of PTEN siRNA (data obtained from Cell Signaling Technology website, http://www.eellsignal.eom/produets/6251.html) 3 pages.

McNeill (1973) Antimicrobial Agents and Chemotherapy 4(2):105-108, "Inhibition of granulocyte-macrophage colony formation in vitro by substituted isatin thiosemicarbazones".

Manning (2009) Biochem Soc Trans 37:217-222, "A complex interplay between Akt, TSC2 and the two mTOR complexes" abstract.

Missbach (1996) Journal of Biological Chemistry 271, 13515-13522, "Thiazolidine Diones, Specific Ligands of the Nuclear Receptor Retinoid Z Receptor/Retinoid Acid Receptor-related Orphan Receptor $\alpha$ with Potent Antiarthritic Activity".

Monks et al. (1991) National Cancer Institute 83(11)757-766, "Feasibility of a high-flux anticancer drug screen using a diverse panel of cultured human tumor cell lines".

Morgan et al. (1983), International Journal of Applied Radiation and Isotopes, 34(11), 1501-1504, "Synthesis of [1-$^{14}$C]1,2-Cyclohexanedione bis(4-diethylenoxythiosemicarbazone) and Preliminary Biodistribution Studies of this Potential Antitumor Agent".

NSC No. 84442-R, National Cancer Institute, 5 pages.

O'Sullivan et al. (1963), Chemotherapia, 7, 17-26, "A Study of the Chemotherapeutic Activity of Isatin β-4',4'-Dialkylthiosemicarbazones against Ectromelia Infection".

O'Sullivan et al. (1963), International Congress of chemotherapy, (1), 879-883, "A Study of Isatin β-Thiosemicarbazone Derivatives in Relation to the Cytopathic Changes Produced by Type 1 and Type 2 Poliovirus on Embryonic Rabbit Kidney Cells in Tissue-Culture".

Pacifici et al. (1992) Clin Pharmacokinetics 23(6):449-468, "Methods of determining plasma and tissue binding of drugs. Pharmacokinetic consequences" abstract.

Pandyra et al. (2007) Jrnl Pharmacology and Experimental Therapeutics 322(1):123-132, "Combination silencer RNA (siRNA) targeting Bcl-2 antagonizes siRNA against thymidylate synthase in human tumor cell lines".

Peterson et al. (2000) Jrnl Biological Chemistry 275(10):7416-7423, FKBP12-Rapamycin-associated protein (FRAP) autophosphorylates at serine 2481 under translationally repressive conditions.

Plowman et al. (1994) DN&P. 7(6):334-339, "Receptor tyrosine kinases as targets for drug intervention".

Prakash et al. (1989) Indian Drugs 27(2), 106-110, "Synthesis and Screening of N-Morpholino/Piperidino Thiosemicarbazones as Potential Anitmicrobial Agents".

Rhodes et al. (2005) Nature Biotechnology 23(8):951-959, "Probabilistic model of the human protein-protein interaction network".

Riondel et al. (1988) Anticancer Research 8:387-390, "Antineoplastic activity of two taxol derivatives on an ovarian tumor xenografted into nude mice".
Sambuy et al. (2005) Cell Biology and Toxicology 21:1-26, "The Caco-2 cell line as a model of the intestinal barrier: infuence of cell and culture-related factors on Caco-2 cell functional characteristics".
Sarbassov et al. (2004) Current Biology 14:1296-1302, "Rictor, a novel binding partner of mTOR, defines a rapamycin-insensitive and raptor-independent pathway that regulates the cytoskeleton".
Scripture et al. (2006) Nature 6:546-558, "Drug interactions in cancer therapy".
Sebille (1990) Fundam Clin Pharmacol 4(S2):151s-161s, "Methods of drug protein binding determinations".
Seleem et al. (2002) Journal of the Serbian Chemical Society, 67(4), 243-256, "Thermodynamics of complexation of isatin-3-thiosemicarbazone (HIT) and other related derivatives with some metal ions".
Several mutations that abolish PI3-K activity have been described and are catalogued in the human protein mutation database MutDB (http://mutdb.org/).
Shaw et al. (2006) Nature 441:424-430, "Ras, PI(3)K and mTOR signalling controls tumour cell growth".
Sherman et al. (2007) BMC Bioinformatics 8:426-436, "DAVID Knowledgebase: a gene-centered database integrating heterogeneous gene annotation resources to facilitate high-throughput gene functional analysis".
Shridhar et al. (1987) Indian Journal of Chemistry 26B:596-598, "Synthesis & antiparasitic activity of some new 1-(6/7-Nitrobenzoxazin-3-yl)-4-substituted-3-thiosemicarbazides & 4-Disubstituted 3- (6-Acetylbenzoxazin3-one)thiosemicarbazones".
Simone (1996) Cecil Textbook of Medicine, $20^{th}$ Edition 1:1004-1010, "Part XIV Oncology: 154 Introduction".
Szakács et al. (2006) Nature Reviews Drug Discovery 5:219-234, "Targeting multidrug resistance in cancer".
Szakács et al. (2008) Drug Discovery Today 13(9/10):379-393, "The role of ABC transporters in drug absorption, distribution, metabolism, excretion and toxicity (ADME—Tox)".
Undevia et al. (2005) Nature Reviews 5:447-458, "Pharmacokinetic variability of anticancer agents".
Van den Bongard et al. (2000) Clinical Pharmacokinetics 39(5):345-367, "Pharmacokinetically Guided Administration of Chemotherapeutic Agents" abstract.
Varughese et al. (1984) Drugs under Experimental and Clinical Research 10(2), 67-74, "A Biodistribution Study of 1-$^{14}$C-1,2-Cyclohexanedione Bis(4-Diethylenoxythiosemicarbazone), A Potential Antitumour Agent".
Venkatakrishnan et al. (2001) J Clin Pharmacol 41:1149-1179, "Human drug metabolism and the cytochromes P450: application and relevance of in vitro models".
Winkelmann et al. (1987) Drug Res 37(1):647-661, "Antimalarial and Anticoccidial Activity of 3- Ary1-7-chloro-3,4-dihydroacridine-1 ,9-(2H, 1OH)-diones".
Wolber et al. (2006) Methods in Enzymology 410:28-57, "the agilent in situ-synthesized microarray platform".
Yuan et al. (2004) Blood 104:1450-1458, "Novel di-2-pyridyl-derived iron chelators with marked and selective antitumor activity: in vitro and in vivo assessment".
Zhou (2008) Xenobiotica 38(7-8):802-832, "Structure, function and regulation of P-glycoprotein and its clinical relevance in drug disposition".
Zwick et al (2002) Trends in Molecular Medicine 8(1):17-23, "Receptor tyrosine kinases as targets for anticancer drugs".
Canadian Intellectual Property Office acting as International Searching Authority, International Search Report and Written Opinion prepared Mar. 2, 2009 for International Application No. PCT/CA2008/002293, 12 pages.
Canadian Intellectual Property Office acting as International Searching Authority, International Search Report prepared Sep. 22, 2009 and Written Opinion prepared Oct. 28, 2009 for International Application No. PCT/CA2009/001004, 15 pages.
Akashi et al. (2008) Br J Cancer 98: 749-755, "Enhancement of the antitumor activity of ionising radiation by nimotuzumab, a humanized monoclonal antibody to the epidermal growth factor receptor, in non-small cell lung cancer cell lines of differing epidermal growth factor receptor status" abstract.
Akcakanat et al. (2007) Biochem Biophys Res Commun 362: 330-333, "Rapamycin regulates the phosphorylation of rictor." abstract.
Alessi et al. (1997) Curr Biol 7: 776-789, "3-Phosphoinositide-dependent protein kinase-1 (PDK1): structural and functional homology with the Drosophila DSTPK61 kinase" abstract.
Alessi et al. (1997) Curr Biol 7: 261-269, "Characterization of a 3-phosphoinositide-dependent protein kinase which phosphorylates and activates protein kinase Balpha" abstract.
Altomare et al. (2004) Oncogene 23: 5853-5857, "AKT and mTOR phosphorylation is frequently detected in ovarian cancer and can be targeted to disrupt ovarian tumor cell growth" abstract.
Altomare et al. (2005) Oncogene 24: 7455-7464, "Perturbations of the AKT signaling pathway in human cancer" abstract.
Ananthanarayanan et al. (2007) J Biol Chem 282: 36634-36641, "Live-cell molecular analysis of Akt activation reveals roles for activation loop phosphorylation" abstract.
Beeram et al. (2005) J Clin Onco 23: 6771-6790, "Raf: a strategic target for therapeutic development against cancer" abstract.
Bellacosa et al. (2005) Adv Cancer Res 94: 29-86, "Activation of AKT kinases in cancer: implications for therapeutic targeting" abstract.
Bjornsti et al. (2004) Nat Rev Cancer 4: 335-348 Ref ID: 154, "The TOR pathway: a target for cancer therapy" abstract.
Bondar et al. (2002) Mol Cancer Ther 1: 989-997, "Inhibition of the phosphatidylinositol 3'-kinase-AKT pathway induces apoptosis in pancreatic carcinoma cells in vitro and in vivo" abstract.
Bose et al. (2009) Exp Cell Res 315: 649-658, "The ErbB kinase domain: structural perspectives into kinase activation and inhibition" abstract.
Braun et al. (2008) Clin Cancer Res 14: 2249-2252, "Targeting Ras in myeloid leukemias" abstract.
Brognard et al. (2001) Cancer Res 61: 3986-3997, "Akt/protein kinase B is constitutively active in non-small cell lung cancer cells and promotes cellular survival and resistance to chemotherapy and radiation" abstract.
Buck et al. (2006) Mol Cancer Ther 5: 2676-2684, "Rapamycin synergizes with the epidermal growth factor receptor inhibitor erlotinib in non-small-cell lung, pancreatic, colon, and breast tumors" abstract.
Caron et al. (2005) Mol Cancer Ther 4: 257-270, "Activated forms of H-RAS and K-RAS differentially regulate membrane association of PI3K, PDK-1, and AKT and the effect of therapeutic kinase inhibitors on cell survival" abstract.
Castagnola et al. (2005) Biochim Biophys Acta 1756: 115-125, "Mutant KRAS, chromosomal instability and prognosis in colorectal cancer" abstract.
Castillo et al. (2004) Cancer Res 64: 2782-2792, "Preferential inhibition of Akt and killing of Akt-dependent cancer cells by rationally designed phosphatidylinositol ether lipid analogues.".
Castro-Carpeno et al. (2008) Clin Transl Onco/1 0: 6-13, "EGFR and colon cancer: a clinical view" abstract.
Cespedes et al. (2006) Carcinogenesis 27: 2190-2200, "K-ras Asp12 mutant neither interacts with Raf, nor signals through Erk and is less tumorigenic than K-ras Va112" abstract.
Chadha et al. (2006) Ann Surg Oncol 13: 933-939, "Activated Akt and Erk expression and survival after surgery in pancreatic carcinoma" abstract.
Chiang GG, Abraham RT (2007) Trends Mol Med 13: 433-442, "Targeting the mTOR signaling network in cancer" abstract.
Chau et al. (2009) Br J Cancer 100:1704-1719, "Treatment in advanced colorectal cancer: what, when and how?" abstract.
Chen et al. (2001) J Biol Chem 276: 31858-31862, "Regulation of Akt/PKB activation by tyrosine phosphorylation" abstract.
Cheng et al. (1992) Proc Natl Acad Sci U S A 89: 9267-9271, "AKT2, a putative oncogene encoding a member of a subfamily of protein-serine/threonine kinases, is amplified in human ovarian carcinomas" abstract.
Cheng et al. (1996) Proc Natl Acad Sci U S A 93: 3636-3641, "Amplification of AKT2 in human pancreatic cells and inhibition of AKT2 expression and tumorigenicity by antisense RNA" abstract.

Cheng et al. (2005) Oncogene 24: 7482-7492, "The Akt/PKB pathway: molecular target for cancer drug discovery" abstract.
Clark et al. (2002) Mol Cancer Ther 1: 707-717, "Constitutive and inducible Akt activity promotes resistance to chemotherapy, trastuzumab, or tamoxifen in breast cancer cells" abstract.
Copp et al. (2009) Cancer Res 69: 1821-1827, "TORC-specific phosphorylation of mammalian target of rapamycin (mTOR): phospho-Ser2481 is a marker for intact mTOR signaling complex 2" abstract.
Dacic, S. (2008) Adv Anat Pathol 15: 241-247, "EGFR assays in lung cancer" abstract.
Datta et al. (1999) Genes Dev 13: 2905-2927, "Cellular survival: a play in three Akts" abstract.
de Gunzburg, J. (1999) Cell Bioi Toxicol 15: 345-358, "Proteins of the Ras pathway as novel potential anticancer therapeutic targets" abstract.
Defeo-Jones et al. (2005) Mol Cancer Ther 4:271-279, "Tumor cell sensitization to apoptotic stimuli by selective inhibition of specific Akt/PKB family members" abstract.
DeGraffenried et al. M (2004) Ann Oncol 15: 1510-1516, "Reduced PTEN expression in breast cancer cells confers susceptibility to inhibitors of the PI3 kinase/Akt pathway" abstract.
Deramaudt T, Rustgi AK (2005) Biochim Biophys Acta 1756:97-101, "Mutant KRAS in the initiation of pancreatic cancer".
Dobashi et al. (2009) Cancer 115: 107-118, "Critical and diverse involvement of Akt/mammalian target of rapamycin signaling in human lung carcinomas" abstract.
Doody et al. (2007) Mol Cancer Ther 6: 2642-2651, "Inhibitory activity of cetuximab on epidermal growth factor receptor mutations in non small cell lung cancers" abstract.
Dowling et al. (2009) BioDrugs 23: 77-91, "Current status and challenges associated with targeting mTOR for cancer therapy" abstract.
Downward, J. (2003) Nat Rev Cancer 3: 11-22, "Targeting RAS signalling pathways in cancer therapy" abstract.
Du K, Tsichlis PN (2005) Oncogene 24: 7401-7409, "Regulation of the Akt kinase by interacting proteins" abstract.
El Rayes et al. (2006) Cancer Res 66: 10553-10559, "Potentiation of the effect of erlotinib by genistein in pancreatic cancer: the role of Akt and nuclear factor-kappaB" abstract.
Ellis et al. (2000) Cell Signal 12: 425-434, "The importance of being K-Ras" abstract.
Engelman et al. (2008) Nat Med 14: 1351-1356, "Effective use of PI3K and MEK inhibitors to treat mutant Kras G12D and PIK3CA H1047R murine lung cancers" abstract.
Engelman et al. (2008) Clin Cancer Res 14: 2895-2899, "Mechanisms of acquired resistance to epidermal growth factor receptor tyrosine kinase inhibitors in non-small cell lung cancer" abstract.
Engelman, JA (2009) Nat Rev Cancer 9: 550-562, "Targeting PI3K signalling in cancer: opportunities, challenges and limitations" abstract.
Fakih M (2008) Curr Treat Options Oncol 9: 357-374, "The role of targeted therapy in the treatment of advanced colorectal cancer" abstract.
Feldman et al. (2009) PLoS Biol 7:e38, "Active-site inhibitors of mTOR target rapamycin-resistant outputs of mTORC1 and mTORC2" abstract.
Fischer et al. (2007) Cancer Treat Rev 33: 391-406, "Targeting receptor tyrosine kinase signalling in small cell lung cancer (SCLC): what have we learned so far?" abstract.
Fotiadou et al. (2007) Mol Cell Biol 27: 6742-6755, "Wild-type NRas and KRas perform distinct functions during transformation" abstract.
Franke et al. (2003) Oncogene 22: 8983-8998, "PI3K/Akt and apoptosis: size matters" abstract.
Friday et al. (2005) Biochim Biophys Acta 1756: 127-144, "K-ras as a target for cancer therapy" abstract.
Fukui et al. (2008) Gen Thorac Cardiovasc Surg 56: 97-103, "Mutations in the epidermal growth factor receptor gene and effects of EGFR-tyrosine kinase inhibitors on lung cancers" abstract.
Furukawa, T. (2008) J Gastroenterol 43: 905-911, "Molecular targeting therapy for pancreatic cancer: current knowledge and perspectives from bench to bedside".
Gadducci et al. (2008) Gynecol Endocrinol 24: 239-249, "Molecular target therapies in endometrial cancer: from the basic research to the clinic" abstract.
Garassino et al. (2009) Anticancer Res 29: 2691-2701, "Biological and clinical features in predicting efficacy of epidermal growth factor receptor tyrosine kinase inhibitors: a systematic review and meta-analysis" abstract.
Gazdar, AF (2009) Oncogene 28 Suppll: S24-S31, "Activating and resistance mutations of EGFR in non-small-cell lung cancer: role in clinical response to EGFR tyrosine kinase inhibitors" abstract.
Granville et al. (2006) Clin Cancer Res 12: 679-689, "Handicapping the race to develop inhibitors of the phosphoinositide 3-kinase/Akt/mammalian target of rapamycin pathway" abstract.
Gridelli et al. (2008) Oncologist 13: 139-147, "The potential role of mTOR inhibitors in non-small cell lung cancer".
Guerrero et al. (2002) FASEB J 16: 1642-1644, "Codon 12 and codon 13 mutations at the K-ras gene induce different soft tissue sarcoma types in nude mice" abstract.
Guertin et al. (2007) Cancer Cell 12: 9-22, "Defining the role of mTOR in cancer" abstract.
Guzeloglu et al. (2004) Biol Reprod 71: 714-721, "In vivo and in vitro regulation of Akt activation in human endometrial cells is estrogen dependent" abstract.
Hartmann et al. (2006) Clin Cancer Res 12: 3019-3027, "Phosphatidylinositol 3'-kinase/AKT signaling is activated in medulloblastoma cell proliferation and is associated with reduced expression of PTEN" abstract.
Hay, N. (2005) Cancer Cell 8: 179-183, "The Akt-mTOR tango and its relevance to cancer".
Heinemann et al. (2009) Cancer Treat Rev 35:262-271, "Clinical relevance of EGFR- and KRAS-status in colorectal cancer patients treated with monoclonal antibodies directed against the EGFR" abstract.
Helfrich et al. (2006) Clin Cancer Res 12: 7117-7125, "Antitumor activity of the epidermal growth factor receptor (EGFR) tyrosine kinase inhibitor gefitinib (ZD1839, Iressa) in non-small cell lung cancer cell lines correlates with gene copy number and EGFR mutations but not EGFR protein levels" abstract.
Hennessy et al. (2005) Nat Rev Drug Discov 4: 988-1004, "Exploiting the PI3K/AKT pathway for cancer drug discovery" abstract.
Hirsch et al. (2006) J Clin Oncol 24: 5034-5042, "Molecular predictors of outcome with gefitinib in a phase III placebo-controlled study in advanced non-small-cell lung cancer" abstract.
Holland et al. (2000) Nat Genet 25: 55-57, "Combined activation of Ras and Akt in neural progenitors induces glioblastoma formation in mice" abstract.
Houlston, RS (2001) Mol Pathol 54: 206-214, "What we could do now: molecular pathology of colorectal cancer" abstract.
Huang et al. (2004) Cancer Res 64: 5355-5362, "Dual-agent molecular targeting of the epidermal growth factor receptor (EGFR): combining anti-EGFR antibody with tyrosine kinase inhibitor" abstract.
Huang et al. (2006) Mol Cell Proteomics 5: 1045-1053, "Interdomain conformational changes in Akt activation revealed by chemical cross-linking and tandem mass spectrometry" abstract.
Huang et al. (2009) Biochem Soc Trans 37: 217-222, "A complex interplay between Akt, TSC2 and the two mTOR complexes" abstract.
Huang et al. (2009) J Formos Med Assoc 108: 180-194, "Induction of Akt activity by chemotherapy confers acquired resistance" abstract.
Hynes et al. (2009) Curr Opin Cell Biol 21: 177-184, "ErbB receptors and signaling pathways in cancer" abstract.
Ikeda et al. (2007) Pathol Int 57: 268-275, "Correlation between EGFR gene mutation pattern and Akt phosphorylation in pulmonary adenocarcinomas" abstract.
Itoh et al. (2002) Cancer 94: 3127-3134, "Phosphorylation of Akt/PKB is required for suppression of cancer cell apoptosis and tumor progression in human colorectal carcinoma" abstract.
Jacinto et al. (2006) Cell 127: 125-137, "SIN1/MIP1 maintains rictor-mTOR complex integrity and regulates Akt phosphorylation and substrate specificity" abstract.
Janmaat et al. (2003) Clin Cancer Res 9: 2316-2326, "Response to epidermal growth factor receptor inhibitors in non-small cell lung cancer cells: limited antiproliferative effects and absence of apoptosis associated with persistent activity of extracellular signal-regulated kinase or Akt kinase pathways" abstract.
Janmaat et al. (2006) Int J Cancer 118: 209-214, "Enhanced cytotoxicity induced by gefitinib and specific inhibitors of the Ras or phosphatidyl inositol-3 kinase pathways in non-small cell lung cancer cells" abstract.
Janne, PA (2008) Lung Cancer 60 Suppl 2: S3-S9, "Challenges of detecting EGFR T790M in gefitinib/erlotinib-resistant tumours" abstract.
Jetzt et al. (2003) Cancer Res 63: 6697-6706, "Adenoviral-mediated expression of a kinase-dead mutant of Akt induces apoptosis selectively in tumor cells and suppresses tumor growth in mice" abstract.
Ji et al. (2007) J Biol Chern 282: 14048-14055, "Oncogenic KRAS activates hedgehog signaling pathway in pancreatic cancer cells" abstract.
Jiang et al. (2000) Mol Cell Biol 20: 139-148, "The phosphoinositide 3-OH kinase/AKT2 pathway as a critical target for farnesyltransferase inhibitor-induced apoptosis" abstract.
Jiang et al. (2008) Drug Resist Updat 11: 63-76, "Role of mTOR in anticancer drug resistance: perspectives for improved drug treatment" abstract.
Jiang et al. (2009) Cancer 115: 3609-3617, "Assessment of K-ras mutation: a step toward personalized medicine for patients with colorectal cancer" abstract.
Jiang et al. (2009) Adv Cancer Res 102: 19-65, "PI3K/PTEN signaling in angiogenesis and tumorigenesis" abstract.
Jimeno et al. (2009) Cancer J 15: 110-113, "KRAS mutations and susceptibility to cetuximab and panitumumab in colorectal cancer" abstract.
Jimeno et al. (2009) J Clin Oncol 27: 1130-1136, "KRAS mutations and sensitivity to epidermal growth factor receptor inhibitors in colorectal cancer: practical application of patient selection" abstract.
John et al. (2009) Oncogene 28 Suppl 1: S14-S23, "Overview of molecular testing in non-small-cell lung cancer: mutational analysis, gene copy number, protein expression and other biomarkers of EGFR for the prediction of response to tyrosine kinase inhibitors" abstract.
Kandasamy et al. (2002) Cancer Res 62: 4929-4937, "Role of the phosphatidylinositol 3'-kinase/PTEN/Akt kinase pathway in tumor necrosis factor-related apoptosis-inducing ligand-induced apoptosis in non-small cell lung cancer cells" abstract.
Kang et al. (2008) Int J Gynecol Cancer 18: 1339-1343, "Mutual exclusiveness between PIK3CA and KRAS mutations in endometrial carcinoma" abstract.
Kim et al. (2002) J Biochem Mol Biol 35: 106-115, "Akt: versatile mediator of cell survival and beyond" abstract.
Kimura et al. (2007) Cancer Sci 98: 12751280, "Antibody-dependent cellular cytotoxicity of cetuximab against tumor cells with wild-type or mutant epidermal growth factor receptor" abstract.
Klein et al. (2009) Curr Opin Cell Bioi 21 : 185-193, "Targeting the EGFR and the PKB pathway in cancer" abstract.
Kobayashi et al. (2005) N Engl J Med 352: 786792, "EGFR mutation and resistance of non-small-cell lung cancer to gefitinib" abstract.
Konstantinopoulos et al. (2007) Nat Rev Drug Discov 6: 541-555, "Post-translational modifications and regulation of the RAS superfamily of GTPases as anticancer targets" abstract.
Kurman et al. (2008) Int J Gynecol Pathol 27: 151-160, "Pathogenesis of ovarian cancer: lessons from morphology and molecular biology and their clinical implications" abstract.
Ladanyi et al. (2008) Mod Pathol 21 Suppl 2: S16-S22, "Lung adenocarcinoma: guiding EGFR-targeted therapy and beyond" abstract.
Laurent-Puig et al. (2008) Curr Opin Onco/20: 454-458, "Lessons from Tarceva in pancreatic cancer: where are we now, and how should future trials be designed in pancreatic cancer?" abstract.
Laurent-Puig et al. (2009) Clin Cancer Res 15: 1133-1139, "Mutations and response to epidermal growth factor receptor inhibitors" abstract.
Lee et al. (2005) Clin Cancer Res 11: 6065-6074, "Response of non-small cell lung cancer cells to the inhibitors of phosphatidylinositol 3-kinase/Akt- and MAPK kinase 4/c-Jun NH2-terminal kinase pathways: an effective therapeutic strategy for lung cancer" abstract.
Lee et al. (2008) Int J Cancer 122: 2380-2384, "Akt1 inhibition by RNA interference sensitizes human non-small cell lung cancer cells to cisplatin" abstract.
Legrier et al. (2007) Cancer Res 67: 11300-11308, "Targeting protein translation in human non small cell lung cancer via combined MEK and mammalian target of rapamycin suppression" abstract.
Lin et al. (2005) Br J Cancer 93: 1372-1381, "Elevated phosphorylation and activation of PDK-1/AKT pathway in human breast cancer" abstract.
Linardou et al. (2008) Lancet Oneol 9: 962-972, "Assessment of somatic k-RAS mutations as a mechanism associated with resistance to EGFR-targeted agents: a systematic review and meta-analysis of studies in advanced non-small-cell lung cancer and metastatic colorectal cancer" abstract.
Liu et al. (2007) Clin Cancer Res 13: 67886795, "Relationship of EGFR mutations, expression, amplification, and polymorphisms to epidermal growth factor receptor inhibitors in the NCI60 cell lines." abstract.
Liu et al. (2008) PLoS One 3: e2850, "K-ras/PI3K-Akt signaling is essential for zebrafish hematopoiesis and angiogenesis" abstract.
Liu et al. (2009) Nat Rev Drug Discov 8 627-644, "Targeting the phosphoinositide 3-kinase pathway in cancer"abstract.
LoPiccolo et al. (2008) Drug Resist Updat 11: 32-50, "Targeting the PI3K/Akt/mTOR pathway: effective combinations and clinical considerations" abstract.
Mahoney et al. (2009) Br J Cancer 100: 370-375, "LKB1/KRAS mutant lung cancers constitute a genetic subset of NSCLC with increased sensitivity to MAPK and mTOR signalling inhibition" abstract.
Manning et al. (2007) Cell 129: 1261-1274 Ref ID: 125, "AKT/PKB signaling: navigating downstream" abstract.
Martelli et al. (2006) Leukemia 20: 911-928, "Phosphoinositide 3-kinase/Akt signaling pathway and its therapeutical implications for human acute myeloid leukemia" abstract.
Massion et al. (2004) Am J Respir Crit Care Med 170: 1088-1094, "Early involvement of the phosphatidylinositol 3-kinase/Akt pathway in lung cancer progression" abstract.
Masure et al. (1999) Eur J Biochem 265: 353-360, "Molecular cloning, expression and characterization of the human serine/threonine kinase Akt-3" abstract.
McCubrey et al. (2008) Adv Enzyme Regul 48: 113-135, "Alteration of Akt activity increases chemotherapeutic drug and hormonal resistance in breast cancer yet confers an achilles heel by sensitization to targeted therapy" abstract.
Memmott (2009) Cell Signal 21: 656-664, "Akt-dependent and -independent mechanisms of mTOR regulation in cancer" abstract.
Meric-Bernstam et al. (2009) J Clin Oncol 27: 2278-2287, "Targeting the mTOR signaling network for cancer therapy" abstract.
Minaguchi et al. (2007) Cancer Lett 248: 112-122, "Combined phospho-Akt and PTEN expressions associated with post-treatment hysterectomy after conservative progestin therapy in complex atypical hyperplasia and stage Ia, G1 adenocarcinoma of the endometrium" abstract.
Morgensztern et al. (2005) Anticancer Drugs 16: 797-803, "PI3K/Akt/mTOR pathway as a target for cancer therapy" abstract.
Nelson et al. (2007) Prostate Cancer Prostatic Dis 10: 331-339, "Inhibition of Akt pathways in the treatment of prostate cancer".
Normanno et al. (2006) Gene 366: 2-16, "Epidermal growth factor receptor (EGFR) signaling in cancer" abstract.
Noske et al. (2007) Cancer Lett 246: 190-200, "Specific inhibition of AKT2 by RNA interference results in reduction of ovarian cancer cell proliferation: increased expression of AKT in advanced ovarian cancer" abstract.
Oehler-Janne et al. (2008) Biochem Biophys Res Commun 375: 399-404, "Temperature sensitivity of phospho-Ser(473)-PKB/AKT" abstract.
Okudela et al. (2004) Am J Pathol 164: 91-100, "K-ras gene mutation enhances motility of immortalized airway cells and lung adenocarcinoma cells via Akt activation: possible contribution to non-invasive expansion of lung adenocarcinoma" abstract.
Ono et al. (2006) Clin Cancer Res 12: 7242-7251, "Molecular mechanisms of epidermal growth factor receptor (EGFR) activation and response to gefitinib and other EGFR-targeting drugs" abstract.

Pao, W (2006) Cancer Chemother Pharmacol 58 Suppl: sll-s15, “Defining clinically relevant molecular subsets of lung cancer” abstract.
Pao et al. (2005) PLoS Med 2: e73, “Acquired resistance of lung adenocarcinomas to gefitinib or erlotinib is associated with a second mutation in the EGFR kinase domain” abstract.
Parikh et al. (2007) Cancer Res 67: 7139-7146, “Oncogenic NRAS, KRAS, and HRAS exhibit different leukemogenic potentials in mice” abstract.
Papadimitrakopoulou et al. (2006) J Thorac Oncol 1: 749-751, “The Akt/mTOR and mitogen-activated protein kinase pathways in lung cancer therapy” abstract.
Plesec et al. (2009) Adv Anat Pathol 16: 196-203, “KRAS mutation testing in colorectal cancer” abstract.
Pretlow et al. (2005) Biochim Biophys Acta 1756: 83-96, “Mutant KRAS in aberrant crypt foci (ACF): initiation of colorectal cancer?” abstract.
Raponi et al. (2008) Curr Opin Pharmacol 8: 413-418, “KRAS mutations predict response to EGFR inhibitors” abstract.
Riely, GJ (2008) Lung Cancer 60 Suppl 2: S19-S22, “The use of first-generation tyrosine kinase inhibitors in patients with NSCLC and somatic EGFR mutations” abstract.
Riely, GJ (2008) J Thorac Oncol 3: S146-S149, “Second-generation epidermal growth factor receptor tyrosine kinase inhibitors in non-small cell lung cancer” abstract.
Riely et al. (2009) Proc Am Thorac Soc 6: 201-205, “KRAS mutations in non-small cell lung cancer” abstract.
Rong et al. (2001) J Med Chem 44: 898-908, “Molecular modeling studies of the Akt PH domain and its interaction with phosphoinositides” abstract.
Rosner et al. (2008) Mutat Res 659: 284-292, “The mTOR pathway and its role in human genetic diseases” abstract.
Rosti et al. (2006) Ann Oncol 17 Suppl 5: v99-102, “Chemotherapy advances in small cell lung cancer” abstract.
Ruggeri et al. (1998) Mol Carcinog 21: 81-86, “Amplification and overexpression of the AKT2 oncogene in a subset of human pancreatic ductal adenocarcinomas” abstract.
Ruggero et al. (2005) Oncogene 24: 7426-7434, “The Akt of translational control” abstract.
Sabatini, DM (2006) Nat Rev Cancer 6: 729-734, “mTOR and cancer: insights into a complex relationship” abstract.
Saif et al. (2009) Clin Adv Hematol Onco/7: 45-53, 64, “K-ras mutations in colorectal cancer: a practice changing discovery” abstract.
Sarbassov et al. (2004) Curr Biol 14: 1296-1302, “Rictor, a novel binding partner of mTOR, defines a rapamycin-insensitive and raptor-independent pathway that regulates the cytoskeleton”.
Sarbassov et al. (2005) Science 307: 1098-1101, “Phosphorylation and regulation of Akt/PKB by the rictor-mTOR complex” abstract.
Schneider et al. (2003) Mol Cancer 2: 15, “Genetic alterations in pancreatic carcinoma” abstract.
Schubbert et al. (2007) Nat Rev Cancer 7: 295-308, “Hyperactive Ras in developmental disorders and cancer” abstract.
Seeliger et al. (2007) Cancer Metastasis Rev 26: 611-621, “Role of mTOR in solid tumor systems: a therapeutical target against primary tumor growth, metastases, and angiogenesis” abstract.
Sequist, LV (2008) J Thorac Oncol 3: S143-S145, “First-generation epidermal growth factor receptor tyrosine kinase inhibitors in EGFR mutation: positive non-small cell lung cancer patients” abstract.
Sequist et al. (2008) Annu Rev Med 59:429-442, “EGFR tyrosine kinase inhibitors in lung cancer: an evolving story” abstract.
Shaw et al. (2006) Nature 441: 424-430, “Ras, PI(3)K and mTOR signalling controls tumour cell growth” abstract.
She et al. (2008) PLoS One 3: e3065, “Breast tumor cells with PI3K mutation or HER2 amplification are selectively addicted to Akt signaling” abstract.
Shtilbans et al. (2008) Ann Diagn Pathol 12: 153-160, “Current overview of the role of Akt in cancer studies via applied immunohistochemistry” abstract.
Siegel-Lakhai et al. (2005) Oncologist 10: 579-589, “Current knowledge and future directions of the selective epidermal growth factor receptor inhibitors erlotinib (Tarceva) and gefitinib (Iressa)” abstract.
Smakman et al. (2005) Biochim Biophys Acta 1756: 103-114, “Control of colorectal metastasis formation by K-Ras” abstract.
Spano et al. (2008) Crit Rev Oncol Hematol 66: 21-30, “Potential predictive markers of response to EGFR-targeted therapies in colorectal cancer” abstract.
Steelman et al. (2008) Leukemia 22: 686-707, “Contributions of the Raf/MEK/ERK, PI3K/PTEN/Akt/mTOR and Jak/STAT pathways to leukemia” abstract.
Steiner et al. (2007) Clin Cancer Res 13: 1540-1551, “Tumor growth inhibition with cetuximab and chemotherapy in non-small cell lung cancer xenografts expressing Wild-type and mutated epidermal growth factor receptor” abstract.
Stintzing et al. (2009) Dtsch Arztebllnt 106: 202-206, “The treatment of colorectal carcinoma with monoclonal antibodies: the importance of KRAS mutation analysis and EGFR status” abstract.
Strimpakos et al. (2009) Cancer Treat Rev 35: 148-159, “The role of mTOR in the management of solid tumors: an overview” abstract.
Suda et al. (2009) J Thorac Oncol 4: 1-4, “EGFR T790M mutation: a double role in lung cancer cell survival?” abstract.
Tang et al. (2006) Oncol Rep 15: 855-859, “PTEN sensitizes epidermal growth factor-mediated proliferation in endometrial carcinoma cells” abstract.
Teachey et al. (2009) Br J Haematol 145: 569-580, “Mammalian target of rapamycin inhibitors and their potential role in therapy in leukaemia and other haematological malignancies” abstract.
Testa et al. (2005) Oncogene 24: 7391-7393, “AKT signaling in normal and malignant cells” abstract.
Tomida et al. (2005) Cancer Sci 96: 63-68, “Throwing new light on lung cancer pathogenesis: updates on three recent topics” abstract.
Tzeng et al. (2007) J Surg Res 143: 20-26, “EGFR genomic gain and aberrant pathway signaling in pancreatic cancer patients” abstract.
Uramoto et al. (2007) Br J Cancer 96: 857-863, “Which biomarker predicts benefit from EGFR-TKI treatment for patients with lung cancer?” abstract.
Vanhaesebroeck et al. (2000) Biochem J 346 Pt 3: 561-576, “The PI3K-PDK1 connection: more than just a road to PKB” abstract.
Vivanco et al. (2002) Nat Rev Cancer 2: 489-501, “The phosphatidylinositol 3-Kinase AKT pathway in human cancer” abstract.
Walther et al. (2009) Nat Rev Cancer 9: 489-499, “Genetic prognostic and predictive markers in colorectal cancer” abstract.
Wang et al. (2008) Cancer Res 68: 7409-7418, “Enhancing mammalian target of rapamycin (mTOR)-targeted cancer therapy by preventing mTOR/raptor inhibition-initiated, mTOR/rictor-independent Akt activation” abstract.
Weng et al. (2009) Cancer Lett 273: 257-265, “Implication of the Akt2/survivin pathway as a critical target in paclitaxel treatment in human ovarian cancer cells” abstract.
Wong, KK (2008) Lung Cancer 60 Suppl 2: S10-S18, “Searching for a magic bullet in NSCLC: the role of epidermal growth factor receptor mutations and tyrosine kinase inhibitors”.
Yamamoto et al. (2008) Cancer Res 68: 6913-6921, “PIK3CA mutations and copy number gains in human lung cancers” abstract.
Yang et al. (2002) Nat Struct Biol 9: 940-944, “Crystal structure of an activated Akt/protein kinase B ternary complex with GSK3-peptide and AMP-PNP” abstract.
Yap et al. (2008) Curr Opin Pharmacol 8: 393-412, “Targeting the PI3K-AKT-mTOR pathway: progress, pitfalls, and promises” abstract.
Yuan et al. (2000) Oncogene 19: 2324-2330, “Frequent activation of AKT2 and induction of apoptosis by inhibition of phosphoinositide-3-OH kinase/Akt pathway in human ovarian cancer” abstract.
Zhang et al. (2005) Proc Natl Acad Sci U S A 102: 14605-14610, “Identification of K-ras as the major regulator for cytokine-dependent Akt activation in erythroid progenitors in vivo” abstract.
Zhang et al. (2007) Nat Med 13: 1114-1119, “Molecular imaging of Akt kinase activity” abstract.
Zhang et al. (2007) J Med Genet 44: 166-172, “Somatic mutations of the epidermal growth factor receptor and non-small-cell lung cancer” abstract.
Zwick et al. (2002) Trends Mol Med 8:17-23, “Receptor tyrosine kinases as targets for anticancer drugs” abstract.

Supplementary European Search Report for European Application No. 08865722 mailed Feb. 9, 2012.
Sugimoto et al., “Activation of Dithiocarbamate by 2-Halothiazolium Salts”, 1988, J. Org. Chem., 53, pp. 2263-2267.
Heinisch et al., “Synthesen und Reaktionen von Pyridazinderviaten”, 1973, Monatshefte fur Chemie 104, pp. 1372-1382.
Braun et al., “4,5-Diacylpyridazine: Synthese und Umsetzung zu 1,4-Diaryl- bzw. 1,4-Dialkyl-pyridazino [4,5-d] pyridazinen” 1978, Monatshefte fur Chemie 109, pp. 63-71.
Rusinov et al., “New reaction of 3,6-bis(2-pyridyl)-1,2,4,5-tetrazine with anhydro base of 1,2,3-trimethylquinoxalinium and intramolecular aminolysis of the resulting azomethine”, 1981, (abstract).
Suzuki et al., Preparation of diphenylmethylimine derivatives as antiinflammatories, antitumors, and lipoxygenase and cyclooxygenase inhibitors, 1987 (abstract).
West et al., “Copper(II) complexes of 2-formyl-, 2-acetyl- and 2-benzoy-pyridine N(4)-phenyl-, N(4)-o-methoxyphenyl-, N(4)-p-methoxy-phenyl-and N(4)-p-nitrophenylthiosemicarbazones”, 1996, Transition Met. Chem., 21, pp. 213-218.
West et al., “Copper(II) complexes of 2-formyl-, 2-acetyl- and 2-benzoylpyridine N(4)-o-, N(4)-m-, N(4)-p-chlorophenylthiosemicarbazones”, 1996, Transition Met. Chem., 21, pp. 52-57.
Kalinowski et al., “Design, Synthesis, and Characterization of Novel Iron Chelators: Structure-Activity Relationships of the 2-Benzoylpyridine Thiosemicarbazone Series and Their 3-Nitrobenzoyl Analogues as Potent Antitumor Agents”, 2007, J. Med. Chem., 50, pp. 3716-3729.
Wang et al., Preparation of heteroaryl substituted hydrazinecarbothioamide compounds for treatment of cancer, 2007 (abstract).
West et al., “Copper(II) complexes of 2-formyl-, 6-methyl-2-formyl- and 2-benzoylpyridine N(4)-(2- methylpyridinyl)-,N(4)-(2-ethylpyridiny1)-and N(4)-methyl(2-ethylpyridinyl) thiosemicarbazones”, 1996, Transition Met. Chem., 21, pp. 289-295.
Agrawal et al., “Potential Antitumor Agents. 11. Inhibitors of Alkaline Phosphatase, an Enzyme Involved in the Resistance of Neoplastic Cell to 6-Thiopurines”, 1974, Journal of Medicinal Chemistry, vol. 17, No. 9, pp. 934-938.
Miller III, et al., “The Cytotoxicity of Copper(II) Complexes of 2-Acetyl-Pyridyl-N-Substituted Thiosemicarbazones”, 1998, Anticancer Research 18, pp. 4131-4140.
Easmon et al., “Synthesis and Antiviral Activity of Thiosemicarbazone Derivatives of Pyridazinecarbaldehydes and Alkyl Pyridazinyl Ketones”, 1989, Arzneim-Forsch/Drug Res. 39 (II), No. 10.
Europe Application No. 08700510.4-2117 Examination Report mailed Feb. 22, 2012.
Chemcats record, CAS Registry No. 903274-24-8, 903180-32-5, 901391-84-2, 901360-35-8, 901360-08-5, 901349-50-6, 901348-18-3, 901329-97-3, 901285-15-2, 847046-07-5, 802269-45-0, 733793-43-6, 732992-68-6, 732257-35-1, 519151-42-9, 501650-12-0, 500300-93-6 (10 pages).
2-[ 1-(3,6-di-2-pyridinyl-4-pyridazinyl)ethylidene]hydrazinecarbothioamide CAS registry No. 76780-41-1.
Bernhardt, P. V. et al., “Tuning the antiproliferative activity of biologically active iron chelators: characterization of the coordination chemistry and biological efficacy of2-acetylpyridine and 2-benzoylpyridine hydrazone ligands”, Journal of Biological Inorganic Chemistry, 2008 (published Sep. 25, 2007), vol. 13, No. I, pp. 107-119. ISSN 0949-8257.
Bernhardt, P. V. et al., “Cytotoxic iron chelators: characterization of the structure, solution chemistry and redox activity ofligands and iron complexes of the di-2-pyridyl ketone isonicotinoyl hydrazone (HPKIH) analogues”, Journal of Biological Inorganic Chemistry, 2003, vol. 8, No. 8, pp. 866-880. ISSN 0949-8257.
Braun, M. et al., “4,5-Diacylpyridazines: synthesis and conversion to 1,4-diaryl-or 1,4- dialkylpyridazino[4,5-d]pyridazines (Pyridazines, VIII)”, Monatshefte fur Chemie, 1978, vol. 109, No. I, pp. 63-71. ISSN 0026-9247.
French, F. A. et al., “The carcinostatic activity ofthiosemicarbazones of formyl heteroaromatic compounds”, Journal of Medicinal Chemistry, 1966, vol. 9, No. 4, pp. 585-589. ISSN 0022-2623.
Yuan, J. et al., “Novel di-2-pyridyl-derived iron chelators with marked and selective antitumor activity: in vitro and in vivo assessment”, Blood, 2004, vol. 104, No. 5, pp. 1450-1458.
European Supplemental Search Report for EP Application No. 09797322 mailed Dec. 20, 2011.
McNeill, “Inhibition of Granulocyte-Macrophage Colony Formation in Vitro by Substituted Isatin Thiosemicarbazones”, Aug. 1, 1973, vol. 4, No. 2, pp. 105-108.
Pectasides, et al., Systemic therapy in metastatic or recurrent endometrial cancer, Mar. 3, 2007, Cancer Treatment Reviews, Saunders, US, vol. 33, No. 2, pp. 177-190.
International Search Report for International Application No. PCT/US2005/021253 mailed Mar. 29, 2006.
Sequence Listing for International Application No. PCT/US2005/021253.
U.S. Appl. No. 13/363,558, filed Feb. 1, 2012 entitled “Inhibitor Compounds and Cancer Treatment Methods” by Wayne R. Danter (0055.10/CIP-C).
CAS Registry No. 868364-38-9, Nov. 18, 2005.
CAS Registry No. 868364-43-6, Nov. 18, 2005.
CAS Registry No. 901285-15-2, Aug. 15, 2006.
CAS Registry No. 901329-97-3, Aug. 15, 2006.
CAS Registry No. 901348-18-3, Aug. 15, 2006.
CAS Registry No. 901349-50-6, Aug. 15, 2006.
Cas Registry No. 901360-08-5, Aug. 15, 2006.
CAS Registry No. 901391-84-2, Aug. 15, 2006.
CAS Registry No. 903180-32-5, Aug. 22, 2006.
CAS Registry No. 903274-24-8, Aug. 26, 2006.
CAS Registry No. 91189-95-6, Nov. 16, 1984.
CAS Registry No. 500300-93-6, Mar. 24, 2003.
CAS Registry No. 518299-22-4, May 21, 2003.
CAS Registry No. 519151-42-9, May 23, 2003.
CAS Registry No. 549530-64-5, Jul. 17, 2003.
CAS Registry No. 732257-35-1, Aug. 25, 2004.
CAS Registry No. 732992-68-6, Aug. 26, 2004.
CAS Registry No. 733793-43-6, Aug. 27, 2004.
CAS Registry No. 802269-45-0, Dec. 23, 2004.
CAS Registry No. 847046-07-5, Mar. 23, 2005.
CAS Registry No. 852401-92-4, Jun. 16, 2005.
CAS Registry No. 852401-95-7, Jun. 16, 2005.
Office Action for CA 2,673,683 mailed Jan. 28, 2013, 8 pages.
EP Examination for EP Application No. 08700510.4 dated Jan. 16, 2013, 5 pages.

* cited by examiner

COMPOUNDS AND METHOD FOR TREATMENT OF CANCER

RELATED APPLICATIONS

This application is a 35 U.S.C. §371 national phase application of PCT/CA2008/002293 /(WO 2009/079797A9), filed on Dec. 24, 2008, entitled "Compounds and Method for Treatment of Cancer," which application claims the benefit of U.S. Provisional Application Ser. No. 61/006,150, filed Dec. 26, 2007.

FIELD OF THE INVENTION

The present invention relates generally to therapeutic compounds and compositions, as well as methods for treatment of cancer.

BACKGROUND OF THE INVENTION

Cancer, irrespective of its pathogenesis, is characterized by uncontrolled growth and survival of cells. Common to most forms of cancer is an error in the cellular mechanism responsible for balancing cell survival and cell death.

According to the American Cancer Society, lung cancer is the leading cause of cancer death for both men and women. Small cell lung cancer (SCLC) accounts for approximately 20% of all lung cancers. The 5-year survival rate for small cell lung cancer is about 15%.

Certain thiosemicarbazones, such as those disclosed in British Patent No. 1,026,401, International Patent Application No. WO2004/066725, Japanese Patent No. 56-95161 and U.S. Pat. No. 4,927,843, have been used to treat, for example, a variety of viruses. Other thiosemicarbazones, however, may be used to treat cancer. French Patent No. 2,879,194 is directed to certain thiosemicarbazones that may be used in the treatment or prevention of cancer, in dermatological treatment, in the treatment of cardiovascular and immune diseases, lipid-metabolism related diseases and modulate PPAR's. International Patent Application No. WO 2006/009765 is directed to specific thiosemicarbazones that may be used in anti-cancer therapy that mitigates the development of drug resistance. U.S. Pat. No. 4,593,027 is directed to hydrazone derivatives that may be used as a chemotherapeutic.

Chinese Patent Application No. 1891701 is directed to a thiosemicarbazone, which are anti-tumour drugs. Chinese Patent Application No. 1907970 is directed to the synthesis of heteroaryl thiocarbonyl compounds. International Patent Application Nos. WO 01/34585 and WO 02/49413 encompass compounds that are thiosemicarbazones, which are used for thrombopoietin mimetrics. International Patent Application No. WO 2004/099371 is directed to thiosemicarbazones that treat ischemia-related conditions. International Patent Application No. WO 2005/087211 is directed to thiocarbazone compounds that are anti-parasitic and inhibit cellular replication associated with cancer cells.

There is a need, however, for new therapeutic drug treatments to treat cancers more effectively and/or with reduced toxicity, particularly lung cancer.

SUMMARY OF THE INVENTION

In accordance with an aspect, there is provided a compound of Formula I:

Formula I

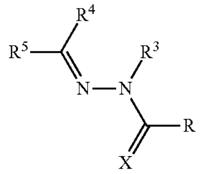

and/or a pharmaceutically-acceptable salt, hydrate, solvate, tautomer, optical isomer, E-isomer, Z-isomer, or combination thereof;

wherein:

X is selected from S or O;

$R^5$ is selected from a substituted or unsubstituted aromatic group, a substituted or unsubstituted heteroaromatic group, or

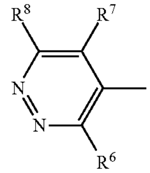

;

when $R^5$ is:

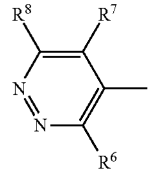

R, $R^3$ and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and $R^6$ to $R^8$ are each independently selected from H, halo, hydroxyl, amino, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group;

when $R^5$ is selected from a substituted or unsubstituted aromatic group, or a substituted or unsubstituted heteroaromatic group, $R^4$ is selected from a substituted or unsubstituted aromatic group, or a substituted or unsubstituted heteroaromatic group, wherein at least one of $R^4$ and $R^5$ is a halo-substituted aromatic group or a halo-substituted heteroaromatic group; and R and $R^3$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group.

In accordance with another aspect, there is provided a compound of Formula II:

Formula II

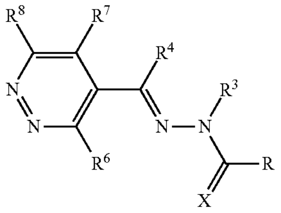

and/or a pharmaceutically-acceptable salt, hydrate, solvate, tautomer, optical isomer, E-isomer, Z-isomer, or combination thereof;

wherein:

X is selected from S or O;

R, $R^3$ and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and $R^6$ to $R^8$ are each independently selected from H, halo, hydroxyl, amino, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group.

In another aspect, R, $R^3$ and $R^4$ are each independently selected from H, halo, hydroxyl, cyano, substituted or unsubstituted alkyl, substituted or unsubstituted alkenyl, substituted or unsubstituted alkynyl, substituted or unsubstituted haloalkyl, substituted or unsubstituted hydroxyalkyl, substituted or unsubstituted alkoxy, a substituted or unsubstituted heterocyclic group, a substituted or unsubstituted aromatic group, a substituted or unsubstituted heteroaromatic group, carboxyl, alkylcarbonyl, arylcarbonyl, cycloalkylcarbonyl, heterocyclylcarbonyl, amino, aminoalkyl, alkylaminoalkyl, heterocyclylalkyl, aralkyl, arylalkenyl, arylalkynyl, alkylthio, alkylamino, arylamino, heteroarylamino, aralkylamino, alkylaminoalkylamino, arylthio, aralkylthio, aryloxy, aralkoxy, heterocyclylalkoxy, heterocyclyloxyalkyl, cycloalkyl, and cycloalkenyl.

In another aspect, $R^4$ is selected from a substituted or unsubstituted aromatic group, or a substituted or unsubstituted heteroaromatic group, the substituted aromatic group or heteroaromatic group being substituted with at least one group selected from halo, hydroxyl, amino, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group and $R^3$ is H or substituted or unsubstituted alkyl.

In another aspect, said at least one group is selected from halo, hydroxyl, cyano, amino, nitro, substituted or unsubstituted alkyl, substituted or unsubstituted alkenyl, substituted or unsubstituted alkynyl, substituted or unsubstituted haloalkyl, substituted or unsubstituted hydroxyalkyl, substituted or unsubstituted alkoxy, a substituted or unsubstituted heterocyclic group, a substituted or unsubstituted aromatic group, a substituted or unsubstituted heteroaromatic group, carboxyl, alkylcarbonyl, arylcarbonyl, cycloalkylcarbonyl, heterocyclylcarbonyl, aminoalkyl, alkylaminoalkyl, heterocyclylalkyl, aralkyl, arylalkenyl, arylalkynyl, alkylthio, alkylamino, arylamino, heteroarylamino, aralkylamino, alkylaminoalkylamino, arylthio, aralkylthio, aryloxy, aralkoxy, heterocyclylalkoxy, heterocyclyloxyalkyl, cycloalkyl, and cycloalkenyl.

In another aspect, $R^4$ is selected from a substituted aromatic group or heteroaromatic group. In another aspect, said at least one group is selected from halo, hydroxyl, cyano, amino, aminoalkyl or nitro. In another aspect, $R^4$ is selected from a substituted pyridinyl group or a substituted phenyl group. In a further aspect, the substituted pyridinyl group is substituted in the para position or the substituted phenyl group is substituted in the ortho position. In another aspect, the substituted pyridinyl group or the substituted phenyl group is substituted with the hydroxyl, amino, or aminoalkyl. In another aspect, the substituted pyridinyl group is a substituted 2-pyridinyl group.

In another aspect, $R^6$ to $R^8$ are each independently selected from H, halo, hydroxyl, amino, nitro, a substituted or unsubstituted hydrocarbon group, a substituted or unsubstituted heterogeneous group. In another aspect, $R^6$ to $R^8$ are each H.

In another aspect, R is $NR^1R^2$, wherein:

$R^1$ and $R^2$ are each independently selected from H, halo, hydroxy, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, or $R^1$ and $R^2$ together form a substituted or unsubstituted heterocyclic group, a substituted or unsubstituted aromatic group, or a substituted or unsubstituted heteroaromatic group.

In another aspect, $R^1$ and $R^2$ together form a substituted or unsubstituted heterocyclic group. In another aspect, $NR^1R^2$ is a substituted or unsubstituted piperazinyl group or pyridinyl group. In another aspect, $NR^1R^2$ is a substituted or unsubstituted piperazinyl group. In another aspect, $NR^1R^2$ is:

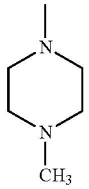

or

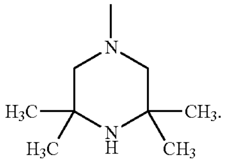

In yet another aspect, X is S.

In another aspect, the compound is:

1A

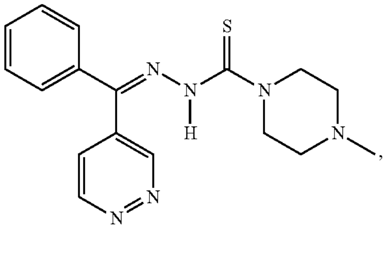

-continued

1C

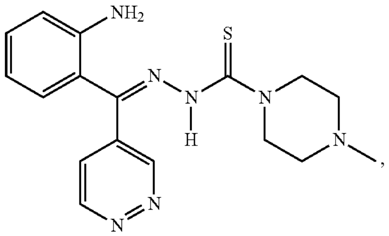
,

1D

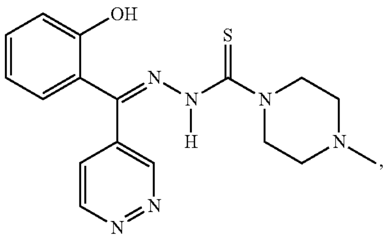
,

1E

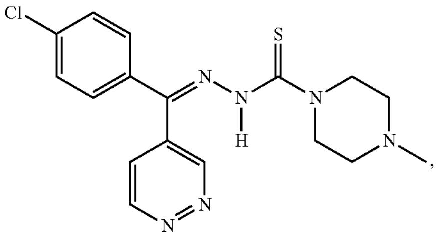
,

1F

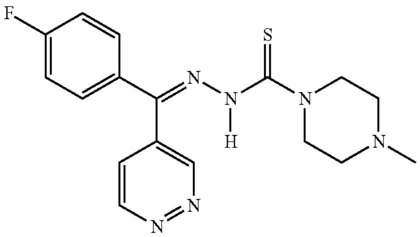

and/or a pharmaceutically-acceptable salt, hydrate, solvate, tautomer, optical isomer, E-isomer, Z-isomer, or combination thereof.

In another aspect, the compound is:

1G

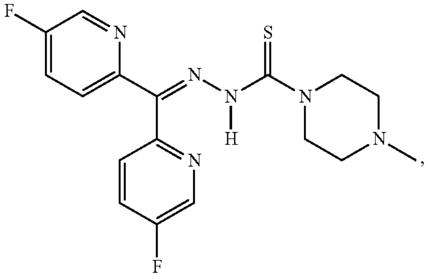
,

-continued

1H

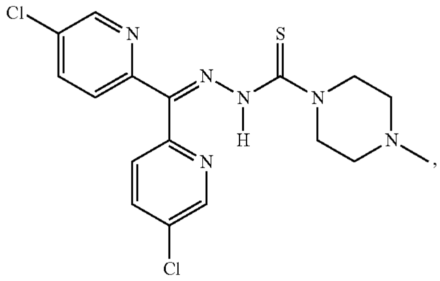
, or

1I

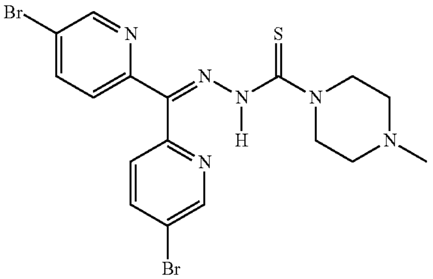

and/or a pharmaceutically-acceptable salt, hydrate, solvate, tautomer, optical isomer, E-isomer, Z-isomer, or combination thereof.

In another aspect, the compound is:

1J

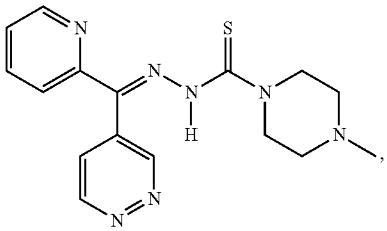
,

1K

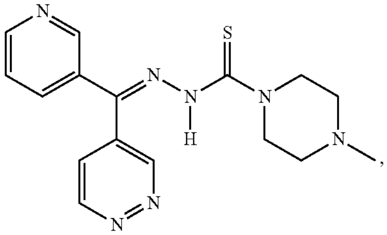
, or

1L

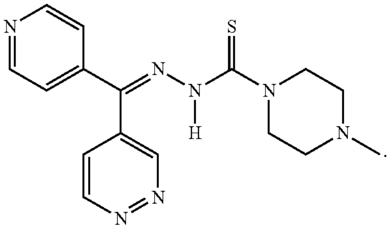
.

and/or a pharmaceutically-acceptable salt, hydrate, solvate, tautomer, optical isomer, E-isomer, Z-isomer, or combination thereof.

In another aspect, the compound of the invention is orally absorbed by a mammal. In another aspect, at least about 50% of the compound is orally absorbed by a mammal. In another aspect, the mammal is a human. In another aspect, the compound has an $IC_{50}$ for a cancer cell population of less than about 1000 nM. In another aspect, the compound is for treatment of a cancer.

In another aspect, the cancer is selected from lung cancer, cervical cancer, ovarian cancer, cancer of CNS, skin cancer, prostate cancer, sarcoma, breast cancer, leukemia, colorectal cancer, head cancer, neck cancer, lymphoma, pancreatic cancer, gastric cancer, or kidney cancer.

In another aspect, the cancer is selected from small cell lung cancer, hormone resistant breast cancer, hormone resistant prostate cancer, acute leukemia, chronic leukemia, colorectal cancer or melanoma.

In another aspect, the cancer is a carcinoma. In another aspect, the carcinoma is selected from small cell carcinomas, cervical carcinomas, glioma, astrocytoma, prostate carcinomas, ovarian carcinomas, melanoma, breast carcinomas, or colorectal carcinomas. In another aspect, the carcinoma is small cell lung carcinoma.

In another aspect, the compound is provided in combination with radiation therapy.

In another aspect, a pharmaceutical composition is provided comprising the compound of the invention and at least one pharmaceutically acceptable carrier and/or diluent. In another aspect, a pharmaceutical composition comprising an anti-cancer agent and the compound according to the invention.

In another aspect, the anti-cancer agent is selected from DNA-interactive agents, antimetabolites, tubulin-interactive agents, hormonal agents, estrogen receptor modulators, androgen receptor modulators, retinoid receptor modulators, tyrosine kinase inhibitors, cytotoxic agents, antiproliferative agents, prenyl-protein transferase inhibitors, HMG-CoA reductase inhibitors, HIV protease inhibitors, reverse transcriptase inhibitors, other angiogenesis inhibitors or combinations thereof.

In another aspect, the composition is provided in combination with radiation therapy. In another aspect, a method is provided for treating a cancer in a mammal, comprising administering to the mammal a therapeutically effective amount of the compound according to the invention. In another aspect, the compound is co-administered with radiation therapy. In another aspect, a method for treating a cancer in a mammal is provided, comprising administering to the mammal a therapeutically effective amount of the composition according to the invention. In another aspect, the composition is co-administered with radiation therapy. In another aspect, the compound or composition is administered orally and/or parenterally. In another aspect, the compound or composition is administered intravenously and/or intraperitoneally.

In another aspect, use of a compound according to the invention for the manufacture of a medicament for treatment of a cancer in a mammal is provided. In another aspect, use of a composition according to the invention for the manufacture of a medicament for treatment of a cancer in a mammal is provided. In another aspect, use of a compound according to the invention to treat a cancer in a mammal is provided. In another aspect, the use of the compound in combination with radiation therapy is provided. In another aspect, use of a composition according to the invention to treat a cancer in a mammal is provided. In another aspect, the use of the composition in combination with radiation therapy is provided.

In another aspect, the use is wherein the cancer is selected from lung cancer, cervical cancer, ovarian cancer, cancer of CNS, skin cancer, prostate cancer, sarcoma, breast cancer, leukemia, colorectal cancer, head cancer, neck cancer, lymphoma, pancreatic cancer, gastric cancer, or kidney cancer. In another aspect, the cancer is selected from small cell lung cancer, breast cancer, acute leukemia, chronic leukemia, colorectal cancer. In another aspect, the cancer is a carcinoma. In another aspect, the carcinoma is selected from small cell carcinomas, cervical carcinomas, glioma, astrocytoma, prostate carcinomas, ovarian carcinomas, melanoma, breast carcinomas, or colorectal carcinomas. In another aspect, the carcinoma is small cell lung carcinoma.

In another aspect, there is provided a method for treating a cancer in a mammal, comprising administering to the mammal a therapeutically effective amount of a compound of Formula VII:

Formula VII

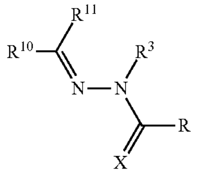

and/or a pharmaceutically-acceptable salt, hydrate, solvate, tautomer, optical isomer, E-isomer, Z-isomer, or combination thereof;

wherein:

X is selected from S or O;

R and $R^3$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and $R^{10}$ and $R^{11}$ are each independently selected from a substituted or unsubstituted aromatic group, or a substituted or unsubstituted heteroaromatic group.

In another aspect, R and $R^3$ are each independently selected from H, halo, hydroxyl, cyano, substituted or unsubstituted alkyl, substituted or unsubstituted alkenyl, substituted or unsubstituted alkynyl, substituted or unsubstituted haloalkyl, substituted or unsubstituted hydroxyalkyl, substituted or unsubstituted alkoxy, a substituted or unsubstituted heterocyclic group, a substituted or unsubstituted aromatic group, a substituted or unsubstituted heteroaromatic group, carboxyl, alkylcarbonyl, arylcarbonyl, cycloalkylcarbonyl, heterocyclylcarbonyl, amino, aminoalkyl, alkylaminoalkyl, heterocyclylalkyl, aralkyl, arylalkenyl, arylalkynyl, alkylthio, alkylamino, arylamino, heteroarylamino, aralkylamino, alkylaminoalkylamino, arylthio, aralkylthio, aryloxy, aralkoxy, heterocyclylalkoxy, heterocyclyloxyalkyl, cycloalkyl, and cycloalkenyl.

In another aspect, $R^{10}$ and $R^{11}$ are each independently selected from a substituted or unsubstituted aromatic group, or a substituted or unsubstituted heteroaromatic group, the substituted aromatic group or heteroaromatic group being substituted with at least one group selected from halo, hydroxyl, amino, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group and $R^3$ is H or substituted or unsubstituted alkyl.

In another aspect, said at least one group is selected from halo, hydroxyl, cyano, amino, nitro, substituted or unsubstituted alkyl, substituted or unsubstituted alkenyl, substituted or unsubstituted alkynyl, substituted or unsubstituted haloalkyl, substituted or unsubstituted hydroxyalkyl, substituted or unsubstituted alkoxy, a substituted or unsubstituted heterocyclic group, a substituted or unsubstituted aromatic group, a substituted or unsubstituted heteroaromatic group, carboxyl, alkylcarbonyl, arylcarbonyl, cycloalkylcarbonyl, heterocyclylcarbonyl, aminoalkyl, alkylaminoalkyl, heterocyclylalkyl, aralkyl, arylalkenyl, arylalkynyl, alkylthio, alkylamino, arylamino, heteroarylamino, aralkylamino, alkylaminoalkylamino, arylthio, aralkylthio, aryloxy, aralkoxy, heterocyclylalkoxy, heterocyclyloxyalkyl, cycloalkyl, and cycloalkenyl.

In another aspect, said at least one group is selected from halo, hydroxyl, cyano, amino, aminoalkyl or nitro.

In another aspect, $R^{10}$ and $R^{11}$ are each independently selected from a substituted or unsubstituted pyridinyl group or a substituted or unsubstituted phenyl group. In another aspect, the pyridinyl group is a 2-pyridinyl, 3-pyridinyl, or 4-pyridinyl group. In another aspect, R is as above. In another aspect, X is S.

In another aspect, the compound is:

VIIA

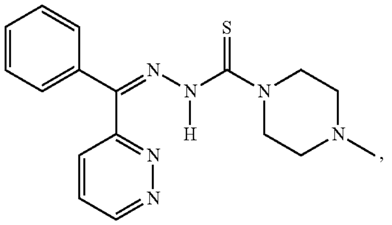

VIIB

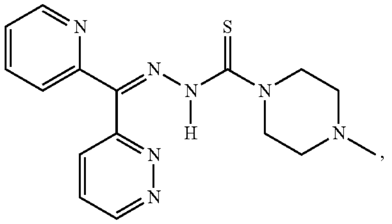

VIIC

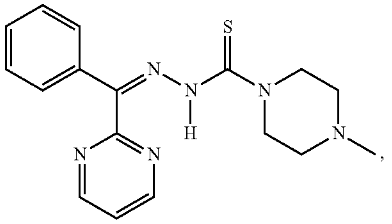

VIID

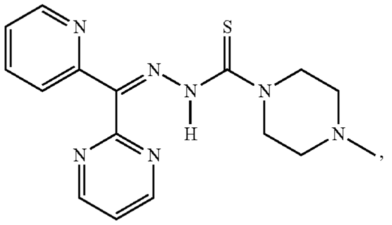

-continued

VIIE

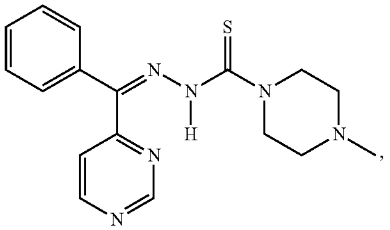

VIIF

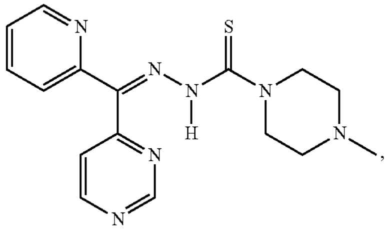

VIIG

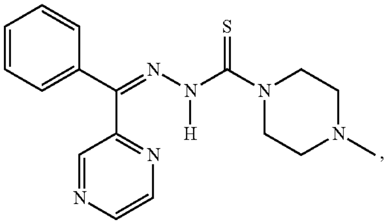

VIIH

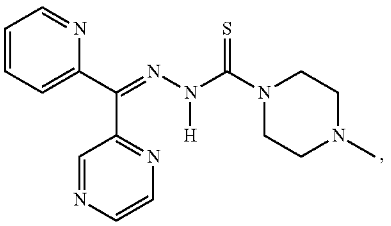

VIII

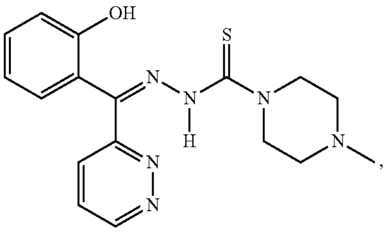

or

VIIJ

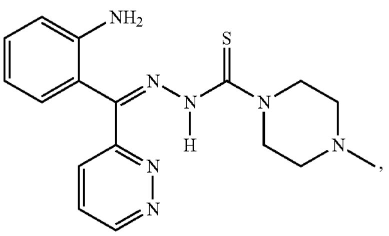

or

-continued

IB

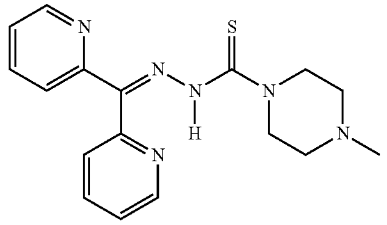

and/or a pharmaceutically-acceptable salt, hydrate, solvate, tautomer, optical isomer, E-isomer, Z-isomer, or combination thereof.

In another aspect, the compound is co-administered with radiation therapy. In another aspect, the cancer is lung cancer, cervical cancer, ovarian cancer, cancer of CNS, skin cancer, prostate cancer, sarcoma, breast cancer, leukemia, colorectal cancer, head cancer, neck cancer, lymphoma, pancreatic cancer, gastric cancer, or kidney cancer. In another aspect, the cancer is selected from small cell lung cancer, hormone resistant breast cancer, hormone resistant prostate cancer, acute leukemia, chronic leukemia, colorectal cancer, or melanoma. In another aspect, the cancer is a carcinoma. In another aspect, the carcinoma is selected from small cell carcinomas, cervical carcinomas, glioma, astrocytoma, prostate carcinomas, ovarian carcinomas, melanoma, breast carcinomas, or colorectal carcinomas. In another aspect, the carcinoma is small cell lung carcinoma.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

Embodiments of the present invention will now be described, by way of example only, with reference to the attached Figures.

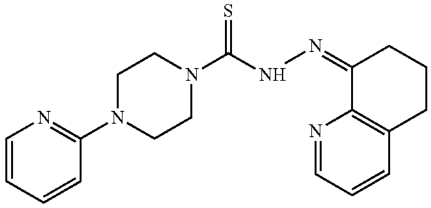

COTI-2MO5

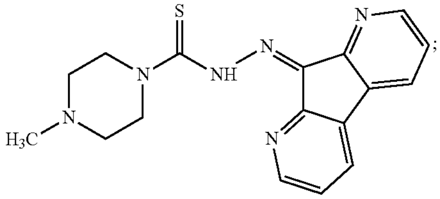

;

COTI-219MO5

Figure 7:
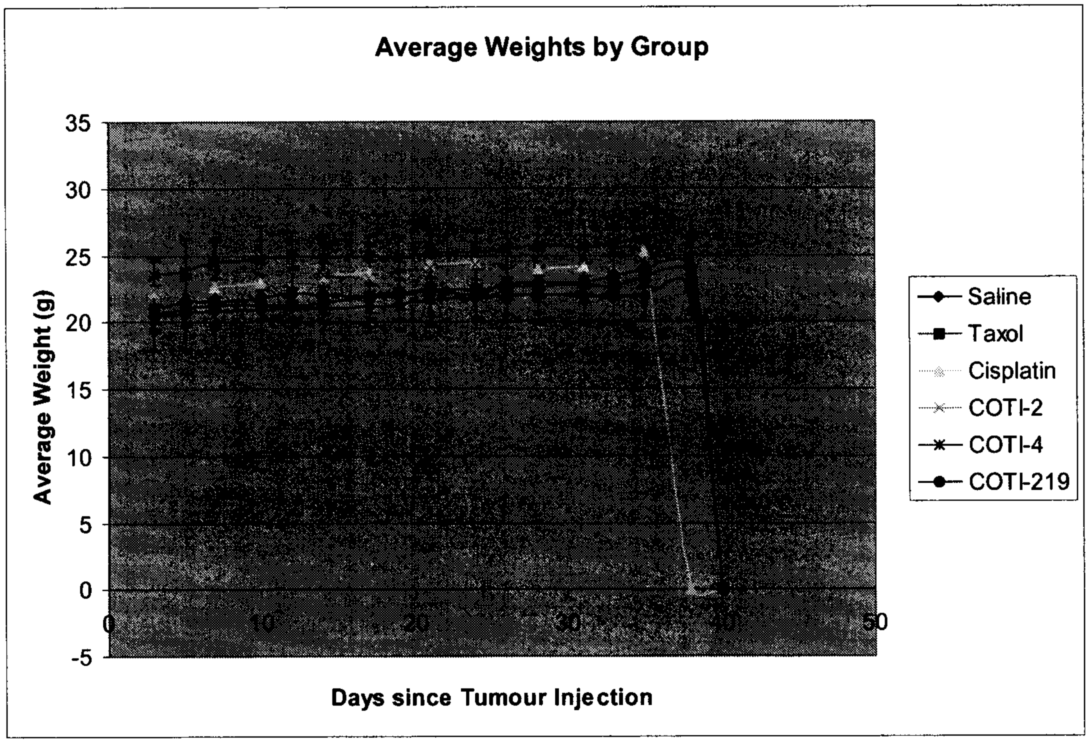
Figure 8:
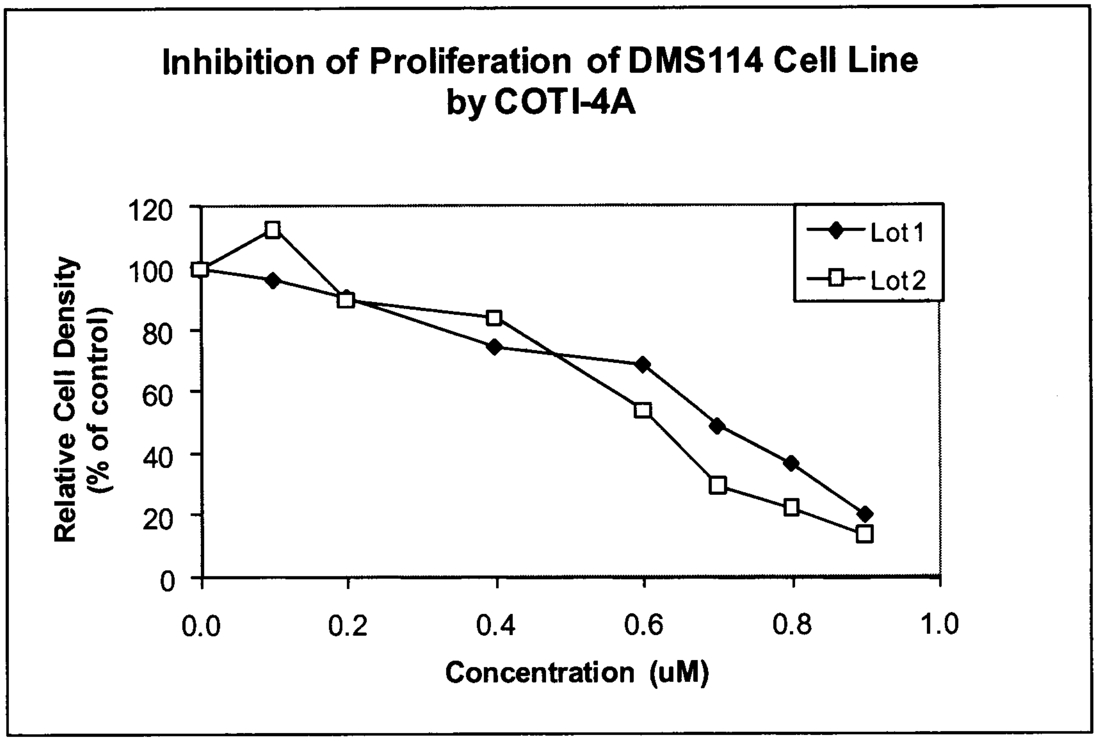
Figure 9:
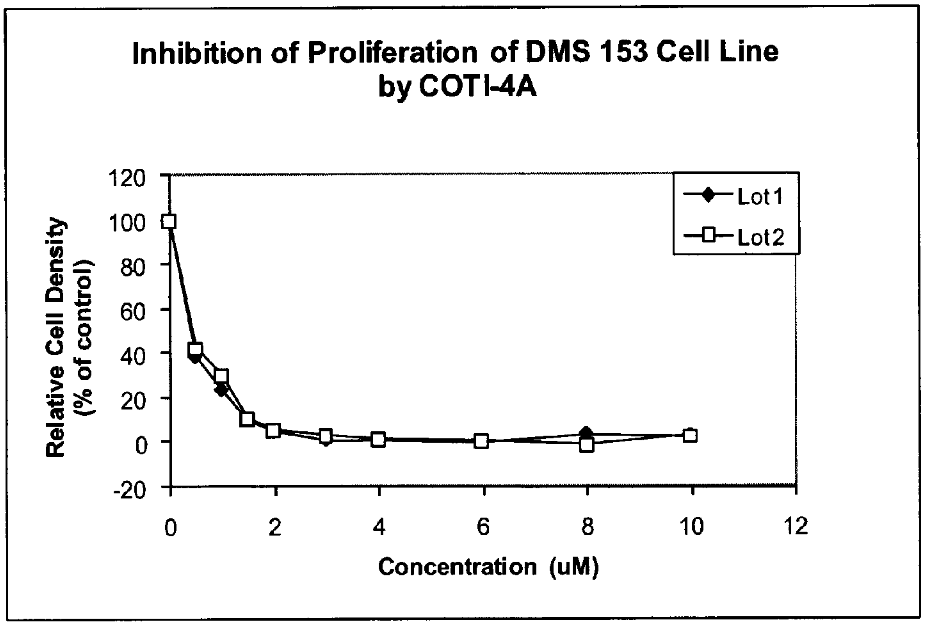
Figure 10:
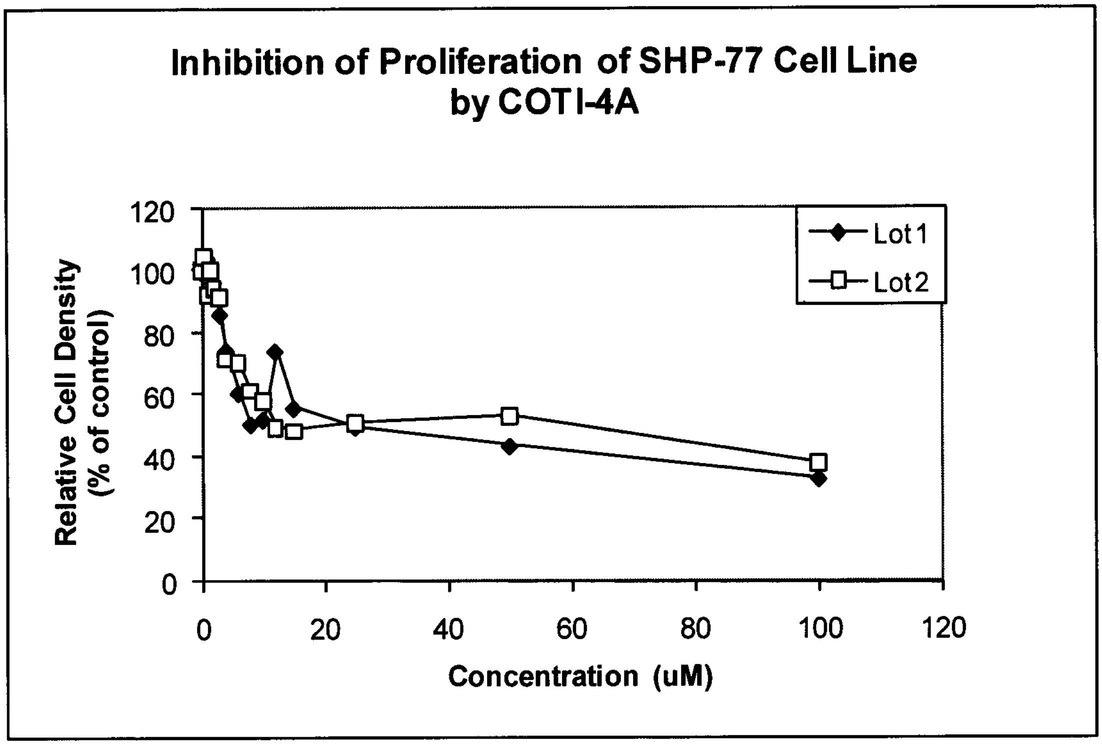
Figure 11:
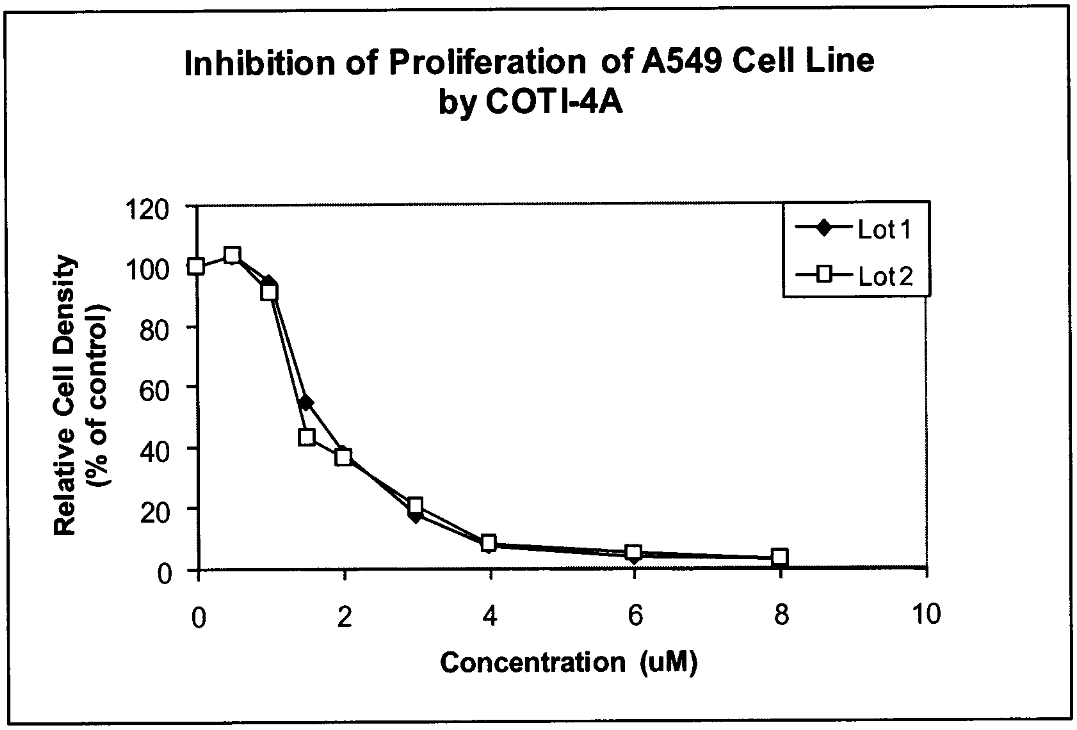
Figure 12:
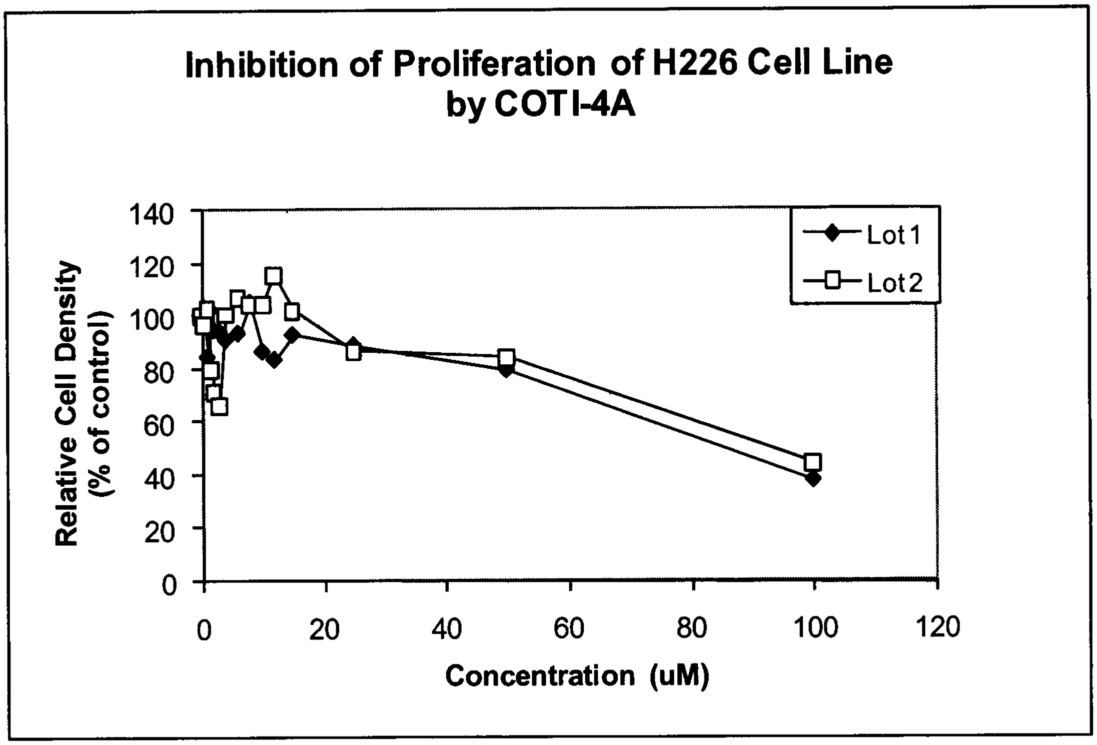
Figure 13:
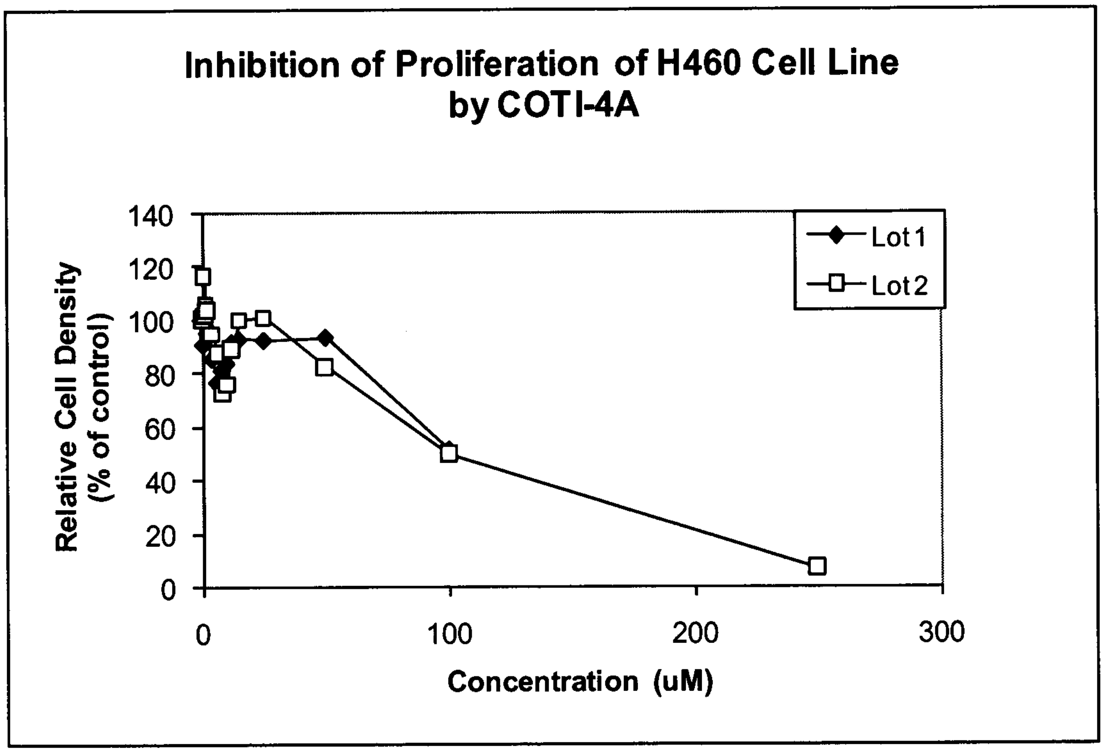
Figure 14:
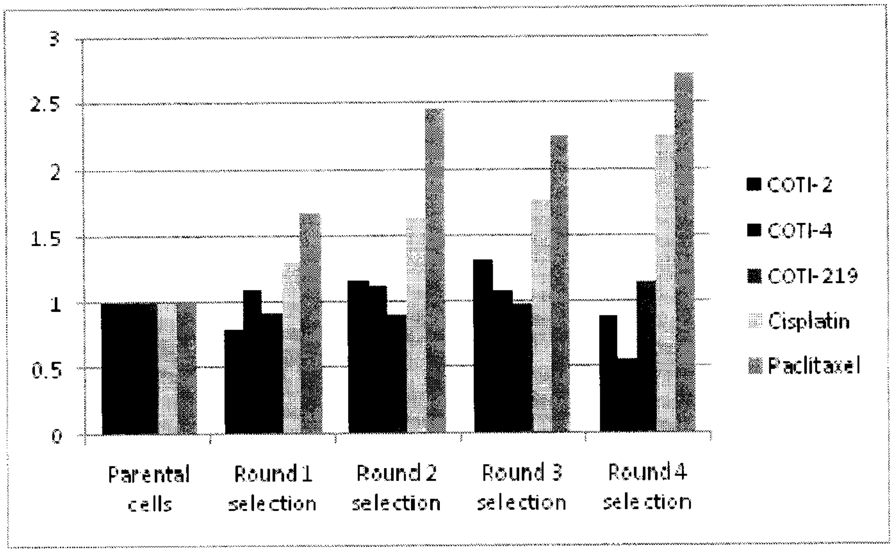
Figure 15:
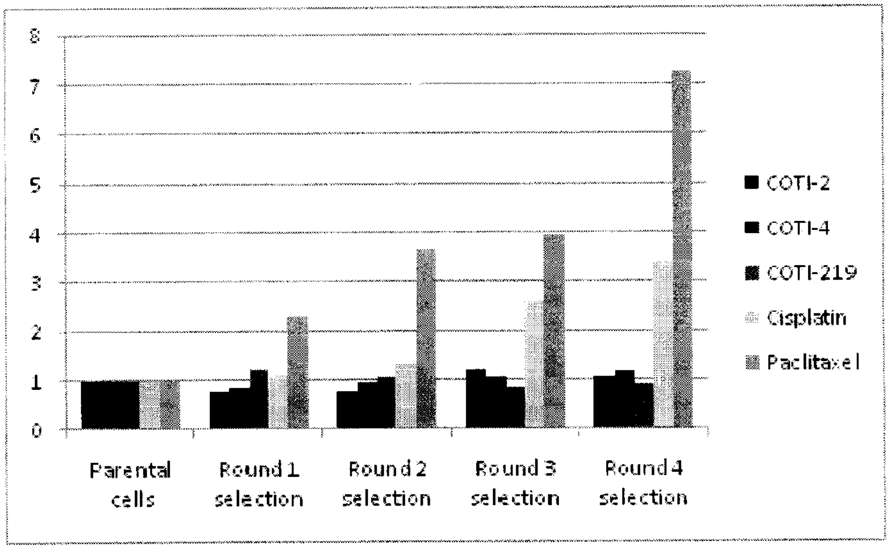
Figure 16:
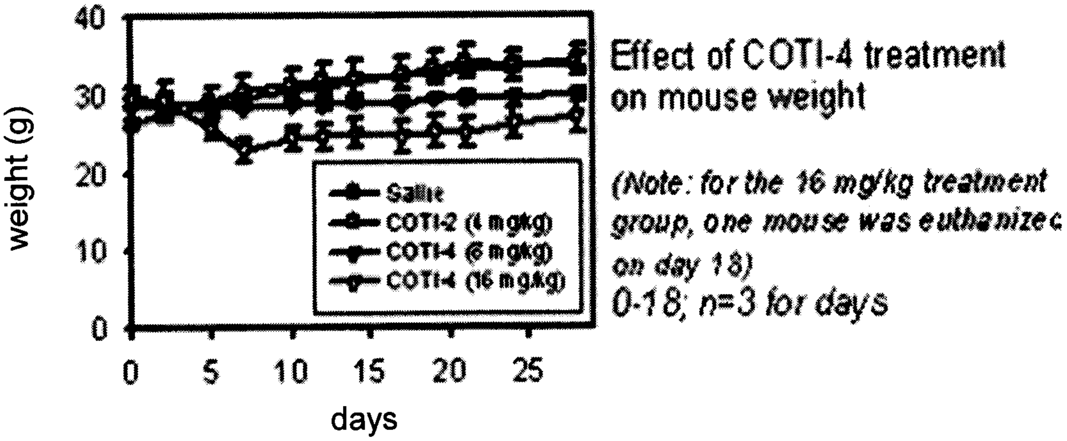

FIG. 7 shows the average weight of animals treated with COTI-4, according to the invention, versus saline (as a control), Taxol® and cisplatin comparative controls. Also depicted are results from the compounds "COTI-2" and "COTI-219", as referred to above;

FIG. 8 shows the dose response of human SCLC cell line DMS-114 to COTI-4A, according to the invention (the two different lots relate to replicate experiments);

FIG. 9 shows the dose response of human SCLC cell line DMS-153 to COTI-4A, according to the invention (the two different lots relate to replicate experiments);

FIG. 10 shows the dose response of human SCLC cell line SHP-77 to COTI-4A, according to the invention (the two different lots relate to replicate experiments);

FIG. 11 shows the dose response of human non-SCLC cell line A-549 to COTI-4A, according to the invention (the two different lots relate to replicate experiments);

FIG. 12 shows the dose response of human non-SCLC cell line H-226 to COTI-4A, according to the invention (the two different lots relate to replicate experiments);

FIG. 13 shows the dose response of human non-SCLC cell line H-460 to COTI-4A, according to the invention (the two different lots relate to replicate experiments);

FIG. 14 shows lack of emerging resistance in DMS153 cells treated with COTI-4 and the prior art compounds COTI-2 and COTI-219;

FIG. 15 shows lack of emerging resistance in SHP77 cells treated with COTI-4 and the prior art compounds COTI-2 and COTI-219; and, FIG. 16 shows the effect on mouse weight of treatment with compounds according to the invention at three different doses.

DETAILED DESCRIPTION

The present invention is directed to a thiosemicarbazone, a semicarbazone, a composition comprising the thiosemicarbazone and/or the semicarbazone, a method of administration thereof, and use thereof to treat a cancer.

Definitions

When describing the compounds, compositions, methods and uses of this invention, the following terms have the following meanings unless otherwise indicated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The compounds of the present invention may have asymmetric centers, chiral axes, and chiral planes (as described, for example, in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers, with all possible isomers and mixtures thereof, including optical isomers, E isomers, and Z isomers, being included in the present invention. In addition, the compounds disclosed herein may exist as tautomers and both tautomeric forms are intended to be encompassed by the scope of the invention, even though only one tautomeric structure may be depicted.

Generally, reference to a certain element such as hydrogen or H is meant to, if appropriate, include all isotopes of that element.

Where the term "alkyl group" is used, either alone or within other terms such as "haloalkyl group" and "alkylamino group", it encompasses linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In embodiments, alkenyl groups are "lower alkenyl" groups having two to about four carbon atoms. Examples of alkenyl groups include, but are not limited thereto, ethenyl, propenyl, allyl, propenyl, butenyl and 4-methylbutenyl. The terms "alkenyl group" and "lower alkenyl group", encompass groups having "cis" and "trans" orientations, or alternatively, "E" and "Z" orientations.

The term "alkynyl group" denotes linear or branched carbon radicals having at least one carbon-carbon triple bond. The term "alkynyl group" can encompass conjugated and non-conjugated carbon-carbon triple bonds or combinations thereof. Alkynyl group, for example and without being limited thereto, can encompass two to about twenty carbon atoms or, in a particular embodiment, two to about twelve carbon atoms. In embodiments, alkynyl groups are "lower alkynyl" groups having two to about ten carbon atoms. Some examples are lower alkynyl groups having two to about four carbon atoms. Examples of such groups include propargyl, butynyl, and the like.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are monohaloalkyl, dihaloalkyl and polyhaloalkyl groups including perhaloalkyl. A monohaloalkyl group, for one example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl group" encompasses linear or branched alkyl groups having, for example and without being limited thereto, one to about ten carbon atoms, any one of which may be substituted with one or more hydroxyl groups. In embodiments, hydroxyalkyl groups are "lower hydroxyalkyl" groups having one to six carbon atoms and one or more hydroxyl groups. Examples of such groups include hydroxymethyl, hydroxyethyl, hydroxypropyl, hydroxybutyl and hydroxyhexyl.

The term "alkoxy group" encompasses linear or branched oxy-containing groups each having alkyl portions of, for example and without being limited thereto, one to about ten carbon atoms. In embodiments, alkoxy groups are "lower alkoxy" groups having one to six carbon atoms. Examples of such groups include methoxy, ethoxy, propoxy, butoxy and tert-butoxy. In certain embodiments, lower alkoxy groups have one to three carbon atoms. The "alkoxy" groups may be further substituted with one or more halo atoms, such as fluoro, chloro or bromo, to provide "haloalkoxy" groups. In other embodiments, lower haloalkoxy groups have one to three carbon atoms. Examples of such groups include fluoromethoxy, chloromethoxy, trifluoromethoxy, trifluoroethoxy, fluoroethoxy, and fluoropropoxy.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 4 to 10 carbon atoms, typically 4 to 7 carbon atoms, and more typically 4 to 6 carbon atoms in the ring. Typical polycyclic aromatic groups have two or three rings. Polycyclic aromatic groups having two rings typically have 8 to 12 carbon atoms, preferably 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The term "heteroatom" means an atom other than carbon. Typically, heteroatoms are selected from the group consisting of sulfur, phosphorous, nitrogen and oxygen atoms. Groups containing more than one heteroatom may contain different heteroatoms.

The term "heteroaromatic group" or "heteroaryl group" means an aromatic group having one or more rings wherein such rings may be attached together in a pendent manner or may be fused, wherein the aromatic group has at least one heteroatom. Monocyclic heteroaromatic groups may contain 4 to 10 member atoms, typically 4 to 7 member atoms, and more typically 4 to 6 member atoms in the ring. Typical polycyclic heteroaromatic groups have two or three rings. Polycyclic aromatic groups having two rings typically have 8 to 12 member atoms, more typically 8 to 10 member atoms in the rings. Examples of heteroaromatic groups include, but are not limited thereto, pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like.

The term "carbocyclic group" means a saturated or unsaturated carbocyclic hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups may contain 4 to 10 carbon atoms, typically 4 to 7 carbon atoms, and more typically 5 to 6 carbon atoms in the ring. Bicyclic carbocyclic groups may contain 8 to 12 carbon atoms, typically 9 to 10 carbon atoms in the rings.

The term "heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heterocyclic groups can be fused, spiro, or bridged ring systems. Monocyclic heterocyclic groups may contain 4 to 10 member atoms (i.e., including both carbon atoms and at least 1 heteroatom), typically 4 to 7, and more typically 5 to 6 in the ring. Bicyclic heterocyclic groups may contain 8 to 18 member atoms, typically 9 or 10 member atoms in the rings. Representative heterocyclic groups include, by way of example, pyrrolidine, imidazolidine, pyrazolidine, piperidine, 1,4-dioxane, morpholine, thiomorpholine, piperazine, 3-pyrroline and the like.

The term "heterogeneous group" means a saturated or unsaturated chain of non-hydrogen member atoms comprising carbon atoms and at least one heteroatom. Heterogeneous groups typically have 1 to 25 member atoms. More typically, the chain contains 1 to 12 member atoms, 1 to 10, and most typically 1 to 6. The chain may be linear or branched. Typical branched heterogeneous groups have one or two branches, more typically one branch. Typically, heterogeneous groups are saturated. Unsaturated heterogeneous groups may have one or more double bonds, one or more triple bonds, or both. Typical unsaturated heterogeneous groups have one or two double bonds or one triple bond. More typically, the unsaturated heterogeneous group has one double bond.

The term "hydrocarbon group" or "hydrocarbyl group" means a chain of 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

When the term "unsaturated" is used in conjunction with any group, the group may be fully unsaturated or partially unsaturated. However, when the term "unsaturated" is used in conjunction with a specific group defined herein, the term maintains the limitations of that specific group. For example, an unsaturated "carbocyclic group", based on the limitations of the "carbocyclic group" as defined herein, does not encompass an aromatic group.

The terms "carboxy group" or "carboxyl group", whether used alone or with other terms, such as "carboxyalkyl group", denotes —(C═O)—O—.

The term "carbonyl group", whether used alone or with other terms, such as "aminocarbonyl group", denotes —(C═O)—.

The terms "alkylcarbonyl group" denotes carbonyl groups which have been substituted with an alkyl group. In certain embodiments, "lower alkylcarbonyl group" has lower alkyl group as described above attached to a carbonyl group.

The term "aminoalkyl group" encompasses linear or branched alkyl groups having one to about ten carbon atoms any one of which may be substituted with one or more amino groups. In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The term "alkylaminoalkyl group" encompasses aminoalkyl groups having the nitrogen atom independently substituted with an alkyl group. In certain embodiments, the alkylaminoalkyl groups are "loweralkylaminoalkyl" groups having alkyl groups of one to six carbon atoms. In other embodiments, the lower alkylaminoalkyl groups have alkyl groups of one to three carbon atoms. Suitable alkylaminoalkyl groups may be mono or dialkyl substituted, such as N-methylaminomethyl, N,N-dimethyl-aminoethyl, N,N-diethylaminomethyl and the like.

The term "aralkyl group" encompasses aryl-substituted alkyl groups. In embodiments, the aralkyl groups are "lower aralkyl" groups having aryl groups attached to alkyl groups having one to six carbon atoms. In other embodiments, the lower aralkyl groups phenyl is attached to alkyl portions having one to three carbon atoms. Examples of such groups include benzyl, diphenylmethyl and phenylethyl. The aryl in said aralkyl may be additionally substituted with halo, alkyl, alkoxy, haloalkyl and haloalkoxy.

The term "arylalkenyl group" encompasses aryl-substituted alkenyl groups. In embodiments, the arylalkenyl groups are "lower arylalkenyl" groups having aryl groups attached to alkenyl groups having two to six carbon atoms. Examples of such groups include phenylethenyl. The aryl in said arylalkenyl may be additionally substituted with halo, alkyl, alkoxy, haloalkyl and haloalkoxy.

The term "arylalkynyl group" encompasses aryl-substituted alkynyl groups. In embodiments, arylalkynyl groups are "lower arylalkynyl" groups having aryl groups attached to alkynyl groups having two to six carbon atoms. Examples of such groups include phenylethynyl. The aryl in said aralkyl may be additionally substituted with halo, alkyl, alkoxy, haloalkyl and haloalkoxy. The terms benzyl and phenylmethyl are interchangeable.

The term "alkylthio group" encompasses groups containing a linear or branched alkyl group, of one to ten carbon atoms, attached to a divalent sulfur atom. In certain embodiments, the lower alkylthio groups have one to three carbon atoms. An example of "alkylthio" is methylthio, ($CH_3S$—).

The term "alkylamino group" denotes amino groups which have been substituted with one alkyl group and with two alkyl groups, including terms "N-alkylamino" and "N,N-dialkylamino". In embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino and the like.

The term "arylamino group" denotes amino groups which have been substituted with one or two aryl groups, such as N-phenylamino. The "arylamino" groups may be further substituted on the aryl ring portion of the group.

The term "heteroarylamino" denotes amino groups which have been substituted with one or two heteroaryl groups, such as N-thienylamino. The "heteroarylamino" groups may be further substituted on the heteroaryl ring portion of the group.

The term "aralkylamino group" denotes amino groups which have been substituted with one or two aralkyl groups. In other embodiments, there are phenyl-$C_1$-$C_3$-alkylamino groups, such as N-benzylamino. The "aralkylamino" groups may be further substituted on the aryl ring portion of the group.

The term "alkylaminoalkylamino group" denotes alkylamino groups which have been substituted with one or two alkylamino groups. In embodiments, there are $C_1$-$C_3$-alkylamino-$C_1$-$C_3$-alkylamino groups.

The term "arylthio group" encompasses aryl groups of six to ten carbon atoms, attached to a divalent sulfur atom. An example of "arylthio" is phenylthio. The term "aralkylthio group" encompasses aralkyl groups as described above, attached to a divalent sulfur atom. In certain embodiments there are phenyl-$C_1$-$C_3$-alkylthio groups. An example of "aralkylthio" is benzylthio.

The term "aryloxy group" encompasses optionally substituted aryl groups, as defined above, attached to an oxygen atom. Examples of such groups include phenoxy.

The term "aralkoxy group" encompasses oxy-containing aralkyl groups attached through an oxygen atom to other groups. In certain embodiments, aralkoxy groups are "lower aralkoxy" groups having optionally substituted phenyl groups attached to lower alkoxy group as described above.

The term "cycloalkyl group" includes saturated carbocyclic groups. In certain embodiments, cycloalkyl groups include $C_3$-$C_6$ rings. In embodiments, there are compounds that include, cyclopentyl, cyclopropyl, and cyclohexyl.

The term "cycloalkenyl group" includes carbocyclic groups that have one or more carbon-carbon double bonds; conjugated or non-conjugated, or a combination thereof. "Cycloalkenyl" and "cycloalkyldienyl" compounds are included in the term "cycloalkenyl". In certain embodiments, cycloalkenyl groups include $C_3$-$C_6$ rings. Examples include cyclopentenyl, cyclopentadienyl, cyclohexenyl and cycloheptadienyl. The "cycloalkenyl" group may have 1 to 3 substituents such as lower alkyl, hydroxyl, halo, haloalkyl, nitro, cyano, alkoxy, lower alkylamino, and the like.

The term "suitable substituent", "substituent" or "substituted" used in conjunction with the groups described herein refers to a chemically and pharmaceutically acceptable group, i.e., a moiety that does not negate the therapeutic activity of the inventive compounds. It is understood that substituents and substitution patterns on the compounds of the invention may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon/member atom or on different carbons/member atoms, as long as a stable structure results. Illustrative examples of some suitable substituents include, cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C═O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl. Typical substituents include aromatic groups, substituted aromatic groups, hydrocarbon groups including alkyl groups such as methyl groups, substituted hydrocarbon groups such as benzyl, and heterogeneous groups including alkoxy groups such as methoxy groups.

The term "fused" means in which two or more carbons/member atoms are common to two adjoining rings, e.g., the rings are "fused rings".

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The present invention includes pharmaceutically acceptable salts, solvates and prodrugs of the compounds of the invention and mixtures thereof.

The terms "comprising", "having" and "including", and various endings thereof, are meant to be open ended, including the indicated component but not excluding other elements.

A compound of the invention is represented by a compound of Formula I:

Formula I

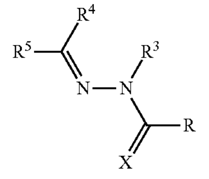

wherein:

X is selected from S or O;

$R^5$ is selected from a substituted or unsubstituted aromatic group, a substituted or unsubstituted heteroaromatic group, or

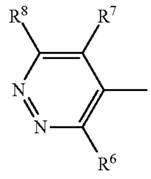

; when $R^5$ is:

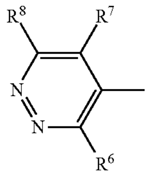

R, $R^3$ and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and $R^6$ to $R^8$ are each independently selected from H, halo, hydroxyl, amino, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group;

when $R^5$ is selected from a substituted or unsubstituted aromatic group, or a substituted or unsubstituted heteroaromatic group, $R^4$ is selected from a substituted or unsubstituted aromatic group, or a substituted or unsubstituted heteroaromatic group, wherein at least one of $R^4$ and $R^5$ is a halo-substituted aromatic group or a halo-substituted heteroaromatic group; and R and $R^3$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group.

In one embodiment, a compound represented by a compound of Formula II:

Formual II

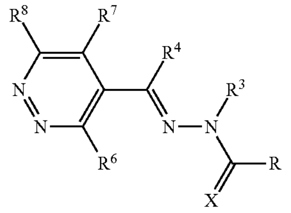

R, $R^3$ and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group. $R^6$ to $R^8$ are each independently selected from H, halo, hydroxyl, amino, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group.

In another embodiment, a compound represented by a compound of Formula III:

Formual III

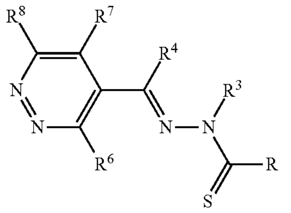

R, $R^3$ and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group. $R^6$ to $R^8$ are each independently selected from H, halo, hydroxyl, amino, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group.

In another embodiment of Formulae II or III, R, $R^3$ and $R^4$ are each independently selected from H, halo, hydroxyl, cyano, substituted or unsubstituted alkyl, substituted or unsubstituted alkenyl, substituted or unsubstituted alkynyl, substituted or unsubstituted haloalkyl, substituted or unsubstituted hydroxyalkyl, substituted or unsubstituted alkoxy, a substituted or unsubstituted heterocyclic group, a substituted or unsubstituted aromatic group, a substituted or unsubstituted heteroaromatic group, carboxyl, alkylcarbonyl, arylcarbonyl, cycloalkylcarbonyl, heterocyclylcarbonyl, amino, aminoalkyl, alkylaminoalkyl, heterocyclylalkyl, aralkyl, arylalkenyl, arylalkynyl, alkylthio, alkylamino, arylamino, heteroarylamino, aralkylamino, alkylaminoalkylamino, arylthio, aralkylthio, aryloxy, aralkoxy, heterocyclylalkoxy, heterocyclyloxyalkyl, cycloalkyl, and cycloalkenyl. $R^3$ can be specifically, H or substituted or unsubstituted alkyl. In a further embodiment, $R^4$ is selected from a substituted or unsubstituted aromatic group, or a substituted or unsubstituted heteroaromatic group. The substituted aromatic group or heteroaromatic group can be substituted with at least one group (e.g. substituent) selected from halo, hydroxyl, amino, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group. The substituent can be more specifically selected from halo, hydroxyl, cyano, amino, nitro, substituted or unsubstituted alkyl, substituted or unsubstituted alkenyl, substituted or unsubstituted alkynyl, substituted or unsubstituted haloalkyl, substituted or unsubstituted hydroxyalkyl, substituted or unsubstituted alkoxy, a substituted or unsubstituted heterocyclic group, a substituted or unsubstituted aromatic group, a substituted or unsubstituted heteroaromatic group, carboxyl, alkylcarbonyl, arylcarbonyl, cycloalkylcarbonyl, heterocyclylcarbonyl, aminoalkyl, alkylaminoalkyl, heterocyclylalkyl, aralkyl, arylalkenyl, arylalkynyl, alkylthio, alkylamino, arylamino, heteroarylamino, aralkylamino, alkylaminoalkylamino, arylthio, aralkylthio, aryloxy, aralkoxy, heterocyclylalkoxy, heterocyclyloxyalkyl, cycloalkyl, and cycloalkenyl.

In a further embodiment of Formulae II or III, $R^4$ is selected from a substituted or unsubstituted aromatic group, a substituted or unsubstituted heteroaromatic group. More specifically, the substituted aromatic or heteroaromatic groups are substituted with at least one group selected from halo, hydroxyl, cyano, amino, aminoalkyl or nitro. In a further embodiment, $R^4$ is selected from a substituted or unsubstituted pyridinyl group or a substituted or unsubstituted phenyl group. The substituted or unsubstituted pyridinyl group can be a 2-pyridinyl, 3-pyridinyl, or 4-pyridinyl group. The substituted pyridinyl group can be substituted in the para position or the substituted phenyl group can be substituted in the ortho position. In a more specific embodiment, the substituted pyridinyl group is substituted with a chloro or fluoro or the substituted phenyl group is substituted with the hydroxyl, amino, or aminoalkyl.

In another embodiment of Formula I, $R^4$ and $R^5$ are each independently selected from a substituted or unsubstituted aromatic group, or a substituted or unsubstituted heteroaromatic group, wherein at least one of $R^4$ and $R^5$ is a halo-substituted aromatic group or a halo-substituted heteroaromatic group. R and $R^3$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group. More specifically, R and $R^3$ can be each independently selected from H, halo, hydroxyl, cyano, substituted or unsubstituted alkyl, substituted or unsubstituted alkenyl, substituted or unsubstituted alkynyl, substituted or unsubstituted haloalkyl, substituted or unsubstituted hydroxyalkyl, substituted or unsubstituted alkoxy, a substituted or unsubstituted heterocyclic group, a substituted or unsubstituted aromatic group, a substituted or unsubstituted heteroaromatic group, carboxyl, alkylcarbonyl, arylcarbonyl, cycloalkylcarbonyl, heterocyclylcarbonyl, amino, aminoalkyl, alkylaminoalkyl, heterocyclylalkyl, aralkyl, arylalkenyl, arylalkynyl, alkylthio, alkylamino, arylamino, heteroarylamino, aralkylamino, alkylaminoalkylamino, arylthio, aralkylthio, aryloxy, aralkoxy, heterocyclylalkoxy, heterocyclyloxyalkyl, cycloalkyl, and cycloalkenyl.

In a further embodiment of Formula I, $R^4$ and $R^5$ are each independently selected from a substituted or unsubstituted aromatic group, or a substituted or unsubstituted heteroaromatic group. The substituted aromatic group or heteroaromatic group can be substituted with at least one group (e.g. substituent) selected from halo, hydroxyl, amino, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, wherein at least one of $R^4$ and $R^5$ is a halo-substituted aromatic group or a halo-substituted heteroaromatic group. More specifically, $R^3$ can be H or substituted or unsubstituted alkyl. The substituent can be more specifically selected from halo, hydroxyl, cyano, amino, nitro, substituted or unsubstituted alkyl, substituted or unsubstituted alkenyl, substituted or unsubstituted alkynyl, substituted or unsubstituted haloalkyl, substituted or unsubstituted hydroxyalkyl, substituted or unsubstituted alkoxy, a substituted or unsubstituted heterocyclic group, a substituted or unsubstituted aromatic group, a substituted or unsubstituted heteroaromatic group, carboxyl, alkylcarbonyl, arylcarbonyl, cycloalkylcarbonyl, heterocyclylcarbonyl, aminoalkyl, alkylaminoalkyl, heterocyclylalkyl, aralkyl, arylalkenyl, arylalkynyl, alkylthio, alkylamino, arylamino, heteroarylamino, aralkylamino, alkylaminoalkylamino, arylthio, aralkylthio, aryloxy, aralkoxy, heterocyclylalkoxy, heterocyclyloxyalkyl, cycloalkyl, and cycloalkenyl.

In a further embodiment, $R^4$ and $R^5$ are each independently selected from a substituted aromatic group or heteroaromatic group. More specifically, the group is substituted with at least one group selected from halo, hydroxyl, cyano, amino, aminoalkyl or nitro. In a further embodiment, $R^4$ and $R^5$ are selected from a substituted or unsubstituted pyridinyl group or a substituted or unsubstituted phenyl group. The substituted or unsubstituted pyridinyl group can be a 2-pyridinyl, 3-pyridinyl, or 4-pyridinyl group. The substituted pyridinyl group can be substituted in the para position. In a more specific embodiment, the substituted pyridinyl group is substituted with a chloro or fluoro. The substituted pyridinyl group can be a substituted 2-pyridinyl group.

In further embodiments of Formula I, X is S.

With respect to the above-identified embodiments and, in general, the compound(s) encompassed by Formula I, R can be $NR^1R^2$, wherein $R^1$ and $R^2$ are each independently selected from H, halo, hydroxy, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, or $R^1$ and $R^2$ together form a substituted or unsubstituted heterocyclic group, a substituted or unsubstituted aromatic group, or a substituted or unsubstituted heteroaromatic group. More specifically, $R^1$ and $R^2$ together form a substituted or unsubstituted heterocyclic group. $NR^1R^2$ can be a substituted or unsubstituted piperazinyl group or pyridinyl group. In a specific embodiment, $NR^1R^2$ is:

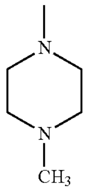

or

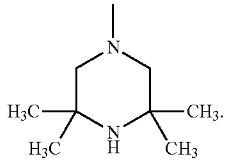

The compound described herein can be the compound of Formula I, a pharmaceutically-acceptable salt thereof, a hydrate thereof, a solvate thereof, a tautomer thereof, an optical isomer thereof, E-isomer thereof, Z-isomer thereof, or a combination thereof.

In specific embodiments, the compound of Formula I can be:

1A

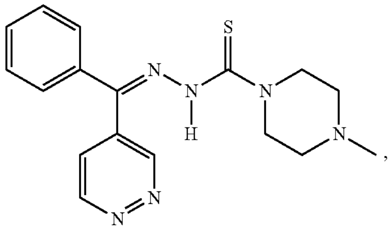

(COTI-4A)

1C

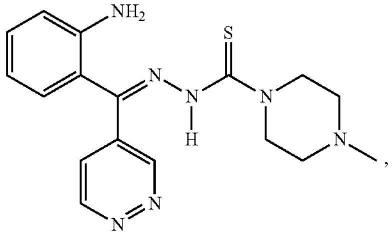

-continued

1D

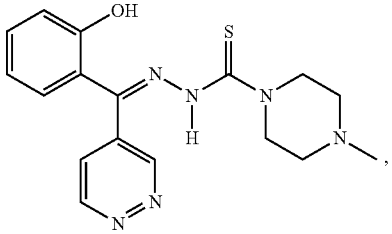

1E

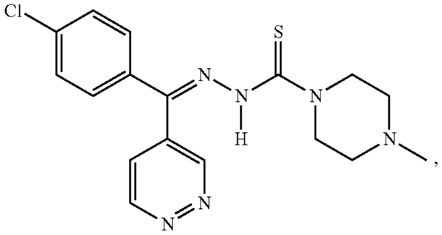

1F

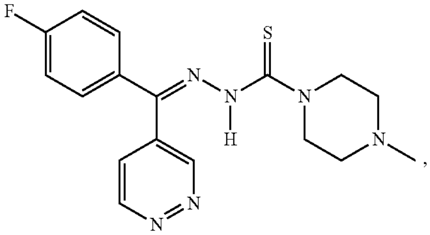

1G

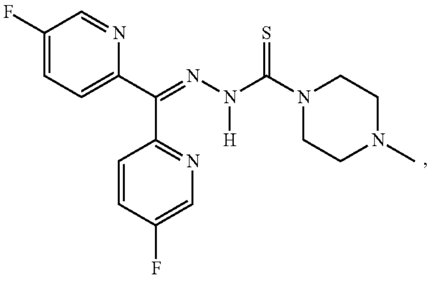

1H

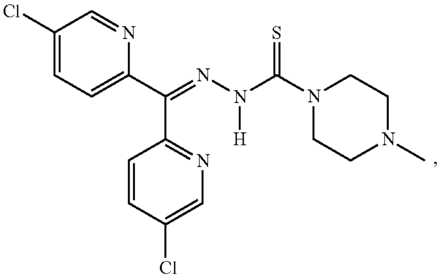

1I

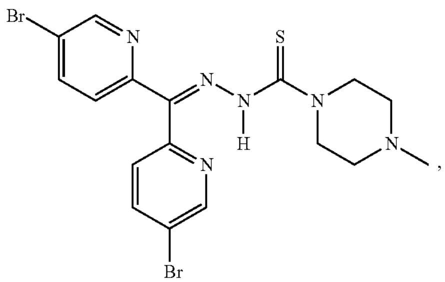

-continued

1J

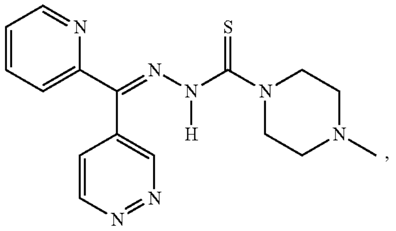

1K

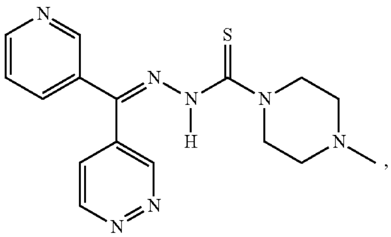

or

1L

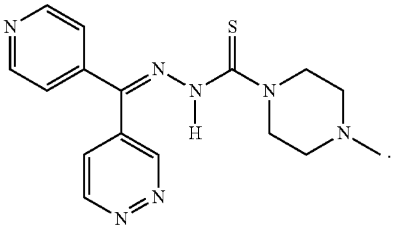

Such compounds may be used in the form of a pharmaceutically-acceptable salt, hydrate, solvate, an optical isomer thereof, E-isomer thereof, Z-isomer thereof, or a combination thereof.

The compounds of Formula I described herein can be prepared as follows:

a) reacting a compound of Formula IV with an amine $NHR^1R^2$ to form an intermediate of formula V:

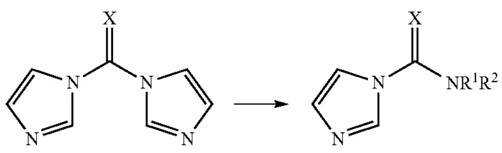

Formula IV

Formula V b) reacting the intermediate of Formula V with $NHR^3NH_2$ to form an intermediate of Formula VI:

Formula VI

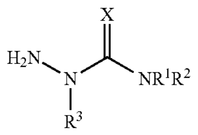

c) reacting the intermediate of Formula VI with a ketone:

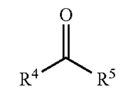

under condensation conditions, to form the compound of Formula I.

The compounds of Formulae II or III described herein can be prepared as follows:

a) reacting a compound of Formula IV with an amine $NHR^1R^2$ to form an intermediate of formula V:

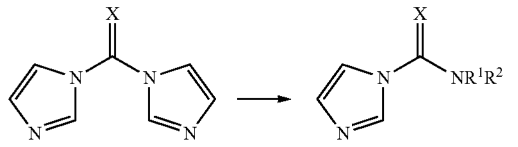

Formula IV Formula V b) reacting the intermediate of Formula V with $NHR^3NH_2$ to form an intermediate of Formula VI:

Formula VI

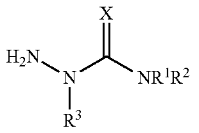

c) reacting the intermediate of Formula VI with a ketone:

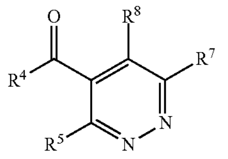

under condensation conditions, to form the compounds of Formulae II or III.

In a further embodiment, there is provided a compound of Formula VII:

Formula VII

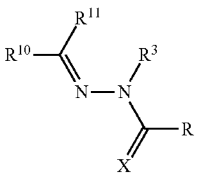

and/or a pharmaceutically-acceptable salt, hydrate, solvate, tautomer, optical isomer, E-isomer, Z-isomer, or combination thereof;

wherein:

X is selected from S or O;

R and $R^3$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and $R^{10}$ and $R^{11}$ are each independently selected from a substituted or unsubstituted aromatic group, or a substituted or unsubstituted heteroaromatic group.

In another embodiment of Formula VII, R and $R^3$ are each independently selected from H, halo, hydroxyl, cyano, substituted or unsubstituted alkyl, substituted or unsubstituted alkenyl, substituted or unsubstituted alkynyl, substituted or unsubstituted haloalkyl, substituted or unsubstituted hydroxyalkyl, substituted or unsubstituted alkoxy, a substituted or unsubstituted heterocyclic group, a substituted or unsubstituted aromatic group, a substituted or unsubstituted heteroaromatic group, carboxyl, alkylcarbonyl, arylcarbonyl, cycloalkylcarbonyl, heterocyclylcarbonyl, amino, aminoalkyl, alkylaminoalkyl, heterocyclylalkyl, aralkyl, arylalkenyl, arylalkynyl, alkylthio, alkylamino, arylamino, heteroarylamino, aralkylamino, alkylaminoalkylamino, arylthio, aralkylthio, aryloxy, aralkoxy, heterocyclylalkoxy, heterocyclyloxyalkyl, cycloalkyl, and cycloalkenyl.

In a further embodiment of Formula VII, $R^{10}$ and $R^{11}$ are each independently selected from a substituted or unsubstituted aromatic group, or a substituted or unsubstituted heteroaromatic group. The substituted aromatic group or heteroaromatic group can be substituted with at least one group (e.g. substituent) selected from halo, hydroxyl, amino, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group. More specifically, $R^3$ can be H or substituted or unsubstituted alkyl. The substituent can be more specifically selected from halo, hydroxyl, cyano, amino, nitro, substituted or unsubstituted alkyl, substituted or unsubstituted alkenyl, substituted or unsubstituted alkynyl, substituted or unsubstituted haloalkyl, substituted or unsubstituted hydroxyalkyl, substituted or unsubstituted alkoxy, a substituted or unsubstituted heterocyclic group, a substituted or unsubstituted aromatic group, a substituted or unsubstituted heteroaromatic group, carboxyl, alkylcarbonyl, arylcarbonyl, cycloalkylcarbonyl, heterocyclylcarbonyl, aminoalkyl, alkylaminoalkyl, heterocyclylalkyl, aralkyl, arylalkenyl, arylalkynyl, alkylthio, alkylamino, arylamino, heteroarylamino, aralkylamino, alkylaminoalkylamino, arylthio, aralkylthio, aryloxy, aralkoxy, heterocyclylalkoxy, heterocyclyloxyalkyl, cycloalkyl, and cycloalkenyl, more specifically, the substituent can be selected from halo, hydroxyl, cyano, amino, aminoalkyl or nitro.

In a further embodiment of Formula VII, $R^{10}$ and $R^{11}$ are each independently selected from a substituted or unsubstituted pyridinyl group or a substituted or unsubstituted phenyl group. More specifically, the group is substituted with at least one group selected from halo, hydroxyl, cyano, amino, aminoalkyl or nitro. In a further embodiment, $R^{10}$ and $R^{11}$ are selected from a substituted or unsubstituted pyridinyl group or a substituted or unsubstituted phenyl group. The substituted or unsubstituted pyridinyl group can be a 2-pyridinyl, 3-pyridinyl, or 4-pyridinyl group. The substituted pyridinyl group can be substituted in the para position. In a more specific embodiment, the substituted pyridinyl group is substituted with a chloro or fluoro. The substituted pyridinyl group can be a substituted 2-pyridinyl group.

In further embodiments of Formula VII, X is S.

With respect to the above-identified embodiments and, in general, the compound(s) encompassed by Formula VII, R can be $NR^1R^2$, wherein $R^1$ and $R^2$ are each independently selected from H, halo, hydroxy, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, or $R^1$ and $R^2$ together form a substituted or unsubstituted heterocyclic group, a substituted or unsubstituted aromatic group, or a substituted or unsubstituted heteroaromatic group. More specifically, $R^1$ and $R^2$ together form a substituted or unsubstituted heterocyclic group. $NR^1R^2$ can be a substituted or unsubstituted piperazinyl group or pyridinyl group. In a specific embodiment, $NR^1R^2$ is:

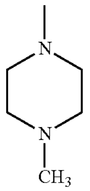

or

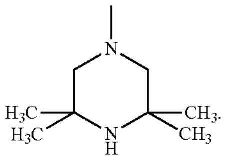

The compound described herein can be the compound of Formula VII, a pharmaceutically-acceptable salt thereof, a hydrate thereof, a solvate thereof, a tautomer thereof, an optical isomer thereof, E-isomer thereof, Z-isomer thereof, or a combination thereof.

In specific embodiments, the compound of Formula VII can be:

VIIA

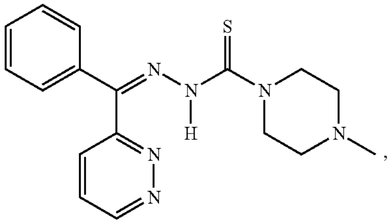

VIIB

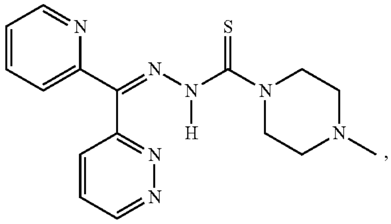

VIIC

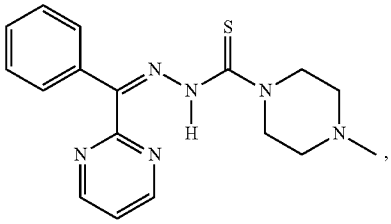

-continued

VIID

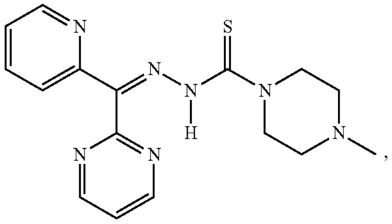

VIIE

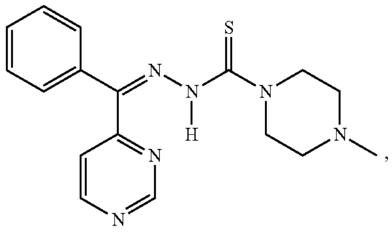

VIIF

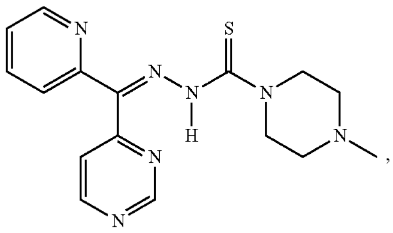

VIIG

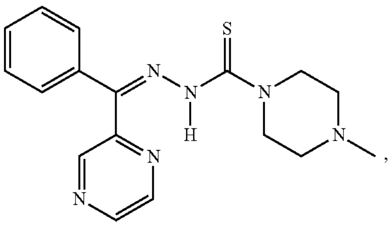

VIIH

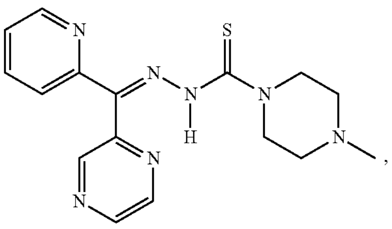

VII I

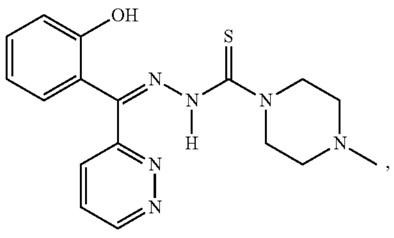

or

-continued

VII J

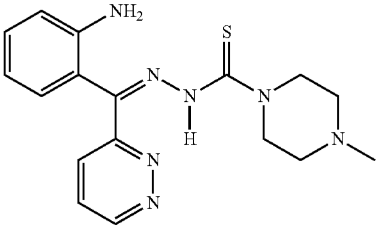

, or

1B

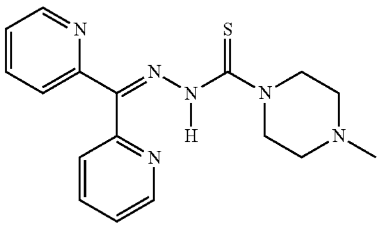

.

COTI-4 (or COTI-4MO5)

Such compounds may be used in the form of a pharmaceutically-acceptable salt, hydrate, solvate, an optical isomer thereof, E-isomer thereof, Z-isomer thereof, or a combination thereof.

The compounds of the present invention are useful in the treatment of cancer. High levels of activity for in vitro and in vivo testing have been observed against cancers and cancer models using the compounds of the present invention. This may lead to reduced dosages as compared with conventional therapeutic dosages of known agents.

The cancer treated may be, for example, lung cancer (particularly small cell or non-small cell lung cancer), cervical cancer, ovarian cancer, cancer of CNS, skin cancer, prostate cancer (e.g. hormone resistant prostate cancer), sarcoma, breast cancer, leukemia, colorectal cancer, head cancer, neck cancer, lymphoma, pancreatic cancer, gastric cancer, or kidney cancer. More typically, the cancer may be small cell lung cancer, breast cancer (e.g. hormone resistant breast cancer), acute leukemia, chronic leukemia, colorectal cancer. The cancer may be a carcinoma. The carcinoma may be selected from small cell carcinomas, cervical carcinomas, glioma, astrocytoma, prostate carcinomas, ovarian carcinomas, melanoma, breast carcinomas, or colorectal carcinomas. Compounds of the present invention may be even more particularly useful in the treatment of small cell lung cancer (SCLC) carcinomas.

Compounds of the present invention can have an $IC_{50}$ for a cancer cell population of less than or equal to about 10,000 nM. In specific embodiments, compounds of the present invention show efficacy against SHP77 cells at $IC_{50}$'s of less than about 1000 nM, typically less than about 800 nM, more typically less than about 500 nM, even more typically less than about 200 nM.

Compounds of the present invention show efficacy against DMS144 cells at $IC_{50}$'s of less than about 1000 nM, typically less than about 750 nM, more typically less than about 500 nM, even more typically less than about 300 nM, yet more typically less than about 100 nM.

Compounds of the present invention are effective in reducing the size of malignant human cancer tumors, particularly human small cell lung cancer tumors. Compounds of the present invention are effective in vitro at reducing the size of malignant human cancer tumors created from SHP77, DMS114, DMS-153 and/or DMS-253 small cell lung cancer lines.

Compounds of the present invention may exhibit a reduced tendency to induce cellular resistance to their own anti-cancer effects. Therefore, use of the compounds of the present invention to treat a cancer may inhibit or prevent development of a drug resistant form of that cancer.

Certain compounds of the present invention may exhibit reduced toxicity as compared with conventionally administered agents.

The compounds of this invention may be administered to mammals, typically humans, either alone or, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, and subcutaneous routes of administration.

Compounds of the present invention may be advantageously administered orally, unlike most current cancer therapies, which are administered intravenously. For oral use of a compound or composition according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

At least about 50% of the compound of the present invention can be orally absorbed by a mammal. In specific embodiments, at least about 60%; about 60% to about 85%; about 65%; about 70%; about 72%; about 73%, about 75%; about 80%; about 82%; or about 85% of the compound of the present invention can be orally absorbed by a mammal, more typically, a human. "Oral absorption" is used in the context of how the compound/composition of the present invention are delivered and absorbed into the blood. Typically, the compound/composition is administered orally and crosses a mucosal membrane of the gastro-intestinal tract, typically in the intestines. However, other methods of contacting the compounds/compositions of the present invention with the mucosal membrane of the gastro-intestinal tract may also be used.

The term "administration" (e.g., "administering" a compound) in reference to a compound of the invention means introducing the compound or a prodrug of the compound into the system of the animal in need of treatment. The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount from about 0.01 mg/kg of body weight to greater than about 100 mg/kg of body weight per day; from about 0.01 mg/kg of body weight to about 500 mg/kg of body weight per day; from about 0.01 mg/kg of body weight to about 250 mg/kg of body weight per day; or 0.01 mg/kg of body weight to about 100 mg/kg of body weight per day. These dosages can be more particularly used orally.

The compounds of this invention may be prepared by employing reactions and standard manipulations that are known in the literature or exemplified herein.

When introducing elements disclosed herein, the articles "a", "an", "the", and "said" are intended to mean that there are one or more of the elements.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Synthesis of COTI-4 (1B)

Synthesis of the compound of COTI-4 (1B) was conducted according to the following synthetic methodology:

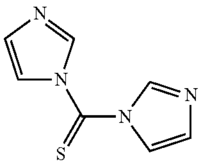

1

+

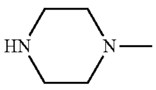

2

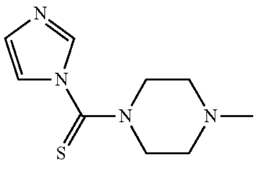

3

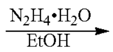

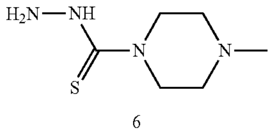

6

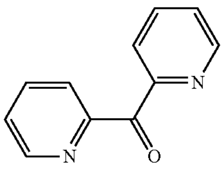

8

+

-continued

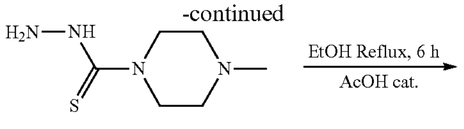

6

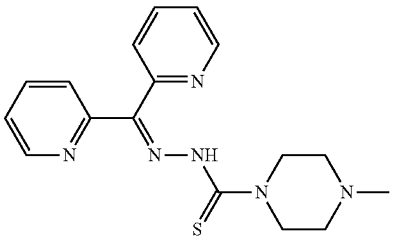

IB

Imidazol-1-yl-(4-methyl-piperazin-1-yl)-methanethione (intermediate 3) is formed as follows: N-Methyl piperazine (2; MW 100.16, 0.67 ml, 6.0 mmol, 1 eq) was added to a solution of 1,1'-thiocarbonyldiimidazole (1; MW 178.22, 1.069 g, 6.0 mmol, 1 eq) in 50 ml dichloromethane at room temperature. The reaction mixture was stirred overnight at room temperature. This organic solution was washed with water, dried over sodium sulfate, filtered and concentrated to provide imidazol-1-yl-(4-methyl-piperazin-1-yl)-methanethione (3; MW 210.30, 1.040 g, 4.95 mmol, 82% yield) and used without further purification. TLC ($CH_2Cl_2$/MeOH: 95/5) : Rf=0.35, Product UV and Ninhydrine stain active. $^1$H-NMR (400 MHz, $CDCl_3$), δ ppm: 2.37 (s, 3H), 2.56 (s, 4H), 3.94 (s, 4H), 7.11 (s, 1H), 7.21 (s, 1H), 7.88 (s, 1H).

4-methylpiperazine-1-carbothiohydrazide (intermediate 6) can be formed according to the following scheme. Hydrazine hydrate (MW 50.06, 0.26 ml, 5.44 mmol, 1.1 eq) was added to a solution of imidazol-1-yl-(4-methyl-piperazin-1-yl)-methanethione (3; MW 210.30, 1.040 g, 4.95 mmol, 1 eq) in 30 ml ethanol at room temperature. The reaction mixture was stirred under reflux for 2 hours. This organic solution was concentrated. The solid thus obtained was triturated with diethyl ether and filtered to yield 4-methylpiperazine-1-carbothiohydrazide (6; MW 174.27, 0.53 g, 3.04 mmol, 61% yield) as a white solid which was used without further purification. TLC ($CH_2Cl_2$/MeOH: 90/10): Rf=0.15, Product UV and Ninhydrin stain active. $^1$H-NMR (400 MHz, DMSO-$d_6$), δ ppm: 2.17 (s, 3H), 2.28 (t, 4H, J=5 Hz), 3.69 (t, 4H, J=5 Hz).

Finally, N'-(dipyridin-2-ylmethylidene)-4-methylpiperazine-1-carbothiohydrazide (COTI-4; 1B) was formed as follows: 4-methylpiperazine-1-carbothiohydrazide (6; MW 174.27, 0.349 g, 2.0 mmoles, 1 eq) and di-2-pyridyl ketone (8; MW 184.2, 0.368 g, 2.0 mmoles, 1 eq) was dissolved in 15 ml of ethanol at room temperature, in the presence of 1% of glacial acetic acid (MW 60.05, 0.15 ml, 2.6 mmoles, 1.3 eq). The mixture was stirred under reflux for 6 hours. After concentration, the crude thus obtained was taken up in dichloromethane, washed with a potassium carbonate aqueous solution, then with water. The organic layer was dried over sodium sulfate, filtered and concentrated. The crude was purified by ISCO CombiFlash™ Companion (Redisep™ cartridge 12 g, Normal phase, Gradient DCM/MeOH: 10/0 to 9/1) and provided N'-(dipyridin-2-ylmethylidene)-4-methylpiperazine-1-carbothiohydrazide (1B; MW 340.45, 0.230 g, 0.68 mmole, 68% yield) as a yellow-brown solid. MS [ESI+, 90/10 MeOH/$H_2O$ (5 mM $NH_4OAc$, 0.2% Acetic acid)]: $[M+H]^+$=341.0; $^1$H-NMR and HPLC analysis showed a mixture of isomers (approximately in 80/20 ratio), and >98% purity. $^1$H-NMR (400 MHz, $CDCl_3$), δ.ppm (Major isomer): 2.34 (s, 3H), 2.54 (t, 4H, J=5 Hz), 4.12 (t, 4H, J=5 Hz), 7.31 (dd, 1H, J=8 and 5 Hz), 7.37 (dd, 1H, J=8 and 5 Hz), 7.66 (d, 1H, J=8 Hz), 7.81 (m, 2H), 8.00 (d, 1H, J=8 Hz), 8.58 (d, 1H, J=5 Hz), 8.71 (d, 1H, J=5 Hz), 14.70 (s, 1H). δ ppm (Minor isomer): 2.34 (s, 3H), 2.54 (t, 4H, J=5 Hz), 4.12 (t, 4H, J=5 Hz), 7.23 (m, 1H), 7.30 (m, 1H), 7.68 (d, 1H, J=8 Hz), 7.75 (m, 2H), 7.87 (d, 1H, J=8 Hz), 8.54 (d, 1H, J=5 Hz), 8.68 (d, 1H, J=5 Hz), 14.70 (s, 1H).

Synthesis of COTI-4A (1A)

Synthesis of the compound of COTI-4A (1A) was conducted according to the following synthetic methodology:

Synthon A Synthon B

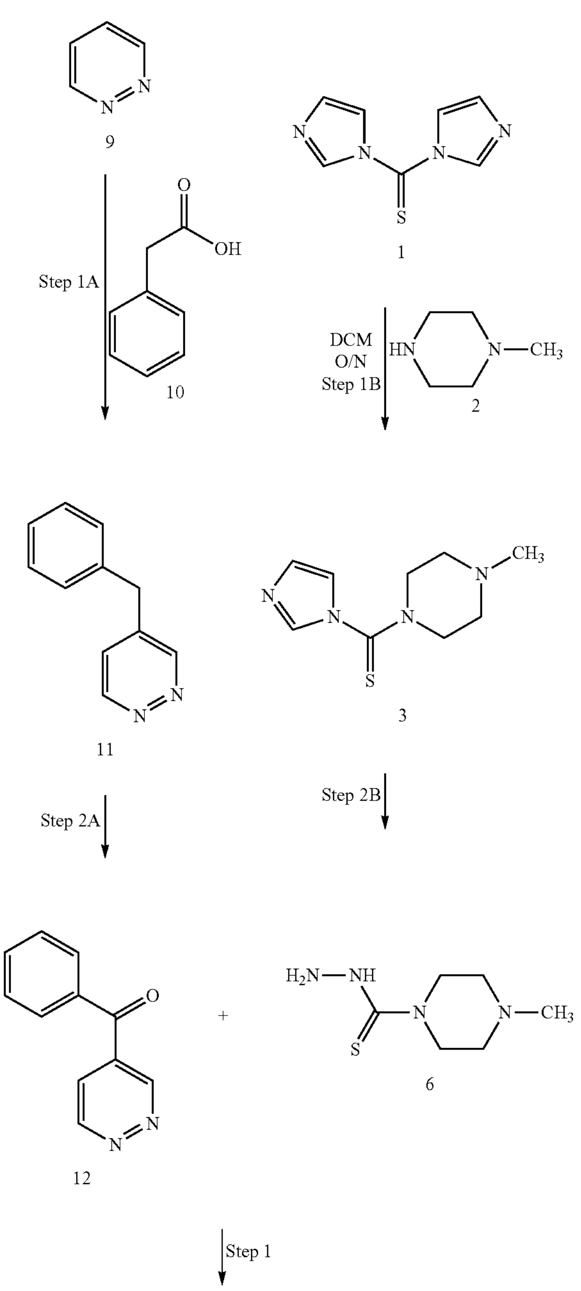

-continued

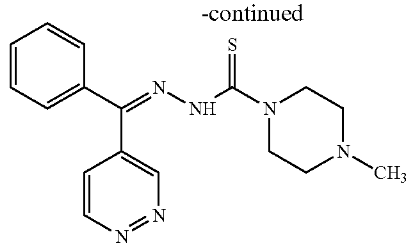

1A

Synthesis of Synthon A

Step 1A: 4-Benzylpyridazine (11)

To a 70° C. solution of pyridazine (9; 10 g, 0.125 mole) in aqueous $H_2SO_4$ (2N,125 mL) was added $AgNO_3$ (6.37 g, 0.0375 mole). Phenylacetic acid (10; 85.06 g 0.625 mole) was added to the mixture. The reaction mixture was stirred vigorously at 70° C. for 20 minutes and was degassed with a flow of nitrogen for 2 minutes, followed by a slow portionwise addition of ammonium persulfate (85.62, 0.375 mole) with rapid gas evolution. The reaction mixture was then heated at 90° C. for 30 minutes. The reaction mixture was then cooled at room temperature and the solution was extracted with $CH_2Cl_2$. A 50% NaOH solution was added to the aqueous phase, which was re-extracted with $CH_2Cl_2$ twice. The combined extracts were dried over MgSO4. The solvent was evaporated to dryness and the residue was purified by silica gel chromatography using $CH_2Cl_2$/5% methanol as the eluent. The yield of 4-benzylpyridazine (11) obtained was 8.2 g or 39%. MS (ESI+): [M+H]+=171.47; $^1$H NMR (300 MHz, $CDCl_3$), δ ppm: 4.0 (s,2H), 7.18-7.4 (m, 6H), 9.02-9.18 (m, 2H).

Step 2A: Phenyl-Pyridazin-4-yl-Methanone (12)

To a 100° C. suspension of $SeO_2$ (4.75 g, 0.043 mole) in acetic acid (216 mL) was added dropwise to a solution of 4-benzylpyridazine (11; 7.6 g, 0.044.6 mole) in acetic acid (216 mL). The mixture was heated for 1 hour at 100° C. The reaction mixture was cooled to room temperature and was neutralized to a pH ~6-7 with 50% NaOH. The neutralized mixture was extracted twice with $CH_2Cl_2$. The combined extracts were dried over $MgSO_4$ and were evaporated to dryness. The crude product was purified by crystallization in refluxing isopropyl alcohol (10 vol). The yield of phenylpyridazin-4-yl-methanone (12) obtained was 5.8 g or 66%. MS (ESI+): [M+H]+=185.33; $^1$H NMR (300 MHz, $CDCl_3$), δ ppm: 7.5-7.60(m, 2H), 7.64-7.83 (m, 4H), 9.42-9.51 (m, 2H).

Synthesis of Synthon B

Step 1B: Imidazol-1-yl-(4-Methyl-2-yl-Piperazin-1yl)-Methanethione (3)

1-Methylpiperazine (2; 3.28 g, 32.8 mmoles, 1 eq.) was added to a solution of 1,1'-thiocarbonyldiimidazole (3; 6.5 g, 32.8 mmoles, 1 eq.) in dichloromethane (200 mL) at room temperature (RT). After stirring overnight at RT the mixture was washed with water, was dried over sodium sulfate, was filtered and was concentrated to provide imidazol-1-yl-(4-methyl-piperazin-1-yl)-methanethione (3). The yield was 99.43%. MS (ESI+): the product was not stable at high temperature. $^{1}$HNMR (300 MHz, $CDCl_3$), δ ppm: 2.27 (s, 3H), 2.40 (s, 4H), 2.60 (s, 4H), 7.0-7.4 (s, 2H), 7.8-8.00 (s,1H).

Step 2B: (N-Methyl piperazine)Carbothioacid Hydrazide (6)

To a solution of imidazol-1yl-(4-methyl-piperazin-1-yl)-methanethione (3; 3.64 g, 17.3 mmoles 1 eq.) in 70 ml of ethanol at RT was added hydrazine hydrate (0.953 g, 19.03 mmoles, 1.1 eq.). The reaction was stirred and refluxed for 2 hours during which time a white precipitate formed. The white precipitate (N-methylpiperazine)carbothioacid hydrazide (6)) was filtered off and was rinsed with t-butyl methyl ether. The yield was 72%. MS (ESI+): 175; $^{1}$H NMR (300 MHz, $CDCl_3$), δ ppm: 2.0 (s, 1H), 2.27 (s, 3H), 2.40 (s, 4H), 3.8 (s, 4H), 4.4 (s, 2H).

Synthesis of COTI-4A (1A)

Step 1: 4-methyl-N'-[phenyl(pyridazin-4-yl)methylidene]piperazine-1-carbothiohydrazide (1A)

A mixture of phenyl-pyridazin-4-yl-methanone (12; Synthon A, 2.3 g, 12.4 mmol) and 4-Methylpiperazine-1-carbothioic acid hydrazide (6; Synthon B, 2.82 g, 16.18 mmol) in ethanol (7.5 mL) was heated to 65° C. for 5 h under $N_2$ in a 50 mL pyrex tube equipped with a screw cap. The mixture remained heterogeneous during the heating and a brown suspension resulted at the end of the reaction. The mixture was diluted with $CH_2Cl_2$ (7.5 mL) and was chromatographed on silica gel that was eluted with $MeOH/CH_2Cl_2$ (2.5-5%) to give 1.8 g of a yellow foamy solid 1A (99.3% pure by HPLC); m.p. 141-143° C. (m.p. of a crystalline sample 143-145). TLC ($CH_2Cl_2/MeOH/NH_4OH$:95/5/0.5): $R_f$=0.6, product is visibly yellow, UV and Dragendorff stain active. MS (ESI+): [M+H]+=340.93. HRMS: m/z calcd. for $C_{17}H_{21}N_6S$ ([M+H]+): 341.15429; found: 341.15501. $^{1}$H NMR (300 MHz, $CDCl_3$), δ ppm: 2.38 (s, 3H), 2.61 (t, 4H, J=5.0 Hz), 4.12 (t, 4H, J=5.0 Hz), 7.29 (m, 3H), 7.63 (m, 3H), 8.64 (s, 1H), 9.14 (dd, 1H, J=5.7 Hz, J'=1.5 Hz), 9.44 (dd, 1H, J=2.4 Hz, J'=1.5 Hz). $^{13}$C NMR (75.4 MHz, $CDCl_3$), δ ppm: 45.75, 51.64, 54.75, 123.30, 128.29, 128.39, 130.40, 131.10, 134.86, 143.94, 148.31, 151.31, 181.49.

Example 1

COTI-4 (1B)

$IC_{50}$ and Dose Response Determination

The ability of the compounds of Formula VII to inhibit tumor cell growth in vitro of three (3) human small cell lung cancer cell lines and three (3) human non-small cell lung cancer cell lines was evaluated. Specifically, COTI-4 (1B, also referred to as COTI-4MO5) was tested.

Table 1 shows the $IC_{50}$, or the molar concentration of the compound required to produce 50% of the maximum possible inhibitory response. As a comparative example, Gleevec® (imatinib mesylate, Novartis Pharmaceutical Inc.) was used. Gleevec® is an FDA-approved anti-tumor drug for chronic myelogenous leukemia, which acts as an ATP-analog to inhibit tyrosine kinase. In DMS-114, DMS-153 and SHP-77 SCLC tumor cells, compound COTI-4MO5 (1B) was found to be more effective than Gleevec®.

TABLE 1

COTI-4M05 Inhibition of Human SCLC Cell Lines

| | $IC_{50}$ (nM) | | |
|---|---|---|---|
| Cell line | DMS-114 | DMS-153 | SHP-77 |
| COTI-4M05 | 30 | 130 | 173 |
| Gleevec ® | 15,733 | 14,041 | 18,835 |

Figure 1:
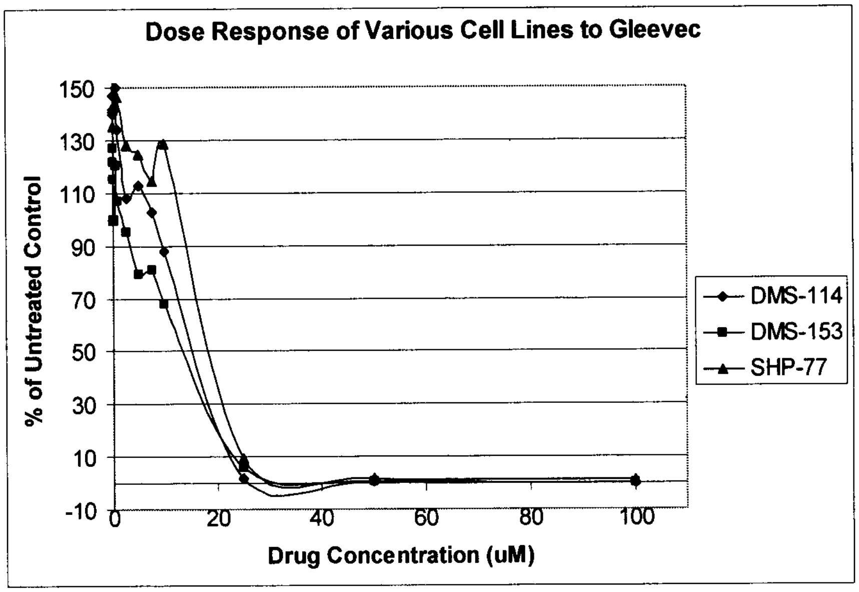
FIG. 1 shows the dose response of three human SCLC tumor cell lines (DMS-114, DMS-153 and SHP-77) to Gleevec®, as a comparison to FIG. 2.
Figure 2:
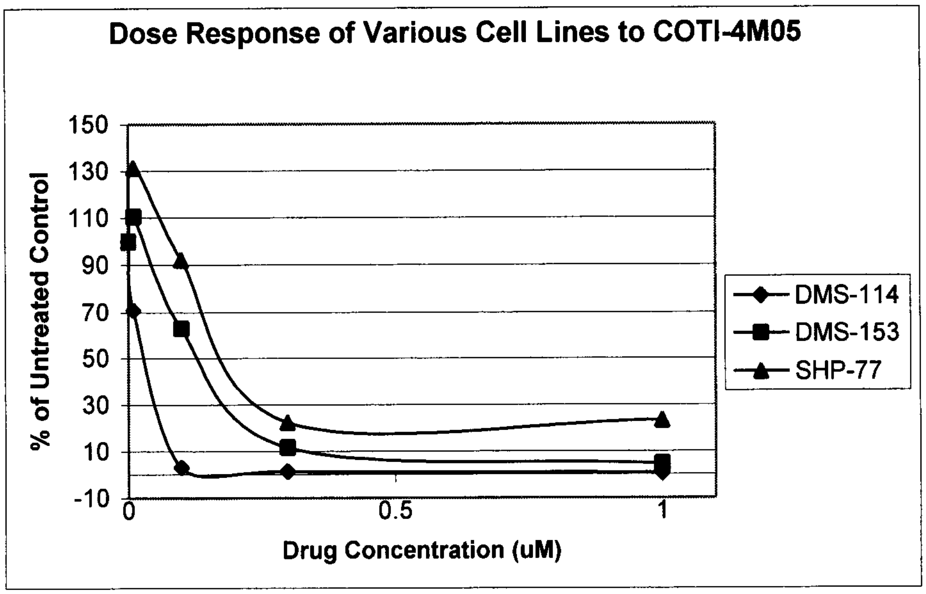
FIG. 2 shows the dose response of human SCLC tumor cell lines to "COTI-4" according to the invention.

FIG. 1 illustrates the dose response of three human SCLC tumor cell lines (DMS-114, DMS-153 and SHP-77) to Gleevec®, for comparison to FIG. 2.

FIG. 2 illustrates the dose response of human SCLC tumor cell lines to COTI-4MO5 (1B).

Figure 3:
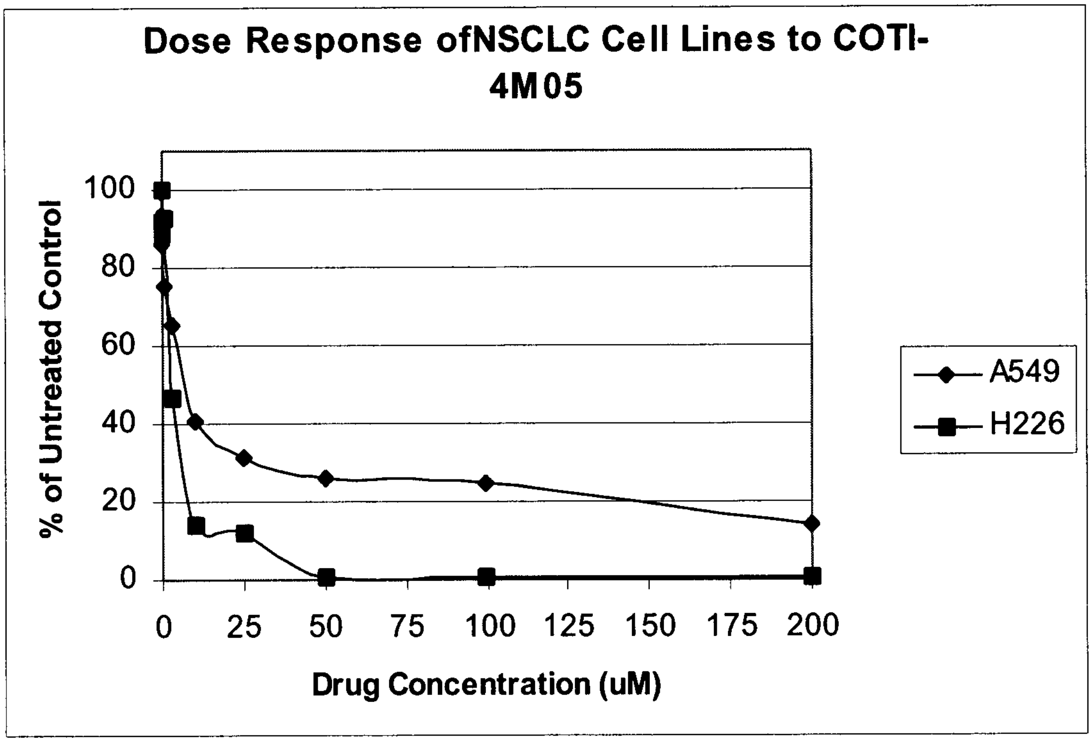
FIG. 3 shows the dose response of NSCLC tumor cell lines to "COTI-4" according to the invention.

FIG. 3 illustrates the dose response of NSCLC tumor cell lines to COTI-4MO5 (1B).

The capacity of the compound COTI-4, to inhibit growth of human small cell lung cancer cell lines (DMS-114, DMS-153, and SHP-77) and human non-small cell lung cancer cell lines (A549 adenocarcinoma-derived cells, H226 squamous cell carcinoma-derived cells, and A460 large cell carcinoma-derived cells) was tested.

In vitro inhibition of small cell lung cancer (SCLC) cell lines by the compound of COTI-4 was done with standard human tumor cells (established cell lines available from the American Type Tissue culture collection). Cells were plated in plastic tissue culture plates and grown under standard conditions for each cell line, in carbon dioxide/oxygen atmosphere in plastic tissue culture plates, in the presence of each of the compound of COTI-4, as well as COTI-2MO5 (or COTI-2) and COTI-219MO5 (or COTI-219) compounds (0-1 mM), versus Gleevec® (0-100 mM) at 35° C. for 3 days. Control cultures were treated with vehicle minus compound or Gleevec®. Cells were counted after 3 days in culture and at a cell density of no more than 80%.

FIGS. 1 to 3 show cell numbers for the different cell lines after treatment with various concentrations of compounds.

Concentrations of the COTI-4 (COTI-4MO5) and Gleevec® that inhibit growth of 3 human small cell lung cancer cell lines by 50% are shown in Table 1. Note that the compound of COTI-4 is over 100 times more effective than Gleevec® against these cell lines in vitro.

The compound of COTI-4 inhibits growth and/or kills SCLC cells with $IC_{50}$ values that are at least 0.03 mM and generally less than 1 mM. On the other hand, Gleevec® has an $IC_{50}$ value of 15-19 mM, depending on cell line tested. $IC_{50}$ values in the micromolar range, as seen here, indicate high capacity of the compound of formula 1B to inhibit human tumor cell growth.

In vitro inhibition of non-small cell lung cancer (NSCLC) cell lines by the compound of Formula 1B (COTI-4) was evaluated. Standard numbers of human tumor cells (established cell lines available from the American Type Tissue culture collection) were plated in plastic tissue culture plates and grown under standard conditions for each cell line, in carbon dioxide/oxygen atmosphere in plastic tissue culture plates, in the presence of COTI-4 (0-1 mM) or Gleevec® (0-100 mM) at 35° C. for 3 days. Control cultures were treated with vehicle minus compound or Gleevec®. Cells were counted after 3 days in culture and at a cell density of no more than 80%.

FIG. 3 depicts a graph showing cell numbers after treatment with various concentrations of the compound of 1B. The summary data of the concentrations required to inhibit growth by 50% are presented in Table 2.

TABLE 2

| COTI-4M05 Inhibition of Human NSCLC Cell Lines | | | |
|---|---|---|---|
| | $IC_{50}$ (nM) | | |
| Cell line | A549 | H226 | A460 |
| COTI-4M05 | 6,800 | 2,500 | 5,100 |
| Gleevec ® | 53,000 | 72,000 | 81,000 |

COTI-4M05 inhibits growth and/or kills NSCLC cells with $IC_{50}$ values of at least 2.5 mM. Thus, the selected compound of COTI-4MO5 is effective against NSCLC cell lines, but less so than against SCLC cell lines. COTI-4MO5 was more effective than Gleevec® against NSCLC cell lines.

Example 2

COTI-4

Inhibition of Tumor Growth

In vivo testing of the capacity of COTI-4MO5 and Taxol® (paclitaxel, Bristol Myers Squibb) to inhibit the growth of human SHP-77 SCLC cells as xenograft in immunocompromised mice was evaluated.

SHP-77 SCLC cells were grown in culture and injected into each flank of NCr-nu mice (T cell-deficient immunocompromised mice, suitable for growth of this cell line) ($2\times10^6$ cells per injection, in Matrigel™). Mice harbouring SHP-77 tumour xenografts were treated with COTI-2MO5 or COTI-4MO5, as described for the data shown in FIG. 4. One day after injection of tumour cells, groups of 5 mice each were injected with 3 mg/kg of COTI-2MO5 or COTI-4MO5 (i.p.), once every 2 days, up to 38 days. Tumour size was estimated at 5, 10, 17, 24, and 38 days, by external caliper measurement. Animals were humanely euthanized after the 38 day tumour measurement.

Figure 4:
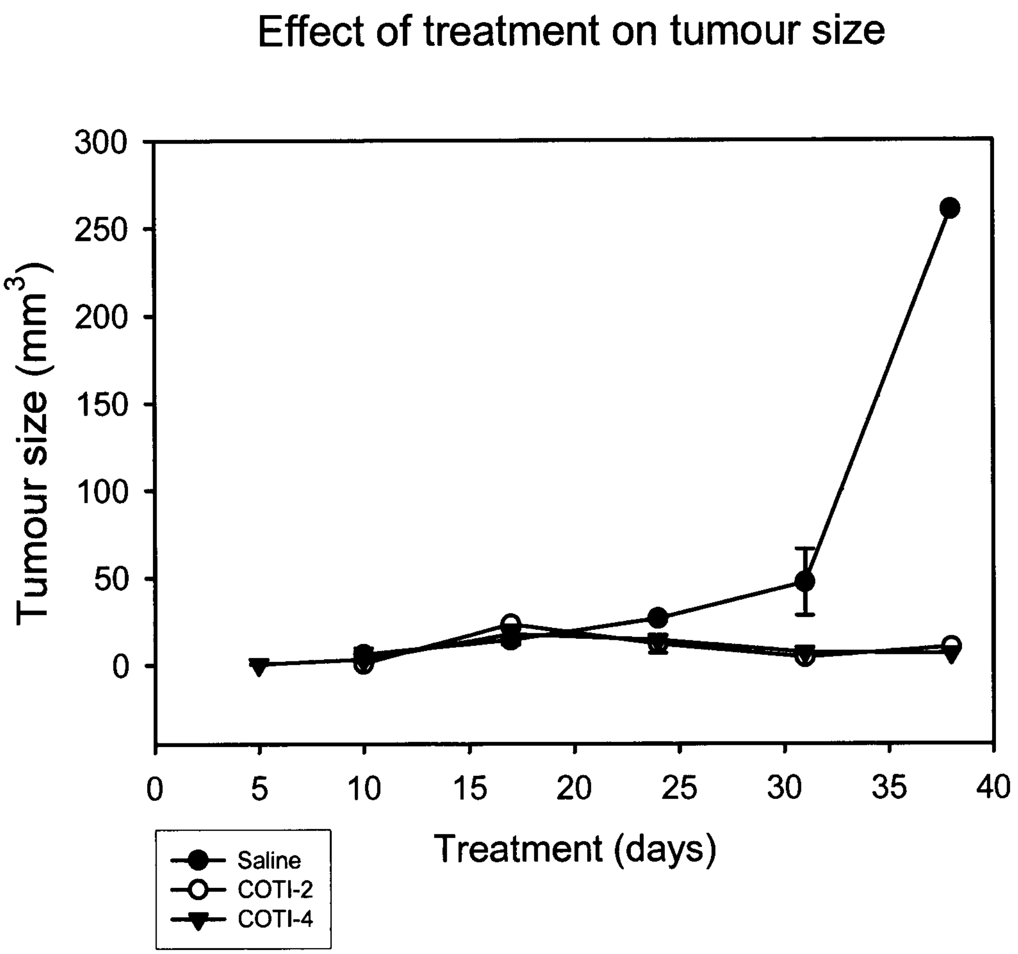
FIG. 4 shows the effect of a compound according to the invention, referred to herein throughout interchangeably as "COTI-4", "COTI-4MO5" or "Formula 1B", in inhibiting tumor growth over 38 days of treatment. Also depicted for comparison is a saline control, and compound referred to as "COTI-2", also described as "COTI-2M05", which is the subject of a co-pending U.S. Provisional Patent Application 60/884,504, now International Publication No. WO 2008/083491, published on Jul. 17, 2008, both of which are hereby incorporated by reference.

FIG. 4 depicts the effect of a compound, referred to herein interchangeably as COTI-4, COTI-4MO5, or the compound of formula 1B, in inhibiting tumor growth over 38 days of treatment. Also depicted for comparison is a saline control, and compound referred to as COTI-2, which is the subject of a co-pending patent application, U.S. Provisional Patent Application 60/884,504, incorporated herein by reference. Data are shown (each data point is the mean size of 3-10 tumours±SE) in FIG. 4.

The mean tumour size in mice treated with COTI-2MO5 or COTI-4MO5 is significantly lower than in mice treated with saline vehicle ($p<0.05$).

For comparison, mice (5 mice per group, injected as described above with SHP-77 human tumor cells as described above) and harbouring SHP-77 xenografts were treated with Taxol® (12.5 mg/kg, i.p. in 0.5 ml isotonic saline) every 2 days (according to the report of J. Riondel et al., Anticancer Res. 8:387-90, 1988) or with cisplatin (3.0 mg/kg of DDP i.p., once per week for four weeks, in isotonic saline, according to the report of P. A. Andrews et al., Cancer Commun. 2:93-100, 1990). Tumour size was estimated at 5, 10, 17, 24, and 38 days, by external caliper measurement. Animals were humanely euthanized after the 38 day tumour measurement.

Figure 5:
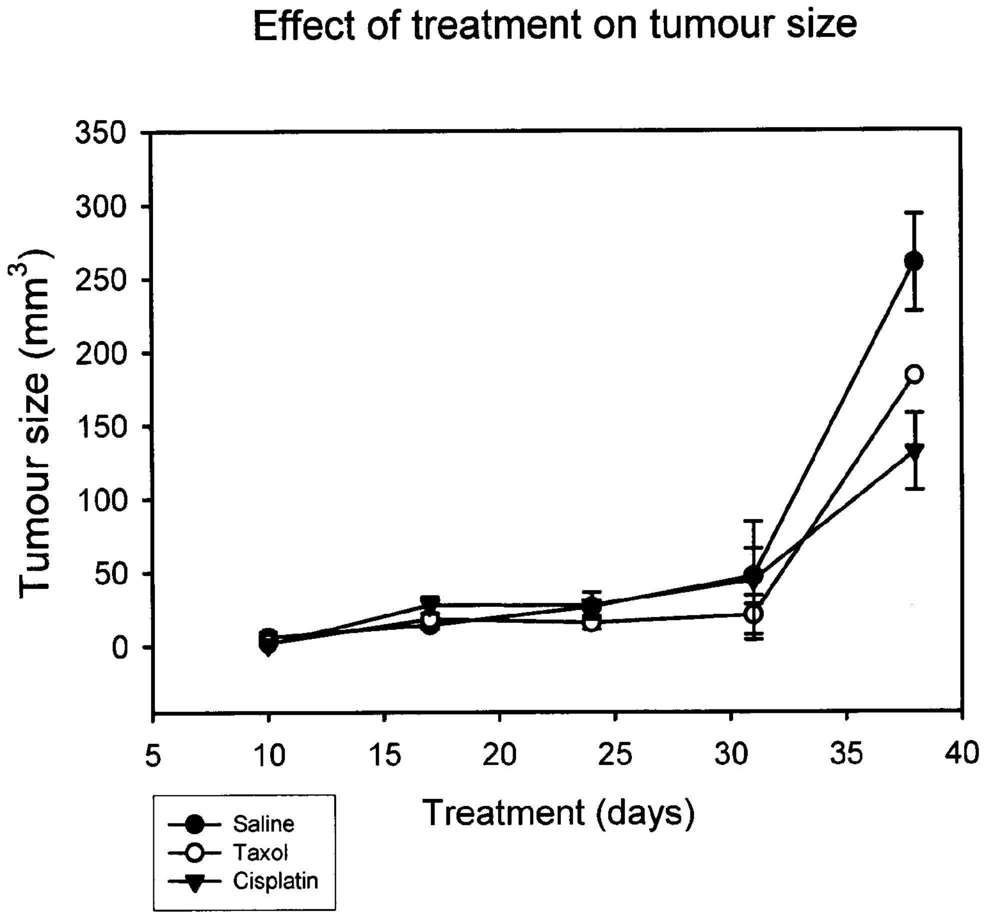
FIG. 5 is a comparative example, when viewed against data presented in FIG. 4, showing the effect on tumor growth of Taxol® and cisplatin treatment against a saline control.

FIG. 5 allows comparison, when viewed against data presented in FIG. 4, showing the effect on tumor growth of Taxol® and cisplatin treatment against a saline control. Data are shown (each data point is the mean size of 4-10 tumours±SE) in FIG. 5.

Tumour size in both Taxol®- and cisplatin-treated mice was significantly lower than in saline-treated mice ($p<0.05$).

Figure 6:
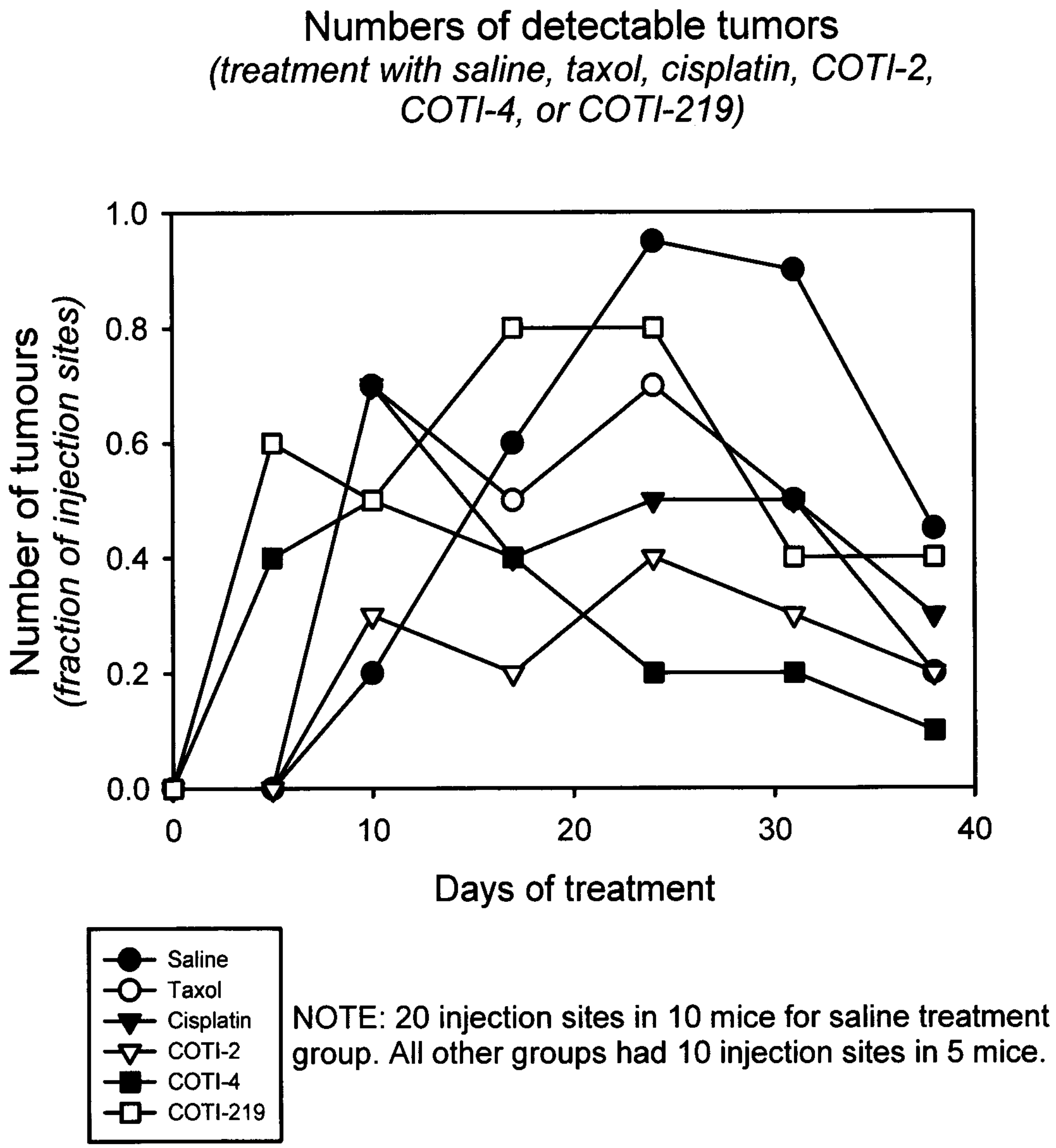
FIG. 6 shows the number of tumors, expressed as a fraction of injection sites after 38 days of treatment with COTI-4, according to the invention, versus saline (as a control), Taxol® and cisplatin comparative controls. Also depicted are results from compounds referred to as "COTI-2", as referenced above, and "COTI-219", also described as "COTI-219M05", which is the subject of co-pending U.S. Provisional Patent 60/884,489, which is also incorporated herein by reference.

FIG. 6 illustrates numbers of detectable tumors. When numbers of tumours (rather than tumour size) was plotted for all treatment groups, it was apparent that numbers of tumours in control (saline-treated) mice reached a maximum at day 24 post-tumour cell injection, and decreased thereafter. The maximum number of tumours in mice treated with Taxol®, cisplatin, COTI-219MO5, COTI-4MO5, and COTI-2MO5 were all lower than that in control, saline-treated mice. The data are not subject to analysis of significance since single aggregate numbers of tumours at each day of treatment were available.

FIG. 7 shows the average weight of animals treated with COTI-4M05, versus saline (as a control), Taxol® and cisplatin comparative controls. Also depicted are results from compounds referred to as "COTI-2M05", and "COTI-219M05", which are each the subject of co-pending U.S. Provisional Patent Applications 60/884,504 and 60/884,489, respectively, both provisionals are incorporated herein by reference.

Small cell lung cancer tumor size was determined and expressed as mean tumor volume. For COTI-4M05, mean tumor volume was 6.2 $mm^3$, whereas values were much greater for cisplatin (132±26 $mm^3$), Taxol® (183 $mm^3$) and control (saline) treated tumors (260±33 $mm^3$).

Example 3

COTI-4A (1A)

$IC_{50}$ and Dose Response Determination

The ability of compounds of COTI-4A (1A) to inhibit tumor cell growth in vitro of three (3) human small cell lung cancer cell lines and three (3) human non-small cell lung cancer cell lines was evaluated.

The capacity of the compounds of formula 1A to inhibit growth of human small cell lung cancer cell lines (DMS-114, DMS-153, and SHP-77) and human non-small cell lung cancer cell lines (A549 adenocarcinoma-derived cells, H226 squamous cell carcinoma-derived cells, and H460 large cell carcinoma-derived cells) was tested.

In vitro inhibition of small cell lung cancer (SCLC) cell lines by the compound of formula 1A was done with standard human tumor cells (established cell lines available from the American Type Tissue culture collection). Cells were plated in plastic tissue culture plates and grown under standard conditions for each cell line, in carbon dioxide/oxygen atmosphere in plastic tissue culture plates, in the presence of the compounds of Formula 1A versus Gleevec® (0-100 mM) at 35° C. for 3 days. Control cultures were treated with vehicle minus compound or Gleevec®. Cells were counted after 3 days in culture and at a cell density of no more than 80%.

FIGS. 8 to 10 show cell numbers for the different small cell lung cancer cell lines after treatment with various concentrations of compounds according to Formula 1A.

FIG. 8 illustrates the dose response of human SCLC cell line DMS-114 to COTI-4A. The two different lots relate to replicate experiments.

FIG. 9 illustrates the dose response of human SCLC cell line DMS-153 to COTI-4A. The two different lots relate to replicate experiments.

FIG. 10 illustrates the dose response of human SCLC cell line SHP-77 to COTI-4A. The two different lots relate to replicate experiments.

Concentrations of the compounds of Formula 1A and Gleevec® that inhibit growth of the 3 human small cell lung cancer cell lines by 50% were determined and are shown in Table 3.

TABLE 3

| COTI-4A Inhibition of Human SCLC Cell Lines | | | |
|---|---|---|---|
| | $IC_{50}$ (nM) | | |
| Cell line | DMS-114 | DMS-153 | SHP-77 |
| COTI-4A | 650 | 400 | 10,000 |
| Gleevec ® | 15,733 | 14,041 | 18,835 |

COTI-4A inhibits growth and/or kills SCLC cells with $IC_{50}$ values of at least 0.65 mM. It can be seen from Table 3 that COTI-4A is two orders of magnitude (about 100 times) more effective in vitro than Gleevec® against the two human SCLC cell lines DMS-114 and DMS-153 and about twice as effective as Gleevec® against human SCLC cell line SHP-77. SHP-77 is a notoriously difficult cell line to treat for most drugs, as evidenced by the higher $IC_{50}$'s for all drugs tested.

In vitro inhibition of non-small cell lung cancer (NSCLC) cell lines by the compound of Formula 1A is evaluated. Standard numbers of human tumor cells (established cell lines available from the American Type Tissue culture collection) were plated in plastic tissue culture plates and grown under standard conditions for each cell line, in carbon dioxide/oxygen atmosphere in plastic tissue culture plates, in the presence of compounds of formula 1A (0-1 mM) or Gleevec® (0-100 mM) at 35° C. for 3 days. Control cultures are treated with vehicle minus compound or Gleevec®. Cells are counted after 3 days in culture and at a cell density of no more than 80%.

FIGS. 11 to 13 show cell numbers for the different non-small cell lung cancer cell lines after treatment with various concentrations of compounds according to Formula 1A.

FIG. 11 illustrates the dose response of human non-SCLC cell line A-549 to COTI-4A. The two different lots relate to replicate experiments.

FIG. 12 illustrates the dose response of human non-SCLC cell line H-226 to COTI-4A. The two different lots relate to replicate experiments.

FIG. 13 illustrates the dose response of human non-SCLC cell line H-460 to COTI-4A. The two different lots relate to replicate experiments.

Concentrations of the compound of Formula 1A and Gleevec® that inhibit growth of the 3 human non-small cell lung cancer cell lines by 50% were determined and are shown in Table 4.

TABLE 4

| COTI-4A Inhibition of Human NSCLC Cell Lines | | | |
|---|---|---|---|
| | $IC_{50}$ (nM) | | |
| Cell line | A549 | H226 | A460 |
| COTI-4A | 1500 | 90,000 | 100,000 |
| Gleevec ® | 53,000 | 72,000 | 81,000 |

COTI-4A inhibits growth and/or kills NSCLC cells with $IC_{50}$ values of at least 1.5 mM. Thus, COTI-4A is effective against NSCLC cell lines, but less so than against SCLC cell lines. COTI-4A was more effective than Gleevec® against the NSCLC cell lines A549 and had comparable efficacy to Gleevec® for the other NSCLC cell lines that were tested, H226 and A460.

Example 4

In-silico Assessment of Properties

An in-silico assessment of the properties of compounds according to the present invention was performed using the CHEMSAS® computational platform. CHEMSAS® is a robust proprietary computational platform for accelerated drug discovery, optimization and lead selection based upon a unique combination of traditional and modern pharmacology principles, statistical modeling and machine learning technologies. At the centre of the CHEMSAS® platform is a hybrid machine learning technology that may be used to: find, profile and optimize new targeted lead compounds; find novel uses for known compounds; and, solve problems with existing or potential drugs. In using the CHEMSAS® platform, first a therapeutic target was selected, in this case cancer and more particularly Small Cell Lung Cancer. The second step involved the design of a candidate molecule library containing thousands of potential compounds through the assembly of privileged molecular fragments. Thirdly, the candidate library was profiled and optimized using a combination of validated computational models and traditional expert medicinal chemistry. In this step, the CHEMSAS® platform developed 244 molecular descriptors for each candidate therapeutic compound. For example, molecular properties relating to a candidate compound's therapeutic efficacy, expected human toxicity, oral absorption, cumulative cellular resistance and/or kinetics were assessed. In some instances, comparative properties relating to commercially relevant benchmark compounds were also assessed. Potential lead compounds were then selected from the candidate library using a proprietary decision making tool designed to identify candidates with the optimal physical chemical properties, efficacy, ADME/Toxicity profile, etc. according to a pre-determined set of design criteria. The lead compounds selected from the candidate library were then synthesized for further pre-clinical development.

The properties of certain compounds according to the present invention, specifically COTI-4 (1B), COTI-4A (1A), and Formulae 1C, 1D, 1G, 1H, 1I, and VIIA to VIIJ, that were assessed in-silico using the CHEMSAS® computational platform are shown in Tables 5 to 8. Some of the predicted properties are validated by the experimental data provided herein; while other properties have been validated elsewhere during the development of other clinical candidates. The CHEMSAS® platform therefore provides a means of determining, predicting and/or testing the properties of a compound, particularly when used to determine the properties of compounds according to the present invention. The CHEMSAS® platform is also particularly useful in comparing the properties of compounds according to the invention with prior art compounds on a relative basis in silico.

Tables 5A and 5B: Physical Chemical Properties

Tables 5A and 5B shows that COTI-4 (1B), COTI-4A (1A), and Formulae 1C, 1D, 1G, 1H, 1I, and VIIA to VIIJ are "drug-like" with good drug like physical properties.

TABLE 5A

| Mol ID | FORMULA | Mol-Weight | MnLogP | HBndDon | HBndAcc |
|---|---|---|---|---|---|
| 1B | $C_{17}H_{20}N_6S$ | 340.45 | 1.67 | 1 | 6 |
| 1G | $C_{17}H_{18}F_2N_6S$ | 376.43 | 2.44 | 1 | 6 |
| 1H | $C_{17}H_{18}Cl_2N_6S$ | 409.34 | 2.68 | 1 | 6 |
| 1I | $C_{17}H_{18}Br_2N_6S$ | 498.25 | 2.90 | 1 | 6 |

TABLE 5A-continued

| Mol ID | FORMULA | Mol-Weight | MnLogP | HBndDon | HBndAcc |
|---|---|---|---|---|---|
| 1A | $C_{17}H_{20}N_6S$ | 340.45 | 2.48 | 1 | 6 |
| 1D | $C_{17}H_{20}N_6OS$ | 356.45 | 1.99 | 2 | 7 |
| 1C | $C_{17}H_{21}N_7S$ | 355.47 | 1.99 | 3 | 7 |
| VIIA | $C_{17}H_{20}N_6S$ | 340.45 | 2.48 | 1 | 6 |
| VIIB | $C_{16}H_{19}N_7S$ | 341.44 | 1.48 | 1 | 7 |
| VIIC | $C_{17}H_{20}N_6S$ | 340.45 | 2.48 | 1 | 6 |
| VIID | $C_{16}H_{19}N_7S$ | 341.44 | 1.48 | 1 | 7 |
| VIIE | $C_{17}H_{20}N_6S$ | 340.45 | 2.48 | 1 | 6 |
| VIIF | $C_{16}H_{19}N_7S$ | 341.44 | 1.48 | 1 | 7 |
| VIIG | $C_{17}H_{20}N_6S$ | 340.45 | 1.67 | 1 | 6 |
| VIIH | $C_{16}H_{19}N_7S$ | 341.44 | 0.67 | 1 | 7 |
| VII I | $C_{17}H_{20}N_6OS$ | 356.45 | 1.99 | 2 | 7 |
| VIIJ | $C_{17}H_{21}N_7S$ | 355.47 | 1.99 | 3 | 7 |

TABLE 5B

| Mol ID | TPSA | RotBnds |
|---|---|---|
| 1B | 53.4 | 5 |
| 1G | 53.4 | 5 |
| 1H | 53.4 | 5 |
| 1I | 53.4 | 5 |
| 1A | 53.4 | 5 |
| 1D | 74.2 | 6 |
| 1C | 79.9 | 5 |
| VIIA | 53.4 | 5 |
| VIIB | 64.6 | 5 |
| VIIC | 53.4 | 5 |
| VIID | 64.6 | 5 |
| VIIE | 53.4 | 5 |
| VIIF | 64.6 | 5 |
| VIIG | 53.4 | 5 |
| VIIH | 64.6 | 5 |
| VII I | 74.2 | 6 |
| VIIJ | 79.9 | 5 |

Legend for Table 5:

MolWeight stands for Molecular Weight measured in Daltons and is a size descriptor;

Mn Log P is an average of M Log P, A Log P98 and C Log P, all of which are calculated lipophilicity/solubility estimates;

HBndDon stands for Hydrogen Bond Donor and refers to the number of atoms able to donate electrons to potentially form Hydrogen bonds;

HBndAcc stands for Hydrogen Bond Acceptor and refers to the number of atoms able to accept electrons to potentially form Hydrogen bonds;

TPSA stands for Topological Polar Surface Area and is a measure of Molecular Surface Charge/Polarity; and RotBnds stands for Rotatable Bonds which is a count of freely rotatable single bonds in the molecule.

Tables 6A and 6B: Solubility Properties

Tables 6A and 6B shows that COTI-4 (1B), COTI-4A (1A), and Formulae 1C, 1D, 1G, 1H, 1I, and VIIA to VIIJ are expected to have acceptable solubility values for drug-like compounds.

TABLE 6A

| Mol ID | FORMULA | LogD(pH 7.4) | LogS |
|---|---|---|---|
| 1B | $C_{17}H_{20}N_6S$ | 1.283 | −3.62 |
| 1G | $C_{17}H_{18}F_2N_6S$ | 1.097 | −4.24 |
| 1H | $C_{17}H_{18}Cl_2N_6S$ | 2.136 | −5.04 |
| 1I | $C_{17}H_{18}Br_2N_6S$ | 2.154 | −5.19 |
| 1A | $C_{17}H_{20}N_6S$ | 1.496 | −3.47 |
| 1D | $C_{17}H_{20}N_6OS$ | 0.832 | −3.13 |

TABLE 6A-continued

| Mol ID | FORMULA | LogD(pH 7.4) | LogS |
|---|---|---|---|
| 1C | $C_{17}H_{21}N_7S$ | 0.777 | −3.28 |
| VIIA | $C_{17}H_{20}N_6S$ | 1.557 | −3.84 |
| VIIB | $C_{16}H_{19}N_7S$ | 1.07 | −3.3 |
| VIIC | $C_{17}H_{20}N_6S$ | 1.148 | −3.42 |
| VIID | $C_{16}H_{19}N_7S$ | 0.545 | −2.87 |
| VIIE | $C_{17}H_{20}N_6S$ | 1.216 | −3.7 |
| VIIF | $C_{16}H_{19}N_7S$ | 0.837 | −3.16 |
| VIIG | $C_{17}H_{20}N_6S$ | 1.171 | −3.25 |
| VIIH | $C_{16}H_{19}N_7S$ | 0.492 | −2.7 |
| VII I | $C_{17}H_{20}N_6OS$ | 0.785 | −3.51 |
| VIIJ | $C_{17}H_{21}N_7S$ | 0.803 | −3.66 |

TABLE 6B

| Mol ID | FORMULA | Base pKa 1 | Base pKa 2 |
|---|---|---|---|
| 1B | $C_{17}H_{20}N_6S$ | 7.651 | 4.931 |
| 1G | $C_{17}H_{18}F_2N_6S$ | 7.651 | 2.346 |
| 1H | $C_{17}H_{18}Cl_2N_6S$ | 7.651 | 2.33 |
| 1I | $C_{17}H_{18}Br_2N_6S$ | 7.651 | 2.41 |
| 1A | $C_{17}H_{20}N_6S$ | 7.651 | 5.8 |
| 1D | $C_{17}H_{20}N_6OS$ | 7.651 | 6.94 |
| 1C | $C_{17}H_{21}N_7S$ | 7.651 | 7.51 |
| VIIA | $C_{17}H_{20}N_6S$ | 7.651 | 5.8 |
| VIIB | $C_{16}H_{19}N_7S$ | 7.651 | 4.63 |
| VIIC | $C_{17}H_{20}N_6S$ | 7.651 | 5.8 |
| VIID | $C_{16}H_{19}N_7S$ | 7.651 | 4.63 |
| VIIE | $C_{17}H_{20}N_6S$ | 7.651 | 5.8 |
| VIIF | $C_{16}H_{19}N_7S$ | 7.651 | 4.63 |
| VIIG | $C_{17}H_{20}N_6S$ | 7.651 | 5.8 |
| VIIH | $C_{16}H_{19}N_7S$ | 7.651 | 4.63 |
| VII I | $C_{17}H_{20}N_6OS$ | 7.651 | 6.94 |
| VIIJ | $C_{17}H_{21}N_7S$ | 7.651 | 7.51 |

Legend for Table 6:

Log D(7.4) is a measure of relative solubility in octanol vs water at a specific pH, in this case pH=7.4;

Log S is the logarithm of the calculated solubility in pure water usually measured at 25 degrees centigrade;

pKa is a calculated estimate of the pH at which the drug or substructures of the drug is 50% ionized and 50% is unionized.

Table 7: Efficacy (Log $IC_{50}$)

Tables 7A (in-silico) and 7B (actual in-vitro data) show that COTI-4 (1B), COTI-4A (1A), and Formulae 1C, 1D, 1G, 1H, 1I, and VIIA to VIIJ are predicted to have sub-micromolar in vitro $IC_{50}$ vs human SCLC cell lines. Actual measurements obtained in vitro confirm the in silico prediction of activity at sub-micromolar $IC_{50}$ levels for 1A and 1B.

TABLE 7A

| Mol ID | FORMULA | DMS114 (ProbLog $IC_{50} < -6$) | SHP-77 (ProbLog $IC_{50} < -6$) | DMS253 (ProbLog $IC_{50} < -6$) |
|---|---|---|---|---|
| 1B | $C_{17}H_{20}N_6S$ | 0.995 | 0.979 | 0.995 |
| 1G | $C_{17}H_{18}F_2N_6S$ | 0.05 | 0.019 | 0.052 |
| 1H | $C_{17}H_{18}Cl_2N_6S$ | 0.56 | 0.024 | 0.064 |
| 1I | $C_{17}H_{18}Br_2N_6S$ | 0.031 | 0.012 | 0.032 |
| 1A | $C_{17}H_{20}N_6S$ | 0.941 | 0.324 | 0.95 |
| 1D | $C_{17}H_{20}N_6OS$ | 0.122 | 0.042 | 0.118 |
| 1C | $C_{17}H_{21}N_7S$ | 0.873 | 0.217 | 0.872 |
| VIIA | $C_{17}H_{20}N_6S$ | 0.986 | 0.919 | 0.986 |
| VIIB | $C_{16}H_{19}N_7S$ | 0.923 | 0.294 | 0.925 |
| VIIC | $C_{17}H_{20}N_6S$ | 0.973 | 0.59 | 0.972 |
| VIID | $C_{16}H_{19}N_7S$ | 0.888 | 0.247 | 0.891 |
| VIIE | $C_{17}H_{20}N_6S$ | 0.976 | 0.443 | 0.977 |
| VIIF | $C_{16}H_{19}N_7S$ | 0.954 | 0.368 | 0.955 |
| VIIG | $C_{17}H_{20}N_6S$ | 0.986 | 0.93 | 0.985 |

TABLE 7A-continued

| Mol ID | FORMULA | DMS114 (ProbLog $IC_{50} < -6$) | SHP-77 (ProbLog $IC_{50} < -6$) | DMS253 (ProbLog $IC_{50} < -6$) |
|---|---|---|---|---|
| VIIH | $C_{16}H_{19}N_7S$ | 0.942 | 0.345 | 0.942 |
| VII I | $C_{17}H_{20}N_6OS$ | 0.135 | 0.046 | 0.128 |
| VIIJ | $C_{17}H_{21}N_7S$ | 0.875 | 0.22 | 0.875 |

TABLE 7B

| Mol ID | FORMULA | DMS114 (Log $IC_{50}$) | SHP-77 (Log $IC_{50}$) |
|---|---|---|---|
| 1B | $C_{17}H_{20}N_6S$ | −7.523 | −6.762 |
| 1A | $C_{17}H_{20}N_6S$ | −6.187 | −4.969 |

Legend for Table 7:

DMS114 is a human small cell lung cancer line that is maintained by the National Cancer Institute in the United States;

SHP-77 is a human small cell lung cancer line that is maintained by the National Cancer Institute in the United States; and DMS153 and DMS253 are human small cell lung cancer lines that are maintained by the National Cancer Institute in the United States. These two cell lines are expected to have similar properties in vitro.

Table 8: Efficacy (Log $IC_{50}$)

Tables 8A (in-silico) and 8B (actual in-vitro data) show that COTI-4 (1B), COTI-4A (1A), and Formulae 1C, 1D, 1G, 1H, 1I, and VIIA to VIIJ are not predicted to have sub-micromolar in vitro $IC_{50}$ vs human non-SCLC cell lines. Actual measurements obtained in vitro confirm the in silico prediction of $IC_{50}$ levels for 1A and 1B. However, both compounds were effective in treating non-SCLC cell lines at higher $IC_{50}$ levels.

TABLE 8A

| Mol ID | FORMULA | A549 (ProbLog $IC_{50} < -6$) | H226 (ProbLog $IC_{50} < -6$) | H460 (ProbLog $IC_{50} < -6$) |
|---|---|---|---|---|
| 1B | $C_{17}H_{20}N_6S$ | 0 | 0.012 | 0 |
| 1G | $C_{17}H_{18}F_2N_6S$ | 0 | 0 | 0.001 |
| 1H | $C_{17}H_{18}Cl_2N_6S$ | 0 | 0.001 | 0 |
| 1I | $C_{17}H_{18}Br_2N_6S$ | 0 | 0.003 | 0 |
| 1A | $C_{17}H_{20}N_6S$ | 0 | 0.013 | 0.001 |
| 1D | $C_{17}H_{20}N_6OS$ | 0.004 | 0 | 0.007 |
| 1C | $C_{17}H_{21}N_7S$ | 0 | 0 | 0.002 |
| VIIA | $C_{17}H_{20}N_6S$ | 0 | 0.013 | 0.003 |
| VIIB | $C_{16}H_{19}N_7S$ | 0 | 0.01 | 0 |
| VIIC | $C_{17}H_{20}N_6S$ | 0 | 0.015 | 0 |
| VIID | $C_{16}H_{19}N_7S$ | 0 | 0.011 | 0 |
| VIIE | $C_{17}H_{20}N_6S$ | 0 | 0.013 | 0.003 |
| VIIF | $C_{16}H_{19}N_7S$ | 0 | 0.01 | 0 |
| VIIG | $C_{17}H_{20}N_6S$ | 0 | 0.014 | 0 |
| VIIH | $C_{16}H_{19}N_7S$ | 0 | 0.013 | 0 |
| VII I | $C_{17}H_{20}N_6OS$ | 0.003 | 0 | 0.006 |
| VIIJ | $C_{17}H_{21}N_7S$ | 0 | 0 | 0.002 |

TABLE 8B

| Mol ID | FORMULA | A549 (Log $IC_{50}$) | H226 (Log $IC_{50}$) | H460 (Log $IC_{50}$) |
|---|---|---|---|---|
| 1B | $C_{17}H_{20}N_6S$ | −5.167 | −5.602 | −5.292 |
| 1A | $C_{17}H_{20}N_6S$ | −5.804 | −4.197 | −4.140 |

Legend for Table 8:

A549 is a adenocarcinoma-derived cell line that is maintained by the National Cancer Institute in the United States;

H226 is a squamous cell carcinoma-derived cell line that is maintained by the National Cancer Institute in the United States; and, H460 is a large cell carcinoma-derived cell line that is maintained by the National Cancer Institute in the United States.

Tables 9A, 9B, 10A and 10B: Physical Chemical Properties

Tables 9A, 9B, 10A and 10B show that COTI-4 (1B), COTI-4A (1A), are "drug-like" with good drug like physical properties whereas Formulae S00115; S00340; and S00341 of Chinese Patent Application No. 1891701 are not.

TABLE 9A

S00115

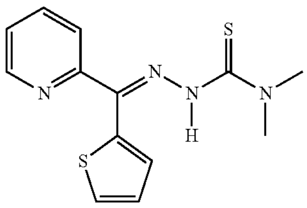 [SMILES: CN(C)C(=S)N/N=C(/c1ccccn1)c1cccs1]

S00340

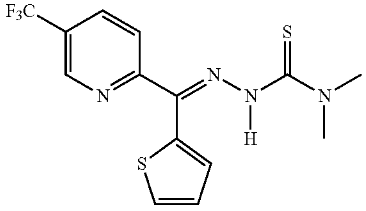 [SMILES: CN(C)C(=S)N/N=C(/c1ccc(C(F)(F)F)cn1)c1cccs1]

S0034

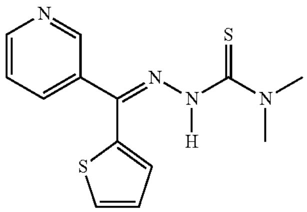 [SMILES: CN(C)C(=S)N/N=C(/c1cccnc1)c1cccs1]

| Mol ID | FORMULA | MolWeight | MnLogP | HBndDon | HBndAcc |
|---|---|---|---|---|---|
| 1B | $C_{17}H_{20}N_6S$ | 340.45 | 1.67 | 1 | 6 |
| 1A | $C_{17}H_{20}N_6S$ | 340.45 | 2.48 | 1 | 6 |
| S00115 | $C_{13}H_{14}N_4S_2$ | 290.41 | 2.26 | 1 | 4 |
| S00340 | $C_{14}H_{13}F_3N_4S_2$ | 358.41 | 2.26 | 1 | 4 |
| S00341 | $C_{13}H_{14}N_4S_2$ | 290.41 | 2.26 | 1 | 4 |

TABLE 9B

| Mol ID | TPSA | RotBnds |
|---|---|---|
| 1B | 53.4 | 5 |
| 1A | 53.4 | 5 |
| S00115 | 38.7 | 5 |
| S00340 | 38.7 | 5 |
| S00341 | 38.7 | 5 |

Legend for Table 9:

MolWeight stands for Molecular Weight measured in Daltons and is a size descriptor;

Mn Log P is an average of M Log P, A Log P98 and C Log P, all of which are calculated lipophilicity/solubility estimates;

HBndDon stands for Hydrogen Bond Donor and refers to the number of atoms able to donate electrons to potentially form Hydrogen bonds;

HBndAcc stands for Hydrogen Bond Acceptor and refers to the number of atoms able to accept electrons to potentially form Hydrogen bonds;

TPSA stands for Topological Polar Surface Area and is a measure of Molecular Surface Charge/Polarity; and RotBnds stands for Rotatable Bonds which is a count of freely rotatable single bonds in the molecule.

TABLE 10A

| Mol ID | FORMULA | LogD(pH 7.4) | LogS |
|---|---|---|---|
| 1B | $C_{17}H_{20}N_6S$ | 1.283 | −3.62 |
| 1A | $C_{17}H_{20}N_6S$ | 1.496 | −3.47 |
| S00115 | $C_{13}H_{14}N_4S_2$ | 2.406 | −3.67 |
| S00340 | $C_{14}H_{13}F_3N_4S_2$ | 2.549 | −4.18 |
| S00341 | $C_{13}H_{14}N_4S_2$ | 2.127 | −3.3 |

TABLE 10B

| Mol ID | FORMULA | Base pKa 1 |
|---|---|---|
| 1B | $C_{17}H_{20}N_6S$ | 7.651 |
| 1A | $C_{17}H_{20}N_6S$ | 7.651 |
| S00115 | $C_{13}H_{14}N_4S_2$ | 4.782 |
| S00340 | $C_{14}H_{13}F_3N_4S_2$ | 5.477 |
| S00341 | $C_{13}H_{14}N_4S_2$ | 4.979 |

Legend for Table 10:

Log D(7.4) is a measure of relative solubility in octanol vs water at a specific pH, in this case pH=7.4;

Log S is the logarithm of the calculated solubility in pure water usually measured at 25 degrees centigrade;

pKa is a calculated estimate of the pH at which the drug or substructures of the drug is 50% ionized and 50% is unionized.

Table 11: Efficacy (Log $IC_{50}$)

Tables 11A (in-silico) and 11B (actual in-vitro data) show that COTI-4 (1B), COTI-4A (1A) are predicted to have sub-micromolar in vitro $IC_{50}$ vs human SCLC cell lines, whereas Formulae S00115; S00340; and S00341 of Chinese Patent Application No. 1891701 are not. Actual measurements obtained in vitro confirm the in silico prediction of activity at sub-micromolar $IC_{50}$ levels for 1A and 1B.

TABLE 11A

| Mol ID | FORMULA | DMS114 (ProbLog $IC_{50}<-6$) | SHP-77 (ProbLog $IC_{50}<-6$) | DMS253 (ProbLog $IC_{50}<-6$) |
|---|---|---|---|---|
| 1B | $C_{17}H_{20}N_6S$ | 0.995 | 0.979 | 0.995 |
| 1A | $C_{17}H_{20}N_6S$ | 0.941 | 0.324 | 0.95 |
| S00115 | $C_{13}H_{14}N_4S_2$ | 0.008 | 0.002 | 0.03 |
| S00340 | $C_{14}H_{13}F_3N_4S_2$ | 0.035 | 0.017 | 0.174 |
| S00341 | $C_{13}H_{14}N_4S_2$ | 0.006 | 0.002 | 0.025 |

TABLE 11B

| Mol ID | FORMULA | DMS114 (Log $IC_{50}$) | SHP-77 (Log $IC_{50}$) |
|---|---|---|---|
| 1B | $C_{17}H_{20}N_6S$ | −7.523 | −6.762 |
| 1A | $C_{17}H_{20}N_6S$ | −6.187 | −4.969 |

Legend for Table 11:

DMS114 is a human small cell lung cancer line that is maintained by the National Cancer Institute in the United States;

SHP-77 is a human small cell lung cancer line that is maintained by the National Cancer Institute in the United States; and DMS153 and DMS253 are human small cell lung cancer lines that are maintained by the National Cancer Institute in the United States. These two cell lines are expected to have similar properties in vitro.

Table 12: Efficacy (Log $IC_{50}$)

Tables 12A (in-silico) and 12B (actual in-vitro data) show that COTI-4 (1B) and COTI-4A (1A) and Formulae S00115; S00340; and S00341 of Chinese Patent Application No. 1891701 are not predicted to have sub-micromolar in vitro $IC_{50}$ vs human non-SCLC cell lines. Actual measurements obtained in vitro confirm the in silico prediction of $IC_{50}$ levels for 1A and 1B. However, both compounds were effective in treating non-SCLC cell lines at higher $IC_{50}$ levels.

TABLE 12A

| Mol ID | FORMULA | A549 (ProbLog $IC_{50}<-6$) | H226 (ProbLog $IC_{50}<-6$) | H460 (ProbLog $IC_{50}<-6$) |
|---|---|---|---|---|
| 1B | $C_{17}H_{20}N_6S$ | 0 | 0.012 | 0 |
| 1A | $C_{17}H_{20}N_6S$ | 0 | 0.013 | 0.001 |
| S00115 | $C_{13}H_{14}N_4S_2$ | 0 | 0 | 0 |
| S00340 | $C_{14}H_{13}F_3N_4S_2$ | 0 | 0 | 0.078 |
| S00341 | $C_{13}H_{14}N_4S_2$ | 0 | 0 | 0 |

TABLE 12B

| Mol ID | FORMULA | A549 (Log $IC_{50}$) | H226 (Log $IC_{50}$) | H460 (Log $IC_{50}$) |
|---|---|---|---|---|
| 1B | $C_{17}H_{20}N_6S$ | −5.167 | −5.602 | −5.292 |
| 1A | $C_{17}H_{20}N_6S$ | −5.804 | −4.197 | −4.140 |

Legend for Table 12:

A549 is a adenocarcinoma-derived cell line that is maintained by the National Cancer Institute in the United States;

H226 is a squamous cell carcinoma-derived cell line that is maintained by the National Cancer Institute in the United States; and, H460 is a large cell carcinoma-derived cell line that is maintained by the National Cancer Institute in the United States.

Example 5

COTI-4 (1B)

To assess the efficacy of compounds according to the present invention in the treatment of cancer, in vitro activity expressed as $IC_{50}$ (represents the concentration of an inhibitor that is required for 50% inhibition of its target, in nmol) was measured for several cancer cell lines using standard methods for such tests known to persons skilled in the art. Briefly, cells were plated in plastic tissue culture plates and grown under standard conditions for each cell line, in carbon dioxide/oxygen atmosphere in plastic tissue culture plates, in the presence of COTI-4 or COTI-4A compounds at 35° C. for 3 days. Control cultures were treated with vehicle minus compound. Cells were counted after 3 days in culture and at a cell density of no more than 80%. The following cell lines, obtained from the National Cancer Institute, were tested: human SCLC cell lines DMS 153, DMS114, SHP77; human NSCLC cell lines H226, A460, A549; human breast cancer cell lines T47D, MCF7; human colon cancer cell line HT29; and, human Leukemia cell lines K562, HL60. The results of these assays are presented in Table 13.

TABLE 13 in vitro $IC_{50}$ against cancer cell lines

| Cell Line | Tumor Type | COTI-4 (1B) $IC_{50}$ (nM) | COTI-4A (1A) $IC_{50}$ (nM) |
|---|---|---|---|
| SHP77 | SCLC | 173 +/− 28 | 10,000 |
| DMS153 | SCLC | 130 +/− 17 | 400 |
| DMS114 | SCLC | 30 +/− 7 | 650 |
| H226 | NSCLC | 2,500 +/− 319 | 90,000 |
| A460 | NSCLC | 5,100 +/− 485 | 100,000 |
| A549 | NSCLC | 6,800 +/− 741 | 1500 |
| T47D | Breast Cancer | 224 +/− 15 | Not tested |
| MCF7 | Breast Cancer | 291 +/− 22 | Not tested |
| HT29 | Colorectal Cancer | 83 +/− 13 | Not tested |
| K562 | Leukemia | 95 +/− 12 | Not tested |
| HL60 | Leukemia | 318 +/− 39 | Not tested |

Table 13 shows that both COTI-4 and COTI-4A possess potent activity against SCLC tumor cell types, as well as several other tumor cell types such as breast cancer, colorectal cancer and Leukemia. Both drugs had an $IC_{50}$ of less than 1000 nM for the DMS153 and DMS114 cell lines. Neither drug possessed nanomolar level activity against NSCLC cell types, although both exhibited efficacy in the treatment of those cell types. Both drugs therefore exhibit selectivity in lung cancer treatment towards SCLC cell types. The in vitro data also confirms and validates the in-silico predictions of efficacy, which estimated that less than 1 μM (1000 nM) would be required for efficacy in the DMS 114 cell line and that neither drug would have sub-micromolar activity in treating NSCLC cell lines.

Example 6

Resistance Testing

In order to evaluate the induction of resistance in vitro, compounds according to Formula 1B (COTI-4) were tested in head to head comparisons against conventional therapeutic agents cisplatin and another member of the taxane family (to which paclitaxel belongs), docetaxel (sold under the brand name Taxotere® by Sanofi-Aventis). The compounds designated COTI-2 and COTI-219, previously referenced herein, were also tested.

$IC_{50}$ values were obtained using methods known to persons skilled in the art with two different human SCLC cell lines (DMS153 and SHP77) obtained from the National Cancer Institute. The surviving 50% of cells from the initial $IC_{50}$ tested were harvested and cultured for 5 days, after which time this new generation of cells was re-treated with the same agent and a new $IC_{50}$ value was established. The procedure was repeated for a total of 5 generations. Emerging resistance was identified by increasing $IC_{50}$ values in successive generations. The results are shown in FIGS. 14 and 15 (DMS153 and SHP77 cell lines, respectively), where the ordinate axis is provided in terms of the ratio of the $IC_{50}$ value of the drug resistant cells to the $IC_{50}$ value of the non-drug resistant parental generation.

Referring to FIGS. 14 and 15, for all cell lines, compounds of the present invention were more effective in treating the drug resistant cells than the cisplation or the taxane docetaxel (labeled paclitaxel in FIGS. 14 and 15). COTI-4 exhibited little to no emerging resistance over 5 generations. This was in marked contrast to the conventional therapies cisplatin and docetaxel, which showed significant increases in $IC_{50}$ for both cell lines, even after only one round of selection. The SHP77 cell line, in particular, is known to be resistant to conventional agents; however, COTI 4 showed only a marginal increase in resistance in this cell line, with less than a two fold increase in $IC_{50}$ observed over five successive generations of cancerous cells treated with the compound.

In fact, COTI-4 demonstrated a statistically significant tendency to decrease resistance (less than a one fold increase in $IC_{50}$ observed over five successive generations of cancerous cells treated with the compound) in the DMS153 cell line. The tendency of COTI-4 to decrease resistance in the DMS153 cell line was even greater than that of the prior art compounds COTI-2 and COTI-219. COTI-4 therefore exhibits a collateral sensitivity whereby the resistance of cells is decreased over successive generations and the drug might actually become more effective over time against these cell lines.

Example 7

In Vivo Toxicity Testing

An escalating dose acute toxicity study was conducted with COTI-2, COTI-4 (Formula 1B) and COTI-219. Standard lab mice were divided into four treatment groups (control, 4, 8, 16 mg/kg) with four animals per group. It should be noted that the highest dose was approximately 10 times the estimated effective dose. Mice were given alternate day IP injections for 28 days. Weight loss/gain of the mice was measured and the mice were observed for adverse effects such as vomiting, diarrhea, seizures, etc.

Referring to FIG. 16, the weight loss of the mice was plotted on the ordinate axis (in grams, +/− standard error), with the number of days of treatment plotted on the abscissa. None of the mice exhibited any signs of acute toxicity at any of the dosages and no adverse events were observed, although one mouse in the high dose control group was euthanized on day 18 due to non-drug related causes (this reduced the high dose group to n=3 for the final ten days of the study). These results indicated that COTI-4 is safe and non-toxic at all dosage levels, even at up to 10 times the therapeutic dose, which is surprising in the field of anti-cancer drugs.

The above-described embodiments of the present invention are intended to be examples only. Alterations, modifications and variations may be effected to the particular embodiments by those of skill in the art without departing from the scope of the invention, which is defined solely by the claims appended hereto.

We claim:

1. A compound of Formula II:

Formula II

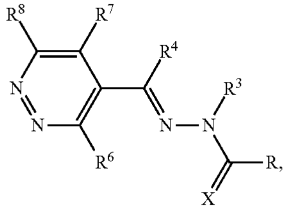

a pharmaceutically-acceptable salt, tautomer, optical isomer, E-isomer, Z-isomer, and/or combination thereof;

wherein:

X is selected from S;

R and $R^3$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group;

$R^4$ is selected from a substituted or unsubstituted aromatic group, or a substituted or unsubstituted heteroaromatic group; and $R^6$ to $R^8$ are each independently selected from H, halo, hydroxyl, amino, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group.

2. The compound of claim 1, wherein R and $R^3$ are each independently selected from H, halo, hydroxyl, cyano, substituted or unsubstituted alkyl, substituted or unsubstituted alkenyl, substituted or unsubstituted alkynyl, substituted or unsubstituted haloalkyl, substituted or unsubstituted hydroxyalkyl, substituted or unsubstituted alkoxy, a substituted or unsubstituted heterocyclic group, a substituted or unsubstituted aromatic group, a substituted or unsubstituted heteroaromatic group, carboxyl, alkylcarbonyl, arylcarbonyl, cycloalkylcarbonyl, heterocyclylcarbonyl, amino, aminoalkyl, alkylaminoalkyl, heterocyclylalkyl, aralkyl, arylalkenyl, arylalkynyl, alkylthio, alkylamino, arylamino, heteroarylamino, aralkylamino, alkylaminoalkylamino, arylthio, aralkylthio, aryloxy, aralkoxy, heterocyclylalkoxy, heterocyclyloxyalkyl, cycloalkyl, and cycloalkenyl.

3. The compound of claim 2, wherein $R^4$ is selected from a substituted or unsubstituted pyridinyl group or a substituted or unsubstituted phenyl group and $R^3$ is H or substituted or unsubstituted alkyl.

4. The compound of claim 3, wherein the substituted pyridinyl group is substituted in the para position or the substituted phenyl group is substituted in the ortho position.

5. The compound of claim 3, wherein the substituted pyridinyl group or the substituted phenyl group is substituted with the hydroxyl, amino, or aminoalkyl.

6. The compound of claim 3, wherein the pyridinyl group is selected from a 2-pyridinyl group, a 3-pyridinyl group, or a 4-pyridinyl group.

7. The compound of claim 1, wherein $R^6$ to $R^8$ are each independently selected from H, halo, hydroxyl, amino, nitro, a substituted or unsubstituted hydrocarbon group, a substituted or unsubstituted heterogeneous group.

8. The compound of claim 7, wherein $R^6$ to $R^8$ are each H.

9. The compound of claim 1, wherein R is $NR^1R^2$, wherein:

$R^1$ and $R^2$ are each independently selected from H, halo, hydroxy, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, or $R^1$ and $R^2$ together form a substituted or unsubstituted heterocyclic group, a substituted or unsubstituted aromatic group, or a substituted or unsubstituted heteroaromatic group.

10. The compound of claim 9, wherein $R^1$ and $R^2$ together form a substituted or unsubstituted heterocyclic group.

11. A compound of Formula II:

Formula II

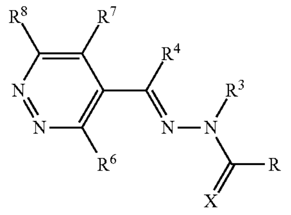

a pharmaceutically-acceptable salt, tautomer, optical isomer, E-isomer, Z-isomer, and/or combination thereof;

wherein:

X is selected from S or 0;

$R^3$ and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and $R^6$ to $R^8$ are each independently selected from H, halo, hydroxyl, amino, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, wherein R is $NR^1R^2$, wherein $NR^1R^2$ is a substituted or unsubstituted piperazinyl group.

12. The compound of claim 11, wherein $NR^1R^2$ is:

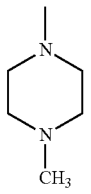

or

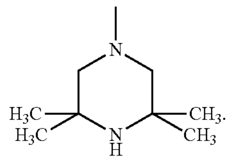

13. A compound of Formula II:

Formula II

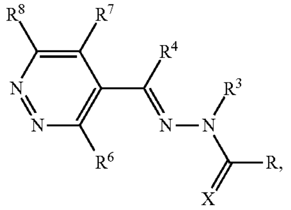

a pharmaceutically-acceptable salt, tautomer, optical isomer, E-isomer, Z-isomer, and/or combination thereof;

wherein:

X is selected from S or 0;

R, $R^3$ and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and $R^6$ to $R^8$ are each independently selected from H, halo, hydroxyl, amino, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, wherein the compound is:

1A

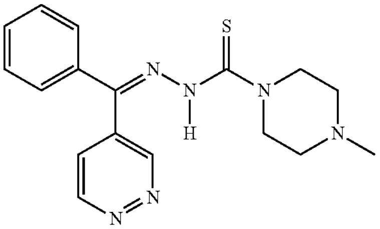
,

1C

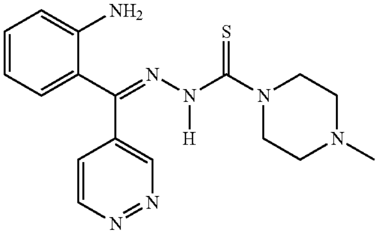
,

1D

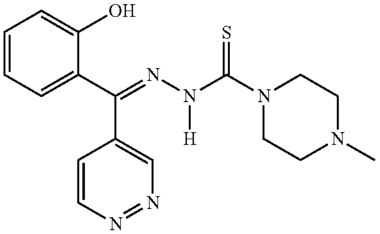
,

1E

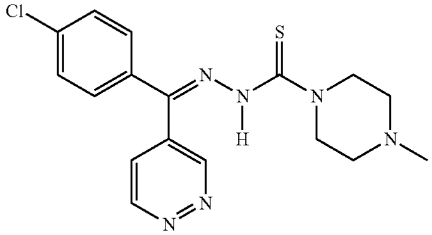
,

1F

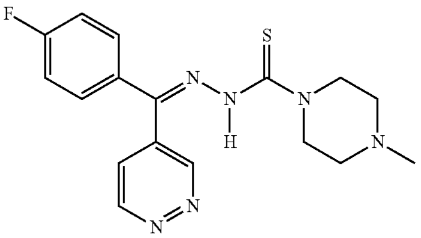

a pharmaceutically-acceptable salt, tautomer, optical isomer, E-isomer, Z-isomer, and/or combination thereof.

14. A compound of Formula II:

Formula II

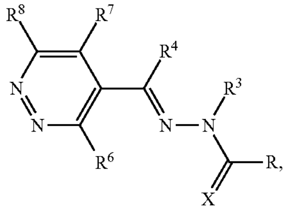

a pharmaceutically-acceptable salt, tautomer, optical isomer, E-isomer, Z-isomer, and/or combination thereof;

wherein:

X is selected from S or 0;

R, $R^3$ and $R^4$ are each independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group; and $R^6$ to $R^8$ are each independently selected from H, halo, hydroxyl, amino, nitro, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, wherein the compound is:

1J

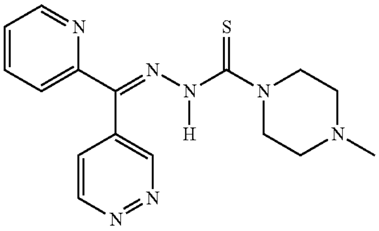
,

1K

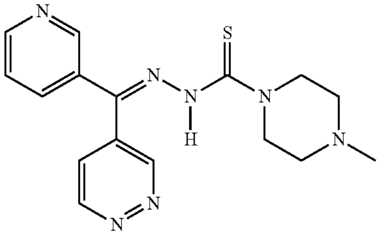
, or

1L

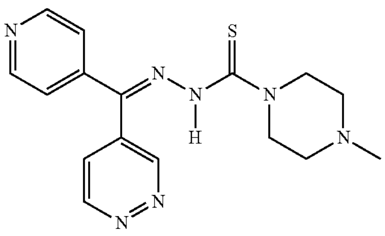
.

a pharmaceutically-acceptable salt, tautomer, optical isomer, E-isomer, Z-isomer, and/or combination thereof.

15. A pharmaceutical composition comprising the compound of claim 1 and at least one pharmaceutically acceptable carrier and/or diluent.

16. A method for preparing the compound of claim 1, the method comprising:

a) reacting a compound of Formula IV with an amine $NHR^1R^2$ to form an intermediate of formula V:

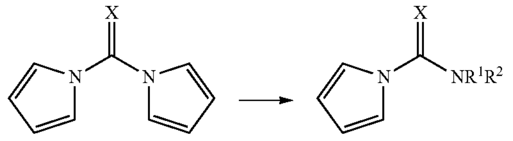

Formula IV Formula V b) reacting the intermediate of Formula V with $NHR^3NH_2$ to form an intermediate of Formula VI:

Formula VI

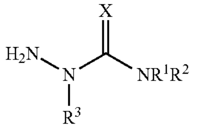

c) reacting the intermediate of Formula VI with a ketone:

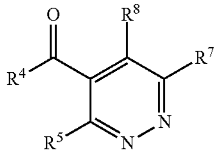

under condensation conditions, to form the compound of Formula II.

* * * * *

UNITED STATES PATENT AND TRADEMARK OFFICE

CERTIFICATE OF CORRECTION

PATENT NO. : 8,466,151 B2
APPLICATION NO. : 12/810722
DATED : June 18, 2013
INVENTOR(S) : Wayne R Danter and Cheuk Kun Lau It is certified that error appears in the above-identified patent and that said Letters Patent is hereby corrected as shown below:

On the Title Page, Item (75), Inventors, delete "Kun Kun Lau" and insert --Cheuk Kun Lau--, therefor.

Signed and Sealed this
Twentieth Day of August, 2013

Teresa Stanek Rea
*Acting Director of the United States Patent and Trademark Office*

UNITED STATES PATENT AND TRADEMARK OFFICE

CERTIFICATE OF CORRECTION

PATENT NO. : 8,466,151 B2
APPLICATION NO. : 12/810722
DATED : June 18, 2013
INVENTOR(S) : Danter et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 133 days.

Signed and Sealed this
Eighth Day of September, 2015

Michelle K. Lee

Michelle K. Lee
*Director of the United States Patent and Trademark Office*